(12) United States Patent
Yan et al.

(10) Patent No.: US 10,071,962 B2
(45) Date of Patent: *Sep. 11, 2018

(54) ANDROGEN RECEPTOR MODULATORS AND METHODS FOR THEIR USE

(71) Applicants: British Columbia Cancer Agency Branch, Vancouver (CA); The University of British Columbia, Vancouver (CA)

(72) Inventors: Luping Yan, Vancouver (CA); Raymond J. Andersen, Vancouver (CA); Marianne Dorothy Sadar, West Vancouver (CA); Nasrin R. Mawji, Burnaby (CA); Carmen Adriana Banuelos, Richmond (CA)

(73) Assignees: British Columbia Cancer Agency Branch, Vancouver (CA); The University of British Columbia, Vancouver (CA)

( * ) Notice: Subject to any disclaimer, the term of this patent is extended or adjusted under 35 U.S.C. 154(b) by 0 days.

This patent is subject to a terminal disclaimer.

(21) Appl. No.: 15/626,526

(22) Filed: Jun. 19, 2017

(65) Prior Publication Data
US 2017/0283377 A1    Oct. 5, 2017

Related U.S. Application Data

(63) Continuation of application No. 14/726,129, filed on May 29, 2015, now Pat. No. 9,682,933.

(60) Provisional application No. 62/005,714, filed on May 30, 2014.

(51) Int. Cl.
C07D 207/38    (2006.01)
A61K 31/4015    (2006.01)

(52) U.S. Cl.
CPC ........ C07D 207/38 (2013.01); A61K 31/4015 (2013.01)

(58) Field of Classification Search
CPC .................................................. C07D 207/38
See application file for complete search history.

(56) References Cited

U.S. PATENT DOCUMENTS

| 9,487,479 | B2 | 11/2016 | Sadar et al. | |
| 9,682,933 | B2* | 6/2017 | Yan | A61K 31/4015 |
| 2008/0057068 | A1 | 3/2008 | Dalton et al. | |
| 2011/0230539 | A1* | 9/2011 | Sadar | A61K 31/495 514/423 |
| 2015/0344424 | A1 | 12/2015 | Yan et al. | |
| 2017/0283377 | A1 | 10/2017 | Yan et al. | |

FOREIGN PATENT DOCUMENTS

| JP | H 03-17057 A | 1/1991 |
| WO | WO 2000/001813 A2 | 1/2000 |
| WO | WO 2010/020055 A1 | 2/2010 |
| WO | WO 2015/184393 A1 | 12/2015 |

OTHER PUBLICATIONS

Coleman et al. Circ Res. 1999, 84, 1268-1276 (Year: 1999).*
Berge, S.M. et al., "Pharmaceutical Salts." Pharmaceutical Sciences, 66(1):1-19 (1977).
Bisson, W.H. et al., "Discovery of antiandrogen activity of nonsteroidal scaffolds of marketed drugs." PNAS, 104(29):11927-11932 (2007).
Blaszczyk, N. et al., "Osteoblast-Derived factors Induce Androgen-Independent Proliferation and Expression of Prostate-Specific Antigen in Human Prostate Cancer Cells." Clin. Cancer Res., 10:1860-1869 (2004).
Brantley et al., "Synthetic studies of trichloroleucine marine natural products. Michael addition of LiCCl3 to N-crotonylcamphor sultam." Organic Letters, 1(13): 2165-2167 (1999).
Bruckheimer, E.M. et al., "Apoptosis in prostate carcinogenesis A growth regulator and a therapeutic target." Cell Tissue Res, 301:153-162 (2000).
CAS Registry No. 88274-93-5, entered STN Nov. 16, 1984, 4 pages.
Chang, C. et al., "Development of Peptide Antagonists for the Androgen Receptor Using Combinatorial Peptide Phage Display." Molecular Endocrinology, 19(10):2478-2490 (2005).
Clinton and Hua, "Estrogen action in human ovarian cancer." Critical Reviews in Oncology/Hematology, 25:1-9 (1997).
Culig, Zoran et al., "Androgen Receptor Activation in Prostatic Tumor Cell Lines by Insulin-like Growth Factor-I, Keratinocyte Growth Factor, and Epidermal Growth Factor." Cancer Research, 54:5474-5478 (1994).
Dehm, S. et al., "Ligand-independent Androgen Receptor Activity is Activation Function-2-independent and Resistant to Antiandrogens in Androgen Refractory Prostate Cancer Cells." The Journal of Biological Chemistry, 281(38):27882-27893 (2006).
Dehm, S. et al., "Splicing of a Novel Androgen Receptor Exon Generates a Constitutively Active Androgen Receptor that Mediates Prostate Cancer Therapy Resistance." Cancer Research, 68:5469-5477 (2008).

(Continued)

Primary Examiner — Matthew P Coughlin
(74) Attorney, Agent, or Firm — Foley Hoag LLP

(57) ABSTRACT

Compounds having a structure of Structure I:

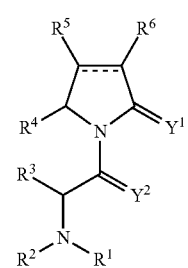

or a pharmaceutically acceptable salt, tautomer or stereoisomer thereof, wherein $R^1$, $R^2$, $R^3$, $R^4$, $R^6$, $Y^1$ and $Y^2$ are as defined herein, and wherein at least one of $R^3$ or $R^4$ is a straight-chain $C_1$-$C_6$ haloalkyl, are provided. Uses of such compounds for treatment of various indications, including prostate cancer, as well as methods of treatment involving such compounds are also provided.

23 Claims, 3 Drawing Sheets

(56) References Cited

OTHER PUBLICATIONS

Dehm et al., "Selective Role of an NH2-Terminal WxxLF Motif for Aberrant Androgen Receptor Activation in Androgen Depletion-Independent Prostate Cancer Cells." Cancer Research, 67(20): 10067-10077 (2007).
Edmondson, J. M. et al., "The human ovarian surface epithelium is an androgen responsive tissue." British Journal of Cancer, 86:879-885 (2002).
Erickson and Wells, "New polychlorinated metabolites from a Barrier Reef collection of the sponge Dysidea herbacea." Australian Journal of Chemistry, 35(1): 31-38 (1982).
Estebanez-Perpiñá, E. et al., "A surface on the androgen receptor that allosterically regulates coactivator binding." PNAS, 104(41):16074-16079 (2007).
Estebanez-Perpiñá, E. et al., "The Molecular Mechanisms of Coactivator Utilization in Ligand-dependent Transactivation by the Androgen Receptor." The Journal of Biological Chemistry, 280(9):8060-8068 (2005).
European Application No. EP 09807798.5, Extended European Search Report dated May 8, 2012, 9 pages.
Fahey et al., "Geographic variation of natural products of tropical nudibranch Asteronotus cespitosus." Journal of Chemical Ecology, 28(9): 1773-1785 (2002).
Gleave, Martin et al., "Acceleration of Human Prostate Cancer Growth in Vivo by Factors Produced by Prostate and Bone Fibroblasts." Cancer Research, 51:3753-3761 (1991).
Gregory, Christopher et al., "Epidermal Growth Factor Increases Coactivation of the Androgen Receptor in Recurrent Prostate Cancer." The Journal of Biological Chemistry, 279(8):7119-7130 (2004).
Guinan, P.D. et al., "Impotence Therapy and Cancer of the Prostate." The American Journal of Surgery, 131:599-600 (1976).
Guo, Zhiyong et al., "A Novel Androgen Receptor Splice Variant Is Up-regulated during Prostate Cancer Progression and Promotes Androgen Depletion—Resistant Growth." Cancer Research, 69:2305-13 (2009).
He, B. et al., "Structural Basis for Androgen Receptor Interdomain and Coactivator Interactions Suggests a Transition in Nuclear Receptor Activation Function Dominance." Molecular Cell, 16:425-438 (2004).
Helzlsouer, Kathy J., et al., "Serum Gonadotropins and Steroid Hormones and the Development of Ovarian Cancer." JAMA, 274(24):1926-1930 (1995).
Hofheinz and Oberhansli, "Dysidin, a novel chlorine containing natural product from the spong Dysidea herbacea", Helv. Chim. Acta, 60: 660-669 (1977) (with English Summary).
Horoszewicz, J.S. et al., "LNCaP Model of Human Prostatic Carcinoma." Cancer Research, 43:1809-1818 (1983).
Hosseini et al., "Dipeptide Analogues Containing 4-Ethoxy-3-pyrrolin-2-ones." Organic Letterss, 8(10):2103-2106 (2006).
Hosseini et al., "Pyrrolidinone-modified di- and tripeptides: highly diastereoselective preparation and investigation of their stability." Organic & Biomolecular Chemistry, 5: 3486-3494 (2007).
Hu, R. et al., "Ligand-Independent Androgen Receptor Variants Derived from Splicing of Cryptic Exons Signify Hormone-Refractory Prostate Cancer." Cancer Research, 69:16-22 (2009).
Huber, P.R. et al., "Prostate Specific Antigen. Experimental and Clinical Observations." Scand. J. Urol Nephrol., 104:33-39 (1987).
Hur, E. et al., "Recognition and Accommodation at the Androgen Receptor Coactivator Binding Interface." PLoS Biology, 2(9)(e274):1303-1312 (2004).
Isaacs, J.T., "Antagonistic Effect of Androgen on Prostatic Cell Death." The Prostate, 5:545-557 (1984).
Jackson, J. A. et al., "Prostatic Complications of Testosterone Replacement Therapy." Arch Intern Med., 149:2365-2366 (1989).
Jenster, G. et al., "Domains of the Human Androgen Receptor Involved in Steroid Binding, Transcriptional Activation, and Subcellular Localization." Molecular Endocrinology, 5:1396-1404 (1991).
Jenster, Guido, et al. "Identification of two transcription activation units in the N-terminal domain of the human androgen receptor." Journal of Biological Chemistry (1995); 270.13: 7341-7346.
Jin et al., "Total Synthesis of Sintokamide C." Organic Letters, 12(5): 1100-1103 (2010).
Kaighn, M.E. et al., "Prostate Carcinoma: Tissue Culture Cell Lines." National Cancer Institute Monograph, 49: 17-21 (1978).
Kim, D. et al., "Androgen Receptor Expression and Cellular Proliferation During Transition from Androgen-Dependent to Recurrent Growth after Castration in the CWR22 Prostate Cancer Xenograft." American Journal of Pathology, 160(1):219-226 (2002).
Kazlauskas et al., "A new sesquiterpene from the sponge Dysidea herbacea." Tetrahedron Letters, 19 (Issue 49): 4949-4950 (1978).
Kazlauskas et al., "Two sesquiterpene furans with new carbocyclic ring systems and related thiol acetates from a species of the sponge genus." Tetrahedron Letters, 19 (Issue 49): 4951-4954 (1978).
Kostochka, L.M. et al., "Synthesis, analgesic, and cerebrovascular activity of N-aminoacetyl derivatives of pyrollidone-2." Pharmaceutical Chemistry Journal, 23(4): 291-294 (1989).
Kricheldorf et al., "Mechanismus der NCA-Polymerisation, 4. Synthese and Reaktionen von N-Acyl-NCA." Die Makromolekulare Chemie, 178(4): 905-939 (1977).
Lu et al., "Three dolabellanes and a macrolide from the sponge Dysidea sp. from Palau." Journal of Natural Products, 61(9): 1096-1100 (1998).
Luesch et al., "Structurally diverse new alkaloids from Palauan collections of the apratoxinproducing marine cyanobacterium Lyngbya sp." Tetrahedron, 58: 7959-7966 (2002).
Miller, J.I. et al., "The Clinical Usefulness of Serum Prostate Specific Antigen After Hormonal Therapy of Metastatic Prostate Cancer." The Journal of Urology, 147:956-961 (1992).
Nazareth, L.V. et al, "Activation of the Human Androgen Receptor through a Protein Kinase A Signaling Pathway." The Journal of Biological Chemistry, 271(33):19900-19907 (1996).
Noble, R. L., "The development of prostatic adenocarcinoma in Nb Rats following prolonged sex hormone administration." Cancer Research, 37:1929-1933 (1977).
Noble, R. L., "Sex steroids as a cause of adenocarcinoma of the dorsal prostate in Nb Rats, and their influence on the growth of transplants." Oncology, 34:138-141 (1977).
Orjala et al., "Barbamide, a chlorinated metabolite with molluscicidal activity from the Caribbean cyanobacterium Lyngbya majuscula." Journal of Natural Products, 59(4): 427-430 (1996).
PCT/CA2009/001173, International Search Report and Written Opinion dated Dec. 7, 2009, 9 pages.
PCT/CA2009/001173, International Preliminary Report on Patentability dated Feb. 22, 2011, 7 pages.
PCT/US2015/033385, International Search Report and Written Opinion dated Aug. 28, 2015, 3 pages.
PCT/US2015/033385, International Preliminary Report on Patentability dated Dec. 6, 2016, 7 pages.
Quayle, S. et al., "Androgen receptor decoy molecules block the growth of prostate cancer." PNAS, 104(4):1331-1336 (2007).
Rao and Slotman, "Endocrine Factors in Common Epithelial Ovarian Cancer." Endocrine Reviews, 12(1):14-26 (1991).
Reid, J. et al., "Conformational Analysis of the Androgen Receptor Amino-terminal Domain Involved in Transactivation." The Journal of Biological Chemistry, 277:20079-20086 (2002).
Risch, H.A., "Hormonal Etiology of Epithelial Ovarian Cancer, With a Hypothesis Concerning the Role of Androgens and Progesterone." Journal of the National Cancer Institute, 90(23):1774-1786 (1998).
Roberts, J. T. et al., "Adenocarcinoma of Prostate in 40-Year-Old Body-Builder." Lancet, 2:742 (1986).
Ross, R.K. et al., "Androgen Metabolism and Prostate Cancer: Establishing a Model of Genetic Susceptibility." European Urology, 35:355-361 (1999).
Sadar, M., "Androgen-independent Induction of Prostate-specific Antigen Gene Expression via Cross-talk between the Androgen Receptor and Protein Kinase A signal Transduction Pathways." The Journal of Biological Chemistry, 274(12):7777-7783 (1999).
Sadar, M. et al., "Prostate cancer: molecular biology of early progression to androgen independence." Endocrine-Related Cancer, 6:487-502 (1999).

(56) References Cited

OTHER PUBLICATIONS

Sadar, M.D. et al., "Characterization of a New in Vivo Hollow Fiber Model for the Study of Progression of Prostate Cancer to Androgen Independence." Molecular Cancer Therapeutics, 1:629-637 (2002).

Sadar, et al., "Sintokamides A to E, Chlorinated Peptides from the Sponge *Dysidea* sp. that Inhibit Transactivation of the N-Terminus of the Androgen Receptor in Prostate Cancer Cells." Org. Letters, 10(21): 4947-4950 (2008).

Sato, N. et al., "Intermittent Androgen Suppression Delays Progression to Androgen-independent Regulation of Prostate-specific Antigen Gene in the LNCaP Prostate Tumour Model." J. Steroid Biochem. Mol. Biol., 58:139-146 (1996).

Sato, N. et al., "A Metastatic and Androgen-sensitive Human Prostate Cancer Model Using Intraprostatic Inoculation of LNCaP Cells in SCID Mice." Cancer Research, 57:1584-1589 (1997).

Simmons et al., "Belamide A, a new antimitotic tetrapeptide from a Panamanian marine cyanobacterium." Tetrahedron Letters, 47: 3387-3390 (2006).

Snoek, R. et al., "Induction of Cell-free, In Vitro Transcription by Recombinant Androgen Receptor Peptides." J. Steroid Biochem. Mol. Biol., 59:243-250 (1996).

Still, W. C. et al., "Rapid Chromatographic Technique for Preparative Separations with Moderate Resolution." J. Org. Chem., 43(14):2923-2925 (1978).

Su, Jing-Yu, et al. "Three new diketopiperazines from a marine sponge *Dysidea fragilis*." Journal of Natural Products, 56(4): 637-642 (1993).

Sun, S. et al., "Castration resistance in human prostate cancer is conferred by a frequently occurring androgen receptor splice variant." The Journal of Clinical Investigation, 120(8):2715-2730 (2010).

Tanji, N. et al., "Growth Factors: Rules in Andrology." Archives of Andrology, 47:1-7 (2001).

Taplin, M.E. et al., "Selection for Androgen Receptor Mutations in Prostate cancers Treated with Androgen Antagonist." Cancer Research, 59:2511-2515 (1999).

Thomson, A.A., "Role of androgens and fibroblast growth factors in prostatic development." Reproduction, 121:187-195 (2001).

Ueda, T. et al., "Activation of the Androgen Receptor N-terminal Domain by Interleukin-6 via MAPK and STAT3 Signal Transduction Pathways." The Journal of Biological Chemistry, 277(9):7076-7085 (2002).

Ueda, T. et al., "Ligand-independent Activation of the Androgen Receptor by Interleukin-6 and the Role of Steroid Receptor Coactivator-1 in Prostate cancer Cells." The Journal of Biological Chemistry, 277(41): 38087-38094(2002).

Unson, Mia D. et al. "New polychlorinated amino acid derivatives from the marine sponge *Dysidea herbacea*." The Journal of Organic Chemistry, 58(23): 6336-6343 (1993).

Van Der Kwast, T.H. et al., "Androgen Receptors in Endocrine-Therapy-Resistant Human Prostate Cancer." Inter. J. Cancer, 48:189-193 (1991).

Wilding, G., "The Importance of Steroid Hormones in Prostate Cancer." Cancer Surveys, 14:113-130 (1992).

Willard et al., "Total synthesis of (.+-.)-dysidin, a marine metabolite containing an N-acyl-O-methyltetramic acid." The Journal of Organic Chemistry, 49(19): 3489-3493 (1984).

Williams and Lemke, Faye's Principles of Medicinal Chemistry, Fifth Edition (14 Pages) (2002).

Wilson, J.D. et al., "Long-Term Consequences of Castration in Men: Lessons from the Skoptzy and the Eunuchs of the Chinese and Ottoman Courts." The Journal of Clinical Endocrinology & Metabolism, 84:4324-4331 (1999).

Zarantonello et al., "Total Synthesis and Semi-Synthetic Approaches to Analogues of Antibacterial Natural Product Althiomycin." Bioorg. Med. Chem. Lett., 2: 561-565 (2002).

\* cited by examiner

ANDROGEN RECEPTOR MODULATORS AND METHODS FOR THEIR USE

CROSS-REFERENCE TO RELATED APPLICATION

This application is a continuation of U.S. application Ser. No. 14/726,129, filed on May 29, 2015, now U.S. Pat. No. 9,682,933, which claims the benefit of U.S. Provisional Application No. 62/005,714, filed May 30, 2014, the disclosures of each of which are hereby incorporated by reference in their entirety for all purposes.

STATEMENT OF GOVERNMENT INTEREST

This invention was made in part with government support under Grant No. 2R01 CA105304 awarded by the National Cancer Institute. The United States Government has certain rights in this invention.

BACKGROUND

Technical Field

This invention generally relates to androgen receptor modulators and their use for treatment of various indications. In particular the invention relates to small molecule androgen receptor modulators and their use for treatment of various cancers, for example all stages of prostate cancer, including androgen dependent, androgen-sensitive and castration-resistant prostate cancers.

Description of the Related Art

Androgens mediate their effects through the androgen receptor (AR). Androgens play a role in a wide range of developmental and physiological responses and are involved in male sexual differentiation, maintenance of spermatogenesis, and male gonadotropin regulation (R. K. Ross, G. A. Coetzee, C. L. Pearce, J. K. Reichardt, P. Bretsky, L. N. Kolonel, B. E. Henderson, E. Lander, D. Altshuler & G. Daley, *Eur Urol* 35, 355-361 (1999); A. A. Thomson, *Reproduction* 121, 187-195 (2001); N. Tanji, K. Aoki & M. Yokoyama, *Arch Androl* 47, 1-7 (2001)). Several lines of evidence show that androgens are associated with the development of prostate carcinogenesis. Firstly, androgens induce prostatic carcinogenesis in rodent models (R. L. Noble, *Cancer Res* 37, 1929-1933 (1977); R. L. Noble, *Oncology* 34, 138-141 (1977)) and men receiving androgens in the form of anabolic steroids have a higher incidence of prostate cancer (J. T. Roberts & D. M. Essenhigh, *Lancet* 2, 742 (1986); J. A. Jackson, J. Waxman & A. M. Spiekerman, *Arch Intern Med* 149, 236 5-236 6 (1989); P. D. Guinan, W. Sadoughi, H. Alsheik, R. J. Ablin, D. Alrenga & I. M. Bush, *Am J Surg* 131, 599-6 00 (1976)). Secondly, prostate cancer does not develop if humans or dogs are castrated before puberty (J. D. Wilson & C. Roehrborn, *J Clin Endocrinol Metab* 84, 4324-4331 (1999); G. Wilding, *Cancer Surv* 14, 113-130 (1992)). Castration of adult males causes involution of the prostate and apoptosis of prostatic epithelium while eliciting no effect on other male external genitalia (E. M. Bruckheimer & N. Kyprianou, *Cell Tissue Res* 301, 153-16 2 (2000); J. T. Isaacs, *Prostate* 5, 545-557 (1984)). This dependency on androgens provides the underlying rationale for treating prostate cancer with chemical or surgical castration (androgen ablation).

Androgens also play a role in female cancers. One example is ovarian cancer where elevated levels of androgens are associated with an increased risk of developing ovarian cancer (K. J. Helzlsouer, A. J. Alberg, G. B. Gordon, C. Longcope, T. L. Bush, S. C. Hoffman & G. W. Comstock, *JAMA* 274, 1926-1930 (1995); R. J. Edmondson, J. M. Monaghan & B. R. Davies, *Br J Cancer* 86, 879-885 (2002)). androgen receptor (AR) has been detected in a majority of ovarian cancers (H. A. Risch, *J Natl Cancer Inst* 90, 1774-1786 (1998); B. R. Rao & B. J. Slotman, *Endocr Rev* 12, 14-26 (1991); G. M. Clinton & W. Hua, *Crit Rev Oncol Hematol* 25, 1-9 (1997)), whereas estrogen receptor-alpha (ERa) and the progesterone receptor are detected in less than 50% of ovarian tumors.

An effective treatment available for advanced prostate cancer is the withdrawal of androgens which are essential for the survival of prostate epithelial cells. Androgen ablation therapy causes a temporary reduction in tumor burden concomitant with a decrease in serum prostate-specific antigen (PSA). Unfortunately prostate cancer can eventually grow again in the absence of testicular androgens (castration-resistant disease) (Huber et al 1987 *Scand J. Urol Nephrol.* 104, 33-39). Castration-resistant prostate cancer is biochemically characterized before the onset of symptoms by a rising titre of serum PSA (Miller et al 1992 *J. Urol.* 147, 956-961). Once the disease becomes castration-resistant most patients succumb to their disease within two years.

The androgen receptor (AR) has distinct functional domains that include the carboxy-terminal ligand-binding domain (LBD), a DNA-binding domain (DBD) comprising two zinc finger motifs, and an N-terminus domain (NTD) that contains one or more transcriptional activation domains. Binding of androgen (ligand) to the LBD of androgen receptor (AR) results in its activation such that the receptor can effectively bind to its specific DNA consensus site, termed the androgen response element (ARE), on the promoter and enhancer regions of "normally" androgen regulated genes, such as PSA, to initiate transcription. Androgen receptor (AR) can be activated in the absence of androgen by stimulation of the cAMP-dependent protein kinase (PKA) pathway, with interleukin-6 (IL-6) and by various growth factors (Culig et al 1994 *Cancer Res.* 54, 5474-5478; Nazareth et al 1996 *J. Biol. Chem.* 271, 19900-19907; Sadar 1999 *J. Biol. Chem.* 274, 7777-7783; Ueda et al 2002 A *J. Biol. Chem.* 277, 7076-7085; and Ueda et al 2002 B *J. Biol. Chem.* 277, 38087-38094). The mechanism of ligand-independent transformation of androgen receptor (AR) has been shown to involve: 1) increased nuclear androgen receptor (AR) protein suggesting nuclear translocation; 2) increased androgen receptor (AR)/ARE complex formation; and 3) the androgen receptor (AR)-NTD (Sadar 1999 *J. Biol. Chem.* 274, 7777-7783; Ueda et al 2002 A *J Biol. Chem.* 277, 7076-7085; and Ueda et al 2002 B *J. Biol. Chem.* 277, 38087-38094). The androgen receptor (AR) may be activated in the absence of testicular androgens by alternative signal transduction pathways in castration-resistant disease, which is consistent with the finding that nuclear androgen receptor (AR) protein is present in secondary prostate cancer tumors (Kim et al 2002 *Am. J. Pathol.* 16 0, 219-226; and van der Kwast et al 1991 *Inter. J. Cancer* 48, 189-193).

Available inhibitors of androgen receptor (AR) include nonsteroidal antiandrogens such as bicalutamide, nilutamide, flutamide, enzalutamide, and investigational drugs ARN-509 and ODM-201, and the steroidal antiandrogen, cyproterone acetate. These antiandrogens target the LBD of androgen receptor (AR) and predominantly fail presumably due to poor affinity and mutations that lead to activation of androgen receptor (AR) by these same antiandrogens (Taplin, M. E., Bubley, G. J., Kom Y. J., Small E. J., Uptonm M., Rajeshkumarm B., Balkm S. P., *Cancer Res.*, 59, 2511-2515 (1999)). These antiandrogens would also have no effect on the recently discovered androgen receptor (AR) splice variants that lack the ligand-binding domain (LBD) to result in a constitutively active receptor which promotes progression of androgen-independent prostate cancer (Dehm S M, Schmidt L J, Heemers H V, Vessella R L, Tindall D J., *Cancer Res* 6 8, 546 9-77, 2008; Guo Z, Yang X, Sun F, Jiang R, Linn D E, Chen H, Chen H, Kong X, Melamed J, Tepper C G, Kung H J, Brodie A M, Edwards J, Qiu Y., *Cancer Res.* 6 9, 2305-13, 2009; Hu et al 2009 Cancer Res. 6 9, 16-22; Sun et al 2010 J Clin Invest. 2010 120, 2715-30).

Recent studies developing antagonists to the androgen receptor (AR) have concentrated on the C-terminal domain and specifically: 1) the allosteric pocket and AF-2 activity (Estébanez-Perpiñá et al 2007, *PNAS* 104, 16 074-16 079); 2) in silico "drug repurposing" procedure for identification of nonsteroidal antagonists (Bisson et al 2007, *PNAS* 104, 11927-11932); and coactivator or corepressor interactions (Chang et al 2005, *Mol Endocrinology* 19, 2478-2490; Hur et al 2004, *PLoS Biol* 2, E274; Estébanez-Perpiñá et al 2005, *JBC* 280, 806 0-806 8; He et al 2004, *Mol Cell* 16, 425-438).

The androgen receptor (AR)-NTD is also a target for drug development (e.g. WO 2000/001813), since the NTD contains Activation-Function-1 (AF-1) which is the essential region required for AR transcriptional activity (Jenster et al 1991. Mol Endocrinol. 5, 1396-404). The AR-NTD importantly plays a role in activation of androgen receptor (AR) in the absence of androgens (Sadar, M. D. 1999 *J. Biol. Chem.* 274, 7777-7783; Sadar M D et al 1999 *Endocr Relat Cancer.* 6, 487-502; Ueda et al 2002 *J. Biol. Chem.* 277, 7076-7085; Ueda 2002 *J. Biol. Chem.* 277, 38087-38094; Blaszczyk et al 2004 *Clin Cancer Res.* 10, 186 0-9; Dehm et al 2006 *J Biol Chem.* 28, 27882-93; Gregory et al 2004 *J Biol Chem.* 279, 7119-30). The androgen receptor (AR)-NTD is important in hormonal progression of prostate cancer as shown by application of decoy molecules (Quayle et al 2007, *Proc Natl Acad Sci USA.* 104, 1331-1336).

While the crystal structure has been resolved for the androgen receptor (AR) C-terminus LBD, this has not been the case for the NTD due to its high flexibility and intrinsic disorder in solution (Reid et al 2002 *J. Biol. Chem.* 277, 20079-20086) thereby hampering virtual docking drug discovery approaches.

Although progress has been made, there remains a need in the art for additional and/or improved compounds that modulate androgen receptor (AR). The present disclosure provides these and related advantages.

BRIEF SUMMARY

This invention is based in part on the unexpected discovery that certain Sintokamide-related compounds have desirable properties for use as modulators of androgen receptor (AR). In particular, the compounds described herein are potent modulators of androgen receptor (AR). In accordance with one embodiment, there is provided a compound having a structure of Structure I:

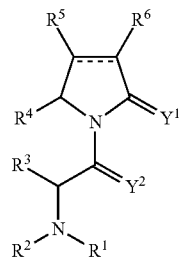

or a pharmaceutically acceptable salt, tautomer or stereoisomer thereof, wherein $R^1$, $R^2$, $R^3$, $R^4$, $R^5$, $R^6$, $Y^1$ and $Y^2$ are as defined herein, and wherein at least one of $R^3$ or $R^4$ is a straight-chain $C_1$-$C_6$ haloalkyl. Pharmaceutical compositions comprising a compound of Structure I, a pharmaceutically acceptable carrier and an optional additional therapeutic agent are also provided.

In other embodiments, the present disclosure provides the use of a compound of Structure I or a composition comprising the same, for modulating androgen receptor (AR) activity. Related methods for modulating androgen receptor (AR) are also provided.

These and other aspects of the invention will be apparent upon reference to the following detailed description. To this end, various references are set forth herein which describe in more detail certain background information, procedures, compounds and/or compositions, and are each hereby incorporated by reference in their entirety.

BRIEF DESCRIPTION OF THE DRAWINGS

In the figures, identical reference numbers identify similar elements. The sizes and relative positions of elements in the figures are not necessarily drawn to scale and some of these elements are arbitrarily enlarged and positioned to improve figure legibility. Further, the particular shapes of the elements as drawn are not intended to convey any information regarding the actual shape of the particular elements, and have been solely selected for ease of recognition in the figures.

DETAILED DESCRIPTION

I. Definitions

Figure 1:
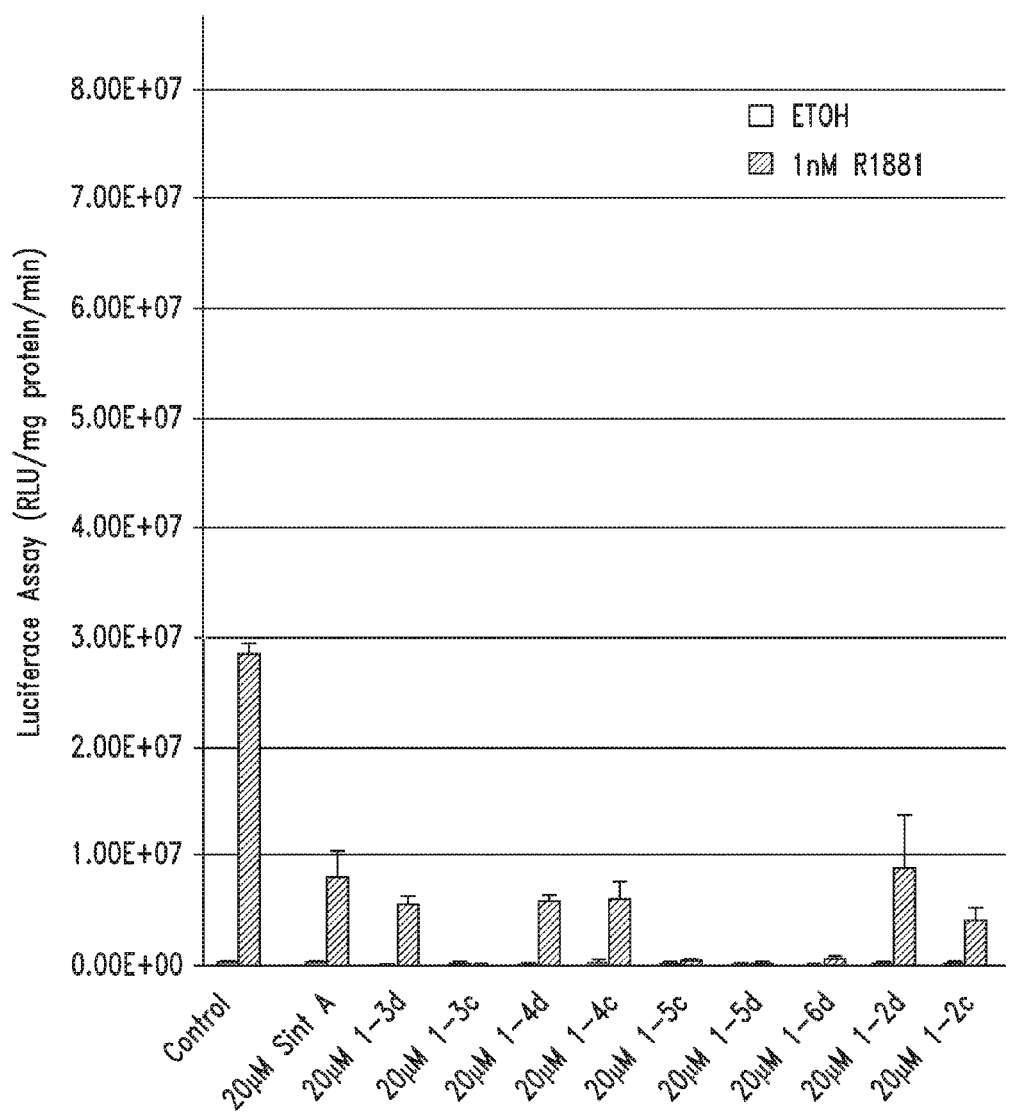
FIG. 1 presents R1881 activation data for exemplary compounds and Sintokamide A.

In the following description, certain specific details are set forth in order to provide a thorough understanding of various embodiments. However, one skilled in the art will understand that the invention may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed invention.

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments. Also, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The terms below, as used herein, have the following meanings, unless indicated otherwise:

"Amino" refers to the —$NH_2$ radical.

"Cyano" refers to the —CN radical.

"Hydroxy" or "hydroxyl" refers to the —OH radical.

"Imino" refers to the =NH substituent.

"Nitro" refers to the —$NO_2$ radical.

"Oxo" refers to the =O substituent.

"Thioxo" refers to the =S substituent.

"Alkyl" refers to a straight or branched hydrocarbon chain radical which is saturated or unsaturated (i.e., contains one or more double and/or triple bonds), having from one to twenty carbon atoms (e.g., one to ten, or one to six carbon atoms), and which is attached to the rest of the molecule by a single bond. Alkyls comprising any number of carbon atoms from 1 to 20 are included. An alkyl comprising up to 6 carbon atoms is a $C_1$-$C_6$ alkyl. A $C_1$-$C_6$ alkyl includes $C_6$ alkyls, $C_5$ alkyls, $C_4$ alkyls, $C_3$ alkyls, $C_2$ alkyls and $C_1$ alkyl (i.e., methyl) and includes, for example, and without limitation, saturated $C_1$-$C_6$ alkyl, $C_2$-$C_6$ alkenyl (contains at least one carbon-carbon double bond) and $C_2$-$C_6$ alkynyl (contains at least one carbon-carbon triple bond). Non-limiting examples of saturated $C_1$-$C_6$ alkyl include methyl, ethyl, n-propyl, i-propyl, sec-propyl, n-butyl, i-butyl, sec-butyl, t-butyl and n-pentyl, n-hexyl, and the like. Non-limiting examples of $C_2$-$C_6$ alkenyl include vinyl, allyl, isopropenyl, 1-propene-2-yl, 1-butene-1-yl, 1-butene-2-yl, 1-butene-3-yl, 2-butene-1-yl, 2-butene-2-yl, penteneyl, hexeneyl, and the like. Non-limiting examples of $C_2$-$C_6$ alkynyl include ethynyl, propynyl, butynyl, pentynyl, hexynyl, and the like. Unless stated otherwise specifically in the specification, an alkyl group may be optionally substituted (i.e., a hydrogen atom in the alkyl group may be replaced with an optional substituent).

"Alkylene" or "alkylene chain" refers to a straight or branched divalent hydrocarbon chain linking the rest of the molecule to a radical group, consisting solely of carbon and hydrogen, which is saturated or unsaturated (i.e., contains one or more double and/or triple bonds), and having from one to twenty carbon atoms, e.g., methylene, ethylene, propylene, n-butylene, ethenylene, propenylene, n-butenylene, propynylene, n-butynylene, and the like. The alkylene chain is attached to the rest of the molecule through a single or double bond and to the radical group through a single or double bond. The points of attachment of the alkylene chain to the rest of the molecule and to the radical group can be through one carbon or any two carbons within the chain. Unless stated otherwise specifically in the specification, an alkylene chain may be optionally substituted.

"Aliphatic carbon" refers to a carbon atom which is not aromatic.

"Alkylaminocarbonyl" refers to a radical of the formula —C(=O)$NR_aR_b$ where $R_a$ and $R_b$ are each independently an alkyl radical as defined above containing one to twenty carbon atoms. Unless stated otherwise specifically in the specification, an alkylaminocarbonyl group may be optionally substituted.

"Alkylcarbonyl" refers to a radical of the formula —C(=O)$R_a$ where $R_a$ is an alkyl radical as defined above containing one to twenty carbon atoms. Unless stated otherwise specifically in the specification, an alkylcarbonyl group may be optionally substituted.

"Alkoxy" refers to a radical of the formula —$OR_a$ where $R_a$ is an alkyl radical as defined above containing one to twenty carbon atoms, for example one to six carbon atoms. Unless stated otherwise specifically in the specification, an alkoxy group may be optionally substituted.

"Alkylamino" refers to a radical of the formula —$NHR_a$ or —$NR_aR_a$ where each $R_a$ is, independently, an alkyl radical as defined above containing one to twenty carbon atoms. Unless stated otherwise specifically in the specification, an alkylamino group may be optionally substituted.

"Aminocarbonyl" refers to a radical of the formula —C(=O)$NH_2$. Unless stated otherwise specifically in the specification, an alkylcarbonyl group may be optionally substituted.

"Aromatic carbon" refers to a carbon atom which is part of an aromatic ring. Aromatic carbons are $SP^2$ hybridized and from part of a conjugated, unsaturated ring system having 4n+2 electrons in pi orbitals. For example, aromatic carbons may be members on an aryl or heteroaryl ring as defined herein.

"Aryl" refers to a hydrocarbon ring system radical comprising hydrogen, 6 to 18 carbon atoms and at least one aromatic ring. For purposes of this invention, the aryl radical may be a monocyclic, bicyclic, tricyclic or tetracyclic ring system, which may include fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the term "aryl" or the prefix "ar-" (such as in "aralkyl") is meant to include aryl radicals that are optionally substituted.

"Aralkyl" refers to a radical of the formula —$R_b$—$R_c$ where $R_b$ is an alkylene chain as defined above and $R_c$ is one or more aryl radicals as defined above, for example, benzyl, diphenylmethyl and the like. Unless stated otherwise specifically in the specification, an aralkyl group may be optionally substituted.

"Carbocycle" refers to a cyclic structure, wherein the bonds that form the ring are each carbon-carbon bonds. Carbocycles generally contain from 3 to 20 carbon atoms within the ring and may be mon, bi or tri-cyclic. Bi and tricyclic carbocycles may be fused (i.e., share two or more common carbon atoms), spiro (i.e., share one common carbon atom) or linked via a linker atom or atoms. Carbocycles, include cycloalkyls and aryls as defined herein. Unless stated otherwise specifically in the specification, carbocycle group may be optionally substituted.

"Cycloalkyl" refers to a stable non-aromatic monocyclic or polycyclic hydrocarbon radical consisting solely of carbon and hydrogen atoms, which may include fused or bridged ring systems, having from three to fifteen carbon atoms, preferably having from three to ten carbon atoms, and which is saturated or unsaturated and attached to the rest of the molecule by a single bond. Monocyclic radicals include, for example, cyclopropyl, cyclobutyl, cyclopentyl, cyclohexyl, cycloheptyl, and cyclooctyl. Polycyclic radicals include, for example, adamantyl, norbornyl, decalinyl, 7,7-dimethyl-bicyclo[2.2.1]heptanyl, and the like. Unless otherwise stated specifically in the specification, a cycloalkyl group may be optionally substituted.

"Fused" refers to any ring structure described herein which is fused to an existing ring structure in the compounds of the invention. When the fused ring is a heterocyclyl ring or a heteroaryl ring, any carbon atom on the existing ring structure which becomes part of the fused heterocyclyl ring or the fused heteroaryl ring may be replaced with a nitrogen atom.

"Halogen" or "halo" refers to fluoro (F), chloro (Cl), bromo (Br) and iodo (I) substituents.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1,2-difluoroethyl, 3-bromo-2-fluoropropyl, 1,2-dibromoethyl, and the like. A haloalkyl may be straight-chain or branched, and unless otherwise specified both straight-chain and branched haloalkyls are included. A "Chloroalkyl" is a haloalkyl comprising at least one chloro substituent. "Perhalo" (e.g., "perchloro") refers to a carbon atom which is bound only to other carbon atom(s) and halogen atom(s) (i.e., no hydrogen substituents). Unless stated otherwise specifically in the specification, a haloalkyl group is optionally substituted.

"Haloalkoxy" refers to an alkoxy radical, as defined above, that is substituted by one or more halo radicals, as defined above, e.g., trifluoromethoxy, difluoromethoxy, trichloromethoxy, 2,2,2-trifluoroethoxy, 1,2-difluoroethoxy, 3-bromo-2-fluoropropoxy, 1,2-dibromoethoxy, and the like. A haloalkoxy may be straight-chain or branched, and unless otherwise specified both straight-chain and branched haloalkoxys are included. Unless stated otherwise specifically in the specification, a haloalkoxy group is optionally substituted.

"Heterocyclyl" or "heterocyclic ring" refers to a stable 3- to 18-membered ring radical which consists of two to twelve carbon atoms and from one to six heteroatoms selected from the group consisting of nitrogen, oxygen and sulfur. Unless stated otherwise specifically in the specification, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, a heterocyclyl group may be optionally substituted. Heterocycles include heteroaryls as defined below.

"Heteroaryl" refers to a 5- to 14-membered ring system radical comprising hydrogen atoms, one to thirteen carbon atoms, one to six heteroatoms selected from the group consisting of nitrogen, oxygen and sulfur, and at least one aromatic ring. For purposes of this invention, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e. thienyl). Unless stated otherwise specifically in the specification, a heteroaryl group may be optionally substituted.

The term "substituted" used herein means any of the above groups (e.g., alkyl, haloalkyl, haloalkoxy, alkylene, alkylaminocarbonyl, alkylcarbonyl, alkoxy, alkylamino, aminocarbonyl, cycloalkyl, aryl, aralkyl, carbocycle, deuteroalkyl, haloalkyl, heterocyclyl, and/or heteroaryl) wherein at least one hydrogen atom is replaced by a bond to a non-hydrogen atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo (i.e., C=O), carbonyl, carboxyl, and ester groups; and nitrogen in groups such as imines, oximes, hydrazones, and nitriles. For example, "substituted" includes any of the above groups in which one or more hydrogen atoms are replaced with $-NR_gR_h$, $-NR_gC(=O)R_h$, $-NR_gC(=O)NR_gR_h$, $-NR_gC(=O)OR_h$, $-NR_gSO_2R_h$, $-OC(=O)NR_gR_h$, $-OR_g$, $-SR_g$, $-SOR_g$, $-SO_2R_g$, $-OSO_2R_g$, $-SO_2OR_g$, $=NSO_2R_g$, and $-SO_2NR_gR_h$. "Substituted also means any of the above groups in which one or more hydrogen atoms are replaced with $-C(=O)R_g$, $-C(=O)OR_g$, $-C(=O)NR_gR_h$, $-CH_2SO_2R_g$, $-CH_2SO_2NR_gR_h$. In the foregoing, $R_g$ and $R_h$ are the same or different and independently hydrogen, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an amino, cyano, hydroxyl, imino, nitro, oxo, thioxo, halo, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl group. In addition, each of the foregoing substituents may also be optionally substituted with one or more of the above substituents.

"Prodrug" is meant to indicate a compound that may be converted under physiological conditions or by solvolysis to a biologically active compound. Thus, the term "prodrug" refers to a metabolic precursor of a compound of the invention that is pharmaceutically acceptable. A prodrug may be active or inactive when administered to a subject in need thereof, but is converted in vivo to an active (or more active) compound. Prodrugs are typically rapidly transformed in vivo to yield the parent compound, for example, by hydrolysis in blood. The prodrug compound often offers advantages of solubility, tissue compatibility or delayed release in a mammalian organism (see, Bundgard, H., Design of Prodrugs (1985), pp. 7-9, 21-24 (Elsevier, Amsterdam)). A discussion of prodrugs is provided in Higuchi, T., et al., A.C.S. Symposium Series, Vol. 14, and in Bioreversible Carriers in Drug Design, Ed. Edward B. Roche, American Pharmaceutical Association and Pergamon Press, 1987. The present invention is meant to encompass all compounds of structure I, whether acting as a prodrug or the active compound itself, or both.

The invention disclosed herein is also meant to encompass all pharmaceutically acceptable compounds of Structure (I) being isotopically-labelled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine, chlorine, and iodine, such as $^2H$, $^3H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. These radiolabelled compounds could be useful to help determine or measure the effectiveness of the compounds, by characterizing, for example, the site or mode of action, or binding affinity to pharmacologically important site of action. Certain isotopically-labelled compounds of Structure (I), for example, those incorporating a radioactive isotope, are useful in drug and/or substrate tissue distribution studies. The radioactive isotopes tritium, i.e. $^3H$, and carbon-14, i.e. $^{14}C$, are particularly useful for this purpose in view of their ease of incorporation and ready means of detection.

Substitution with heavier isotopes such as deuterium, i.e. $^2H$, may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Topography (PET) studies for examining substrate receptor occupancy. Substitution with $I^{123}$ can produce compounds useful for single photon emission computed tomography (SPECT) imaging. Isotopically-labeled compounds of Structure (I) can generally be prepared by conventional techniques known to those skilled in the art or by processes analogous to those described in the Preparations and Examples as set out below using an appropriate isotopically-labeled reagent in place of the non-labeled reagent previously employed.

The invention disclosed herein is also meant to encompass the in vivo metabolic products of the disclosed compounds. Such products may result from, for example, the oxidation, reduction, hydrolysis, amidation, esterification, and the like of the administered compound, primarily due to enzymatic processes. Accordingly, the invention includes compounds produced by a process comprising administering a compound of this invention to a mammal for a period of time sufficient to yield a metabolic product thereof. Such products are typically identified by administering a radiolabelled compound of the invention in a detectable dose to an animal, such as rat, mouse, guinea pig, monkey, or to human, allowing sufficient time for metabolism to occur, and isolating its conversion products from the urine, blood or other biological samples.

"Stable compound" and "stable structure" are meant to indicate a compound that is sufficiently robust to survive isolation to a useful degree of purity from a reaction mixture, and formulation into an efficacious therapeutic agent.

"Mammal" includes humans and both domestic animals such as laboratory animals and household pets (e.g., cats, dogs, swine, cattle, sheep, goats, horses, rabbits), and non-domestic animals such as wildlife and the like.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Often crystallizations produce a solvate of the compound of the invention. As used herein, the term "solvate" refers to an aggregate that comprises one or more molecules of a compound of the invention with one or more molecules of solvent. The solvent may be water, in which case the solvate may be a hydrate. Alternatively, the solvent may be an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. The compound of the invention may be true solvates, while in other cases, the compound of the invention may merely retain adventitious water or be a mixture of water plus some adventitious solvent.

A "pharmaceutical composition" refers to a formulation of a compound of the invention and a medium generally accepted in the art for the delivery of the biologically active compound to mammals, e.g., humans. Such a medium includes all pharmaceutically acceptable carriers, diluents or excipients therefor.

An "effective amount" refers to a therapeutically effective amount or a prophylactically effective amount. A "therapeutically effective amount" refers to an amount effective, at dosages and for periods of time necessary, to achieve the desired therapeutic result, such as reduced tumor size, increased life span or increased life expectancy. A therapeutically effective amount of a compound may vary according to factors such as the disease state, age, sex, and weight of the subject, and the ability of the compound to elicit a desired response in the subject. Dosage regimens may be adjusted to provide the optimum therapeutic response. A therapeutically effective amount is also one in which any toxic or detrimental effects of the compound are outweighed by the therapeutically beneficial effects. A "prophylactically effective amount" refers to an amount effective, at dosages and for periods of time necessary, to achieve the desired prophylactic result, such as smaller tumors, increased life span, increased life expectancy or prevention of the progression of prostate cancer to CRPC. Typically, a prophylactic dose is used in subjects prior to or at an earlier stage of disease, so that a prophylactically effective amount may be less than a therapeutically effective amount.

"Treating" or "treatment" as used herein covers the treatment of the disease or condition of interest in a mammal, preferably a human, having the disease or condition of interest, and includes:

(i) preventing the disease or condition from occurring in a mammal, in particular, when such mammal is predisposed to the condition but has not yet been diagnosed as having it;

(ii) inhibiting the disease or condition, i.e., arresting its development;

(iii) relieving the disease or condition, i.e., causing regression of the disease or condition; or (iv) relieving the symptoms resulting from the disease or condition, i.e., relieving pain without addressing the underlying disease or condition. As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

The compounds of the invention, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centres of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposeable mirror images of one another.

A "tautomer" refers to a proton shift from one atom of a molecule to another atom of the same molecule accompanied by a switch of a single bond and adjacent double bond. The present invention includes tautomers of any said compounds.

For complex chemical names employed herein, a substituent group is named before the group to which it attaches. For example, cyclopropylethyl comprises an ethyl backbone with cyclopropyl substituent. Except as described below, all bonds are identified in the chemical structure diagrams herein, except for some carbon atoms, which are assumed to be bonded to sufficient hydrogen atoms to complete the valency.

As used herein, the symbol

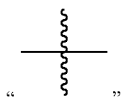

(hereinafter may be referred to as "a point of attachment bond") denotes a bond that is a point of attachment between two chemical entities, one of which is depicted as being attached to the point of attachment bond and the other of which is not depicted as being attached to the point of attachment bond. For example,

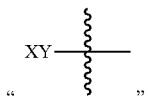
" "

indicates that the chemical entity "XY" is bonded to another chemical entity via the point of attachment bond. Furthermore, the specific point of attachment to the non-depicted chemical entity may be specified by inference. For example, the compound $CH_3$—$R^3$, wherein $R^3$ is H or

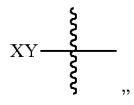
"

infers that when $R^3$ is "XY", the point of attachment bond is the same bond as the bond by which $R^3$ is depicted as being bonded to $CH_3$.

II. Compounds and Compositions

As noted above, certain embodiments of the present invention are directed to compounds useful for modulation of androgen receptor (AR). As such, the compounds find utility for treatment of various cancers, including various types of prostate cancers. The compounds described herein have improved properties relative to other known androgen receptor (AR) modulators, such as previously known Sintokamide compounds.

Accordingly, one embodiment of the present invention is directed to a compound having a structure of Structure I:

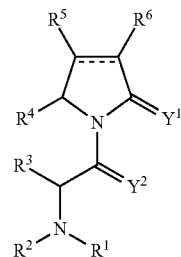
I or a pharmaceutically acceptable salt, tautomer or stereoisomer thereof, wherein:

$Y^1$ and $Y^2$ are each independently O or S;
$R^1$ is H, $C_1$-$C_6$ alkyl or $C_1$-$C_6$ haloalkyl;
$R^2$ is H, —C(=O)$R^7$ or —S(O)$_n$$R^8$;
at least one of $R^3$ or $R^4$ is a straight-chain $C_1$-$C_6$ haloalkyl, and the other one of $R^3$ or $R^4$ is $C_1$-$C_6$ alkyl or $C_1$-$C_6$ haloalkyl;
$R^5$ and $R^6$ are each independently H, OH, $C_1$-$C_6$ alkyl, $C_1$-$C_6$ alkoxy, $C_1$-$C_6$ haloalkyl or $C_1$-$C_6$ haloalkoxy;

$R^7$ is $C_1$-$C_6$ alkyl, $C_1$-$C_6$ alkoxy, $C_1$-$C_6$ haloalkyl or $C_1$-$C_6$ haloalkoxy;
$R^8$ is $C_1$-$C_6$ alkyl or $C_1$-$C_6$ haloalkyl;
═══ is a carbon-carbon double bond or a carbon-carbon single bond, such that all valences are satisfied; and
n is 0, 1 or 2.

It is understood that "straight chain haloalkyl" refers to an unbranched alkyl (e.g. n-propyl, n-butyl, n-pentyl, and the like) comprising at least one halogen substituent.

All possible stereoisomers are included within the scope of different embodiments of the invention. Accordingly, in some embodiments the compound has one of the following structures (Ia), (Ib), (Ic) or (Id):

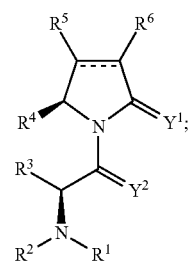
(Ia)

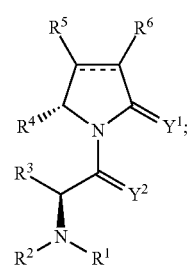
(Ib)

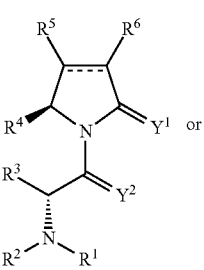
(Ic) or

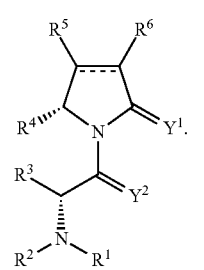
(Id)

In some embodiments, the compound has structure (Ia). In some other embodiments, the compound has structure (Ib). In different embodiments, the compound has structure (Ic). In some more embodiments, the compound has structure (Id).

In any of the foregoing embodiments, $Y^1$ is O. In other embodiments $Y^2$ is O. For example, in certain embodiments, both $Y^1$ and $Y^2$ are O.

In some other embodiments, $Y^1$ is S. In different embodiments $Y^2$ is S. For example, in certain embodiments, both $Y^1$ and $Y^2$ are S.

In other embodiments, $Y^1$ is O and $Y^2$ is S. In even more embodiments, $Y^1$ is S and $Y^2$ is O.

In some embodiments, $R^1$ is H. In other embodiments, $R^1$ is $C_1$-$C_6$ alkyl. In other different embodiments, $R^1$ is $C_1$-$C_6$ haloalkyl In some other of any of the foregoing embodiments, $R^2$ is H. For example in certain embodiments both $R^1$ and $R^2$ are H.

In other of the foregoing embodiments, $R^2$ is —C(=O)$R^7$. In some of the embodiments, $R^7$ is $C_1$-$C_6$ alkyl. For example in some embodiments the $C_1$-$C_6$ alkyl is saturated and in other embodiments the $C_1$-$C_6$ alkyl is unsaturated. In other embodiments, the $C_1$-$C_6$ alkyl is unsubstituted, and in different embodiments the $C_1$-$C_6$ alkyl is substituted. Specific examples of various different embodiments of $R^7$ $C_1$-$C_6$ alkyl moieties include, but are not limited to, ethyl, t-butyl or

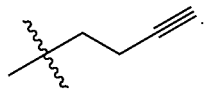 [SMILES: *CCC#C]

In other embodiments, $R^2$ is —C(=O)$R^7$ and $R^7$ is $C_1$-$C_6$ alkoxy. For example, the $C_1$-$C_6$ alkoxy may be substituted or unsubstituted. In various specific embodiments, the $C_1$-$C_6$ alkoxy is t-butoxy.

In other different embodiments, $R^2$ is —C(=O)$R^7$ and $R^7$ is $C_1$-$C_6$ haloalkyl. In yet more embodiments, $R^2$ is —C(=O)$R^7$ and $R^7$ is $C_1$-$C_6$ haloalkoxy.

In different embodiments, $R^2$ is —S(O)$_n$$R^8$. In some of these embodiments, $R^8$ is $C_1$-$C_6$ alkyl. In other embodiments, the $C_1$-$C_6$ alkyl is unsubstituted, and in different embodiments the $C_1$-$C_6$ alkyl is substituted. In some more specific embodiments, $R^8$ is ethyl. In yet further embodiments, n is 2.

In still more embodiments of any of the foregoing compounds, $R^5$ is $C_1$-$C_6$ alkoxy or $C_1$-$C_6$ haloalkoxy. In still more embodiments of any of the foregoing compounds, $R^5$ is $C_1$-$C_6$ alkoxy, such as methoxy. In other embodiments, $R^6$ is H. For example, in some embodiments $R^5$ is $C_1$-$C_6$ alkoxy, such as methoxy, and $R^6$ is H. In some other embodiments $R^5$ is OH, and $R^6$ is H.

In more embodiments of the foregoing, $R^3$ is a straight-chain $C_1$-$C_6$ haloalkyl, such as 3,3,3-trichloropropyl, and $R^4$ is $C_1$-$C_6$ alkyl or $C_1$-$C_6$ haloalkyl. In some of these embodiments, $R^4$ is $C_1$-$C_6$ haloalkyl. In some other of these embodiments, $R^4$ is a branched $C_1$-$C_6$ alkyl such as 2-methylpropyl. In some other of these embodiments, $R^4$ is a branched $C_1$-$C_6$ haloalkyl. In other embodiments, $R^4$ is a straight-chain $C_1$-$C_6$ haloalkyl, such as 3,3,3-trichloropropyl.

In more embodiments of the foregoing, $R^4$ is a straight-chain $C_1$-$C_6$ haloalkyl, such as 3,3,3-trichloropropyl, and $R^3$ is $C_1$-$C_6$ alkyl or $C_1$-$C_6$ haloalkyl. In some other of these embodiments, $R^3$ is a branched $C_1$-$C_6$ alkyl such as 2-methylpropyl. In some of these embodiments, $R^3$ is $C_1$-$C_6$ haloalkyl. In some other of these embodiments, $R^3$ is a branched $C_1$-$C_6$ haloalkyl. In other embodiments, $R^3$ is a straight-chain $C_1$-$C_6$ haloalkyl, such as 3,3,3-trichloropropyl.

In still more embodiments, at least one of $R^3$ or $R^4$ is a straight-chain $C_1$-$C_6$ chloroalkyl, and the other one of $R^3$ or $R^4$ is $C_1$-$C_6$ chloroalkyl. For example, in some embodiments the $C_1$-$C_6$ chloroalkyl comprises a perchloro-substituted carbon. In even further embodiments, $R^3$ or $R^4$, or both, is 3,3,3-trichloropropyl. In other embodiments, one of $R^3$ or $R^4$ is 3,3,3-trichloropropyl and the other of $R^3$ or $R^4$ is 3,3-dichloropropyl.

In some of any of the foregoing embodiments, ═══ is a carbon-carbon double bond. In other of any of the foregoing embodiments, ═══ is a carbon-carbon single bond.

The compounds described herein are meant to include all racemic mixtures and all individual enantiomers or combinations thereof, whether or not they are specifically depicted herein. Accordingly, the compounds include racemic mixtures, enantiomers and diastereomers of any of the compounds described herein. Tautomers of any of the compounds of Structure I are also included within the scope of the invention.

As noted above, the compounds of the present invention (i.e., compounds of Structure 1) may contain one or more asymmetric centers. Accordingly, in some embodiments the compounds are mixtures of different enantiomers (e.g., R and S) or different diastereomers. In other embodiments, the compounds are pure (or enriched) enantiomers or diastereomers. For purpose of clarity, the chiral carbons are not always depicted in the compounds; however, the present invention includes all stereoisomers (pure and mixtures) of all compounds of Structure I.

By way of example, compounds of Structure I contain at least two stereocenters marked with an * below:

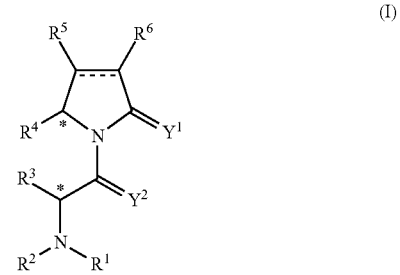

(I)

Although the compounds are generally depicted as above, the scope of the invention includes all possible stereoisomers. For example, with respect to Structure I, the invention also includes the following stereoisomers (Ia), (Ib), (Ic) and (Id):

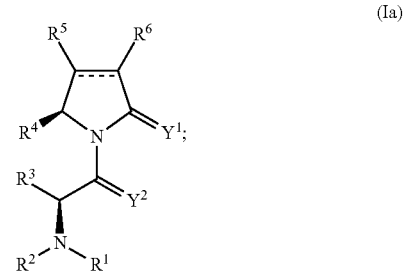

(Ia)

-continued
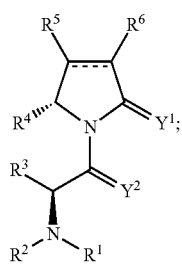
(Ib)
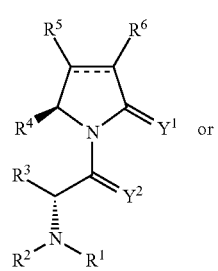
(Ic) or
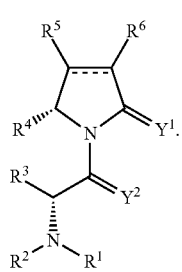
(Id)
In other particular embodiments of the compounds as described anywhere herein, the following compounds in Table 1 are provided.
TABLE 1
| Representative Compounds | |
|---|---|
| No. | Structure |
| 1-1 | 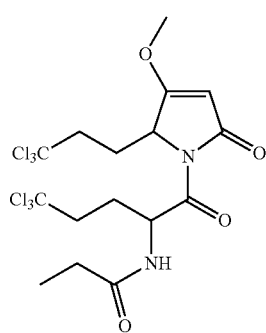 |
TABLE 1-continued
| Representative Compounds | |
|---|---|
| No. | Structure |
| 1-1a | 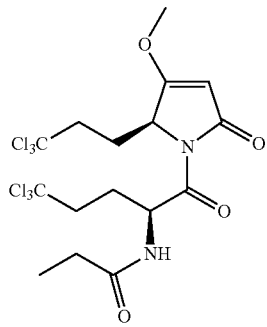 |
| 1-1b | 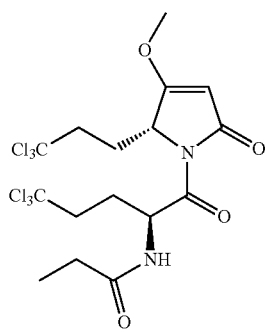 |
| 1-1c | 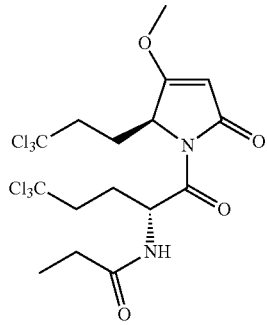 |
| 1-1d | 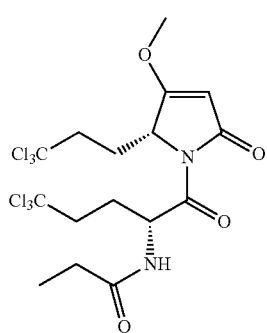 |

TABLE 1-continued

Representative Compounds

| No. | Structure |
|---|---|
| 1-2 | (structure) |
| 1-2a | (structure) |
| 1-2b | (structure) |
| 1-2c | (structure) |
| 1-2d | (structure) |
| 1-3 | (structure) |
| 1-3a | (structure) |
| 1-3b | (structure) |

TABLE 1-continued

Representative Compounds

| No. | Structure |
|---|---|
| 1-3c | 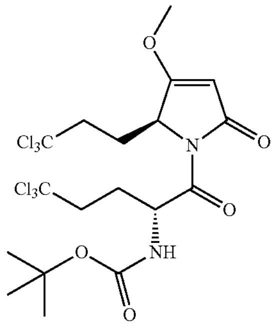 |
| 1-3d | 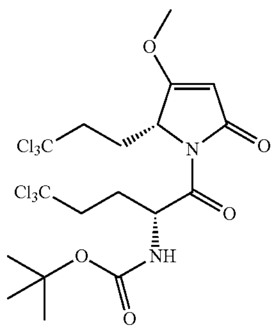 |
| 1-4 | 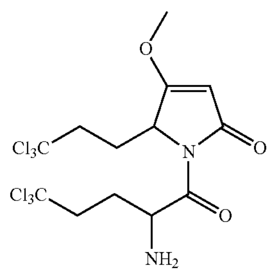 |
| 1-4a | 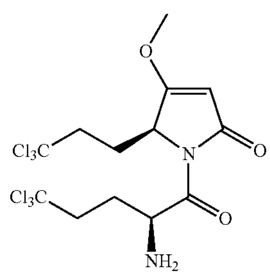 |
| 1-4b | 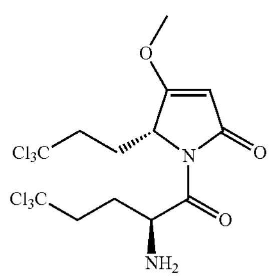 |
| 1-4c | 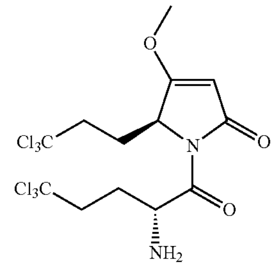 |
| 1-4d | 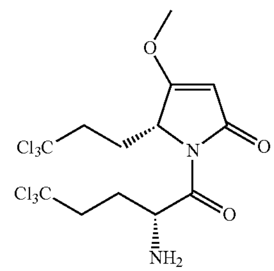 |
| 1-5 | 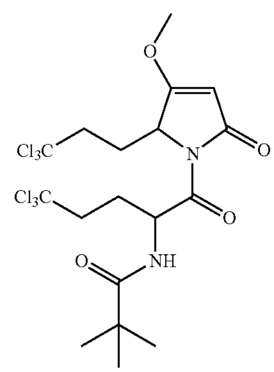 |
| 1-5a | 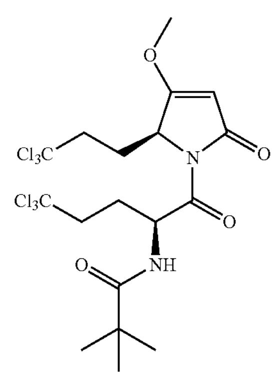 |

TABLE 1-continued

Representative Compounds

| No. | Structure |
|---|---|
| 1-5b | 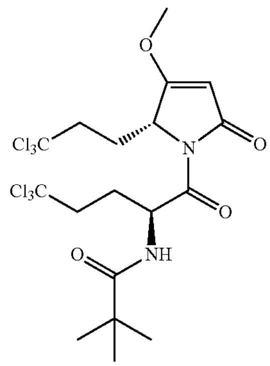 |
| 1-5c | 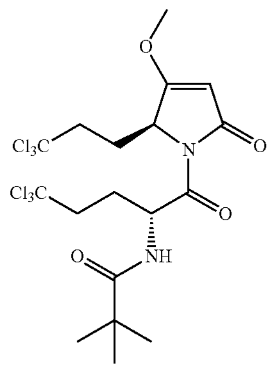 |
| 1-5d | 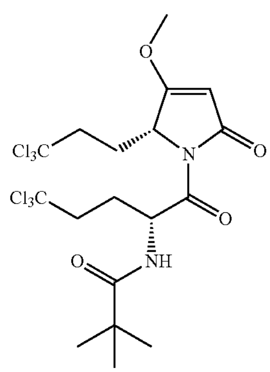 |
| 1-6 | 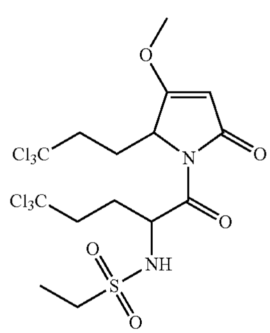 |
| 1-6a | |
| 1-6b | |
| 1-6c | |
| 1-6d | |

TABLE 1-continued

Representative Compounds

| No. | Structure |
|---|---|
| 1-7 | 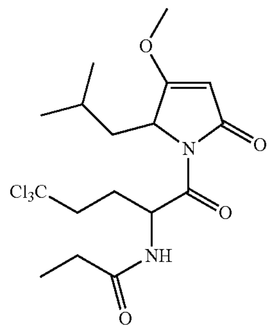 |
| 1-7a | 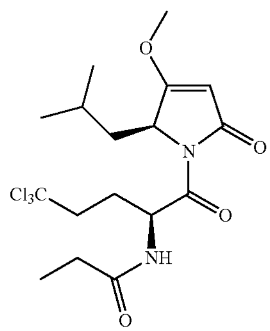 |
| 1-7b | 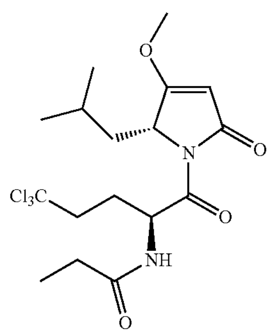 |
| 1-7c | 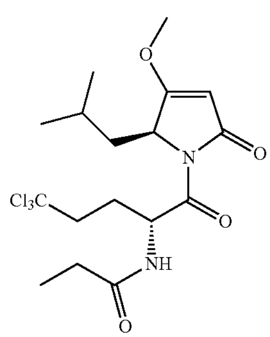 |
| 1-7d | 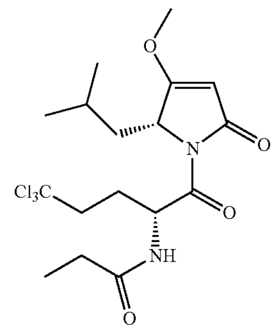 |
| 1-8 | 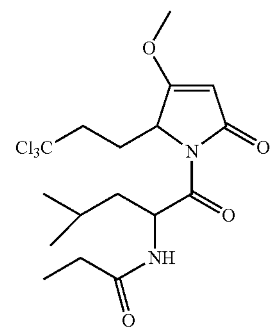 |
| 1-8a | 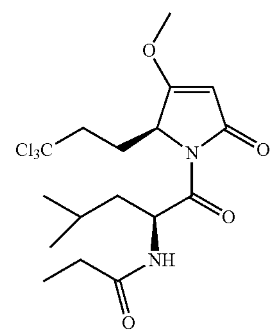 |
| 1-8b | 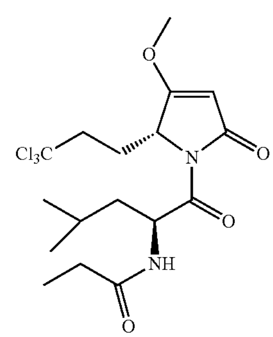 |

TABLE 1-continued
Representative Compounds
| No. | Structure |
|---|---|
| 1-8c | 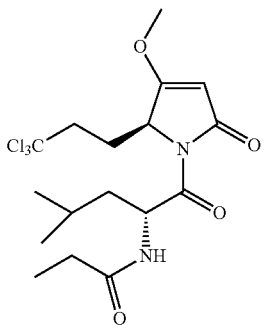 |
| 1-8d | 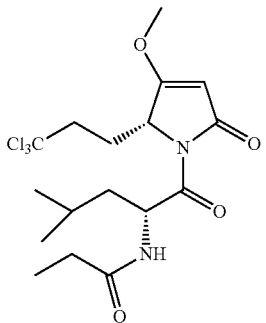 |
| 1-9 | 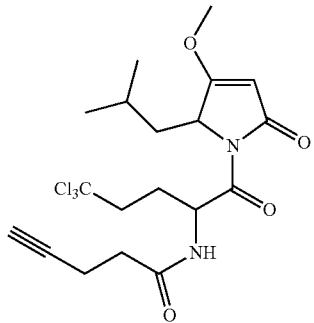 |
| 1-9a | 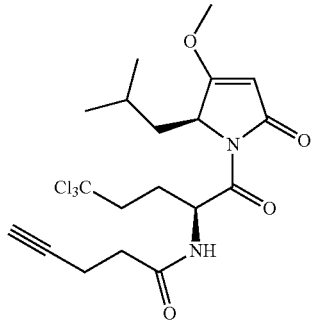 |
TABLE 1-continued
Representative Compounds
| No. | Structure |
|---|---|
| 1-9b | 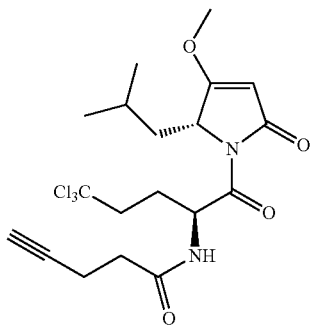 |
| 1-9c | 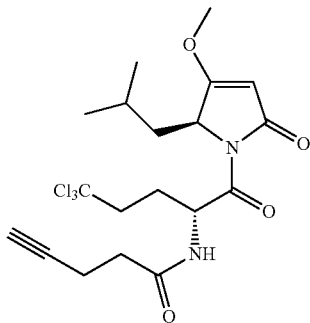 |
| 1-9d | 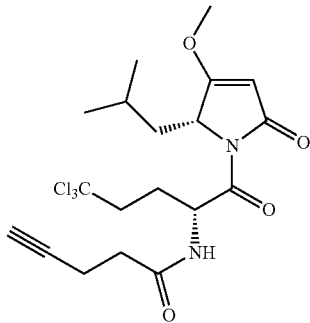 |
| 1-10 | 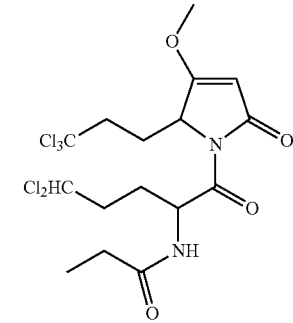 |

TABLE 1-continued
Representative Compounds
| No. | Structure |
|---|---|
| 1-10a | 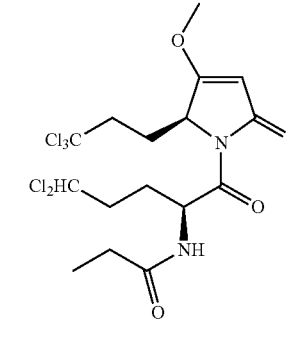 |
| 1-10b | 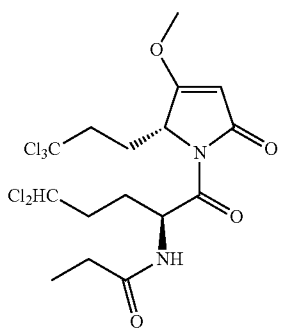 |
| 1-10c | 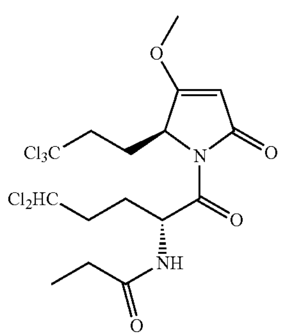 |
| 1-10d | 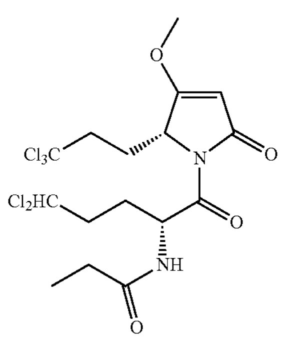 |
TABLE 1-continued
Representative Compounds
| No. | Structure |
|---|---|
| 1-11 | 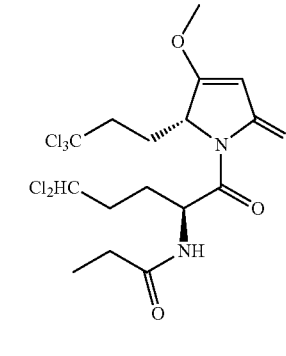 |
| 1-11a | 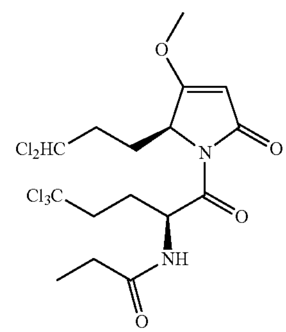 |
| 1-11b | 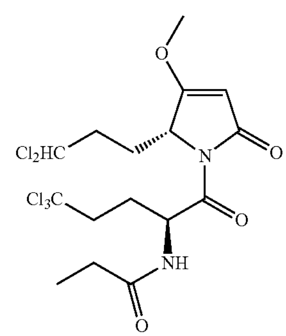 |
| 1-11c | 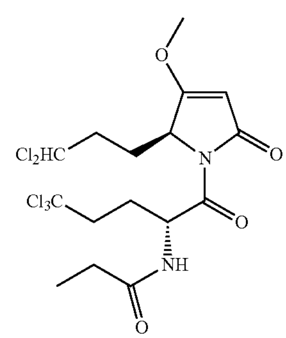 |

TABLE 1-continued

Representative Compounds

| No. | Structure |
|---|---|
| 1-11d | 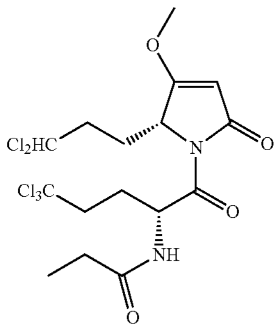 |
| 1-12 | 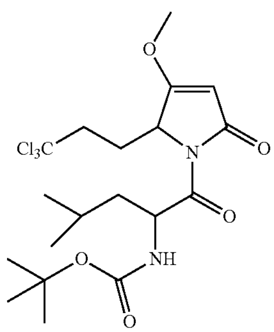 |
| 1-12a | 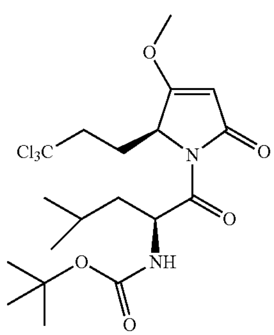 |
| 1-12b | 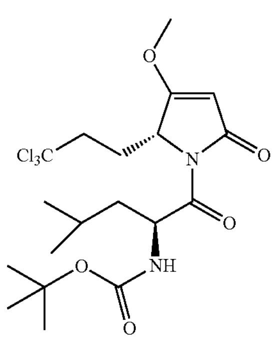 |
| 1-12c | |
| 1-12d | |
| 1-13 | |
| 1-13a | |

TABLE 1-continued

Representative Compounds

| No. | Structure |
|---|---|
| 1-13b | 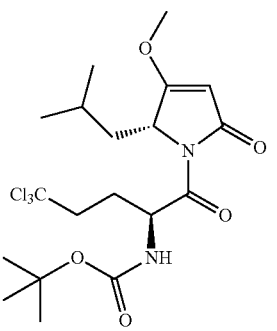 |
| 1-13c | 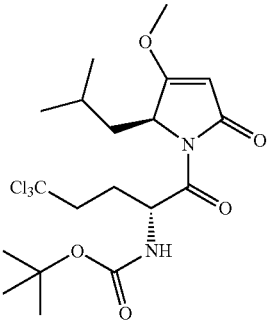 |
| 1-13d | 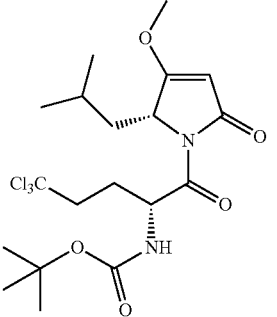 |
| N/A | N/A |

Compounds as described herein may be in the free form or in the form of a salt thereof. In some embodiments, compounds as described herein may be in the form of a pharmaceutically acceptable salt, which are known in the art (Berge et al., *J. Pharm. Sci.* 1977, 66, 1). Pharmaceutically acceptable salt as used herein includes, for example, salts that have the desired pharmacological activity of the parent compound (salts which retain the biological effectiveness and/or properties of the parent compound and which are not biologically and/or otherwise undesirable). Compounds as described herein having one or more functional groups capable of forming a salt may be, for example, formed as a pharmaceutically acceptable salt. Compounds containing one or more basic functional groups may be capable of forming a pharmaceutically acceptable salt with, for example, a pharmaceutically acceptable organic or inorganic acid. Pharmaceutically acceptable salts may be derived from, for example, and without limitation, acetic acid, adipic acid, alginic acid, aspartic acid, ascorbic acid, benzoic acid, benzenesulfonic acid, butyric acid, cinnamic acid, citric acid, camphoric acid, camphorsulfonic acid, cyclopentanepropionic acid, diethylacetic acid, digluconic acid, dodecylsulfonic acid, ethanesulfonic acid, formic acid, fumaric acid, glucoheptanoic acid, gluconic acid, glycerophosphoric acid, glycolic acid, hemisulfonic acid, heptanoic acid, hexanoic acid, hydrochloric acid, hydrobromic acid, hydriodic acid, 2-hydroxyethanesulfonic acid, isonicotinic acid, lactic acid, malic acid, maleic acid, malonic acid, mandelic acid, methanesulfonic acid, 2-napthalenesulfonic acid, naphthalenedisulphonic acid, p-toluenesulfonic acid, nicotinic acid, nitric acid, oxalic acid, pamoic acid, pectinic acid, 3-phenylpropionic acid, phosphoric acid, picric acid, pimelic acid, pivalic acid, propionic acid, pyruvic acid, salicylic acid, succinic acid, sulfuric acid, sulfamic acid, tartaric acid, thiocyanic acid or undecanoic acid. Compounds containing one or more acidic functional groups may be capable of forming pharmaceutically acceptable salts with a pharmaceutically acceptable base, for example, and without limitation, inorganic bases based on alkaline metals or alkaline earth metals or organic bases such as primary amine compounds, secondary amine compounds, tertiary amine compounds, quaternary amine compounds, substituted amines, naturally occurring substituted amines, cyclic amines or basic ion-exchange resins. Pharmaceutically acceptable salts may be derived from, for example, and without limitation, a hydroxide, carbonate, or bicarbonate of a pharmaceutically acceptable metal cation such as ammonium, sodium, potassium, lithium, calcium, magnesium, iron, zinc, copper, manganese or aluminum, ammonia, benzathine, meglumine, methylamine, dimethylamine, trimethylamine, ethylamine, diethylamine, triethylamine, isopropylamine, tripropylamine, tributylamine, ethanolamine, diethanolamine, 2-dimethylaminoethanol, 2-diethylaminoethanol, dicyclohexylamine, lysine, arginine, histidine, caffeine, hydrabamine, choline, betaine, ethylenediamine, glucosamine, glucamine, methylglucamine, theobromine, purines, piperazine, piperidine, procaine, N-ethylpiperidine, theobromine, tetramethylammonium compounds, tetraethylammonium compounds, pyridine, N,N-dimethylaniline, N-methylpiperidine, morpholine, N-methylmorpholine, N-ethylmorpholine, dicyclohexylamine, dibenzylamine, N,N-dibenzylphenethylamine, 1-ephenamine, N,N'-dibenzylethylenediamine or polyamine resins. In some embodiments, compounds as described herein may contain both acidic and basic groups and may be in the form of inner salts or zwitterions, for example, and without limitation, betaines. Salts as described herein may be prepared by conventional processes known to a person skilled in the art, for example, and without limitation, by reacting the free form with an organic acid or inorganic acid or base, or by anion exchange or cation exchange from other salts. Those skilled in the art will appreciate that preparation of salts may occur in situ during isolation and purification of the compounds or preparation of salts may occur by separately reacting an isolated and purified compound.

In some embodiments, compounds and all different forms thereof (e.g. free forms, salts, polymorphs, isomeric forms) as described herein may be in the solvent addition form, for example, solvates. Solvates contain either stoichiometric or non-stoichiometric amounts of a solvent in physical association the compound or salt thereof. The solvent may be, for example, and without limitation, a pharmaceutically acceptable solvent. For example, hydrates are formed when the solvent is water or alcoholates are formed when the solvent is an alcohol.

In some embodiments, compounds and all different forms thereof (e.g. free forms, salts, solvates, isomeric forms) as described herein may include crystalline and amorphous forms, for example, polymorphs, pseudopolymorphs, conformational polymorphs, amorphous forms, or a combination thereof. Polymorphs include different crystal packing arrangements of the same elemental composition of a compound. Polymorphs usually have different X-ray diffraction patterns, infrared spectra, melting points, density, hardness, crystal shape, optical and electrical properties, stability and/or solubility. Those skilled in the art will appreciate that various factors including recrystallization solvent, rate of crystallization and storage temperature may cause a single crystal form to dominate.

In some embodiments, compounds and all different forms thereof (e.g. free forms, salts, solvates, polymorphs) as described herein include isomers such as geometrical isomers, optical isomers based on asymmetric carbon, stereoisomers, tautomers, individual enantiomers, individual diastereomers, racemates, diastereomeric mixtures and combinations thereof, and are not limited by the description of the Structure illustrated for the sake of convenience.

The present disclosure also provides a pharmaceutical composition comprising any one or more of the compounds (e.g., compounds of structure I) disclosed herein and a pharmaceutically acceptable carrier. In some embodiments, the pharmaceutical composition may be for treating one or more of the following: prostate cancer, breast cancer, ovarian cancer, endometrial cancer, bladder cancer, pancreatic cancer, hepatocellular cancer, kidney cancer, liver cancer, salivary gland carcinoma, hair loss, acne, hirsutism, ovarian cysts, polycystic ovary disease, precocious puberty, spinal and bulbar muscular atrophy, and age-related macular degeneration.

In some embodiments, the pharmaceutical composition is formulated for topical administration.

In some embodiments, pharmaceutical compositions in accordance with this invention may comprise a compound of Structure I, or a salt of such a compound, preferably a pharmaceutically or physiologically acceptable salt and a pharmaceutically acceptable carrier. Pharmaceutical preparations will typically comprise one or more carriers, excipients or diluents acceptable for the mode of administration of the preparation, be it by injection, inhalation, topical administration, lavage, or other modes suitable for the selected treatment. Suitable carriers, excipients or diluents are those known in the art for use in such modes of administration.

Suitable pharmaceutical compositions may be formulated by means known in the art and their mode of administration and dose determined by the skilled practitioner. For parenteral administration, a compound may be dissolved in sterile water or saline or a pharmaceutically acceptable vehicle used for administration of non-water soluble compounds such as those used for vitamin K. For enteral administration, the compound may be administered in a tablet, capsule or dissolved in liquid form. The tablet or capsule may be enteric coated, or in a formulation for sustained release. Many suitable formulations are known, including, polymeric or protein microparticles encapsulating a compound to be released, ointments, pastes, gels, hydrogels, or solutions which can be used topically or locally to administer a compound. A sustained release patch or implant may be employed to provide release over a prolonged period of time. Many techniques known to one of skill in the art are described in *Remington: the Science & Practice of Pharmacy* by Alfonso Gennaro, 20th ed., Lippencott Williams & Wilkins, (2000). Formulations for parenteral administration may, for example, contain excipients, polyalkylene glycols such as polyethylene glycol, oils of vegetable origin, or hydrogenated naphthalenes. Biocompatible, biodegradable lactide polymer, lactide/glycolide copolymer, or polyoxyethylene-polyoxypropylene copolymers may be used to control the release of the compounds. Other potentially useful parenteral delivery systems for modulatory compounds include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

Compounds for use in the present invention may be obtained from medical sources or modified using known methodologies from naturally occurring compounds. In addition, methods of preparing or synthesizing compounds of the present invention will be understood by a person of skill in the art having reference to known chemical synthesis principles, for example the synthetic procedures set forth in PCT Pub. No. WO 2010/020055; which application is hereby incorporated by reference in its entirety for all purposes.

For example, certain embodiments of the compounds of the present invention may be prepared with reference to the following General Reaction Scheme I:

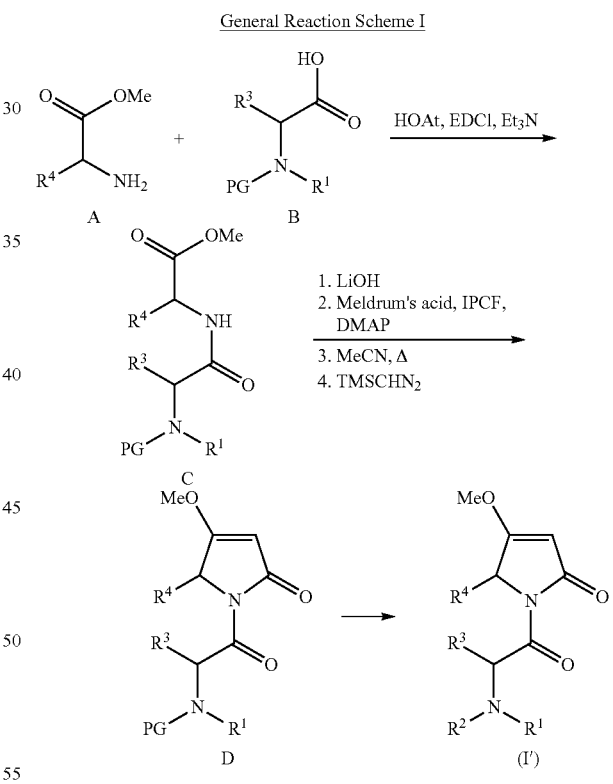

General Reaction Scheme I, wherein PG represents a protecting group and all other "R" groups are as defined herein, provides an exemplary method for preparation of compounds of structure (I) wherein $Y^1$ and $Y^2$ are O, $R^5$ is methoxy and $R^6$ is H (i.e., a compound of structure (I')). Referring to General Reaction Scheme I, appropriate amino acids or amino acid esters (B and A, respectively) can be purchased or prepared according to methods known in the art. In certain embodiments, these compounds can be prepared from an appropriate a, b-unsaturated ester as illustrated in the examples. Chiral reagents, such as Ellman's sulfonamide may be employed to impart the desired stereochemistry of the amino acid (or ester) reagents.

Amide coupling of A and B using standard reagents (e.g., HOAt and EDCI) results in dipeptide C. Dipeptide C is then cyclized by reaction with Meldrum's acid as illustrated in General Reaction Scheme I to yield compounds of structure D. PG can optionally be removed and the desired $R^2$ group installed using any number of techniques, including reaction with an appropriately substituted acyl chloride. Alternatively, PG corresponds to $R^2$ and no further manipulation is required.

It should be noted that General Reaction Scheme I illustrates an embodiment wherein $Y^1$ and $Y^2$ are O, $R^5$ is methoxy and $R^6$ is H; however, the disclosed compounds are not limited to these embodiments. Other embodiments may be prepared according to methods analogous to those described above and in the examples. For example, additional synthetic modifications may be employed to arrive at different embodiments and/or different starting materials may be employed such that the desired structure is obtained without need for further modification. Further, various of the described synthetic procedures may result in a mixture of stereoisomers (e.g., enantiomers and/or diastereomers). Such stereoisomers can be separated using known techniques and/or stereospecific or stereoselective reagents and/or methods may be employed to arrive at the desired stereoisomer.

One skilled in the art will recognize that variations to the order of the steps and reagents discussed in reference to the above synthetic schemes are possible. Furthermore, an appropriate protecting group strategy, such as those described in, *Greene's Protective Groups in Organic Synthesis*, 4$^{th}$ Ed., Peter G. M. Wuts and Theodora W. Greene, John Wiley and Sons, Inc., 2007, which is hereby incorporated by reference in its entirety, may also be employed. In addition, compounds of structure I having various substitutions (e.g., different values for $Y^1, Y^2, R^1, R^2, R^3, R^4, R^5, R^6$, etc.) and different positional isomers can be prepared by modifications to the above starting materials and/or procedures. Such modifications are well within the ability of one of ordinary skill in the art.

III. Methods

The present compounds find use in any number of methods. For example, in some embodiments the compounds are useful in methods for modulating androgen receptor (AR). Accordingly, in one embodiment, the present disclosure provides the use of a composition comprising any one of the foregoing compounds of Structure (I) for modulating androgen receptor (AR) activity. For example in some embodiments, modulating androgen receptor (AR) activity is in a mammalian cell. Modulating androgen receptor (AR) may be in a subject in need thereof (e.g., a mammalian subject) and for treatment of any of the described conditions or diseases.

In other embodiments, modulating androgen receptor (AR) activity is for treatment of at least one indication selected from the group consisting of: prostate cancer, breast cancer, ovarian cancer, endometrial cancer, bladder cancer, pancreatic cancer, hepatocellular cancer, kidney cancer, liver cancer, salivary gland carcinoma, hair loss, acne, hirsutism, ovarian cysts, polycystic ovary disease, precocious puberty, spinal and bulbar muscular atrophy, and age-related macular degeneration. For example in some embodiments, the indication is prostate cancer. In other embodiments, the prostate cancer is castration resistant prostate cancer (also referred to as hormone refractory, androgen-independent, androgen deprivation resistant, androgen ablation resistant, androgen depletion-independent, castration-recurrent, anti-androgen-recurrent). While in other embodiments, the prostate cancer is androgen-dependent prostate cancer.

In other embodiments, the present disclosure provides a method of modulating androgen receptor (AR) activity, the method comprising administering a composition comprising any one of the foregoing compounds of Structure (I), or pharmaceutically acceptable salt, stereoisomer or tautomer thereof to a subject (e.g., mammal) in need thereof.

In other further embodiments of the foregoing method, modulating androgen receptor (AR) activity is for the treatment of one or more of the following: prostate cancer, breast cancer, ovarian cancer, endometrial cancer, bladder cancer, pancreatic cancer, hepatocellular cancer, kidney cancer, liver cancer, salivary gland carcinoma, hair loss, acne, hirsutism, ovarian cysts, polycystic ovary disease, precocious puberty, spinal and bulbar muscular atrophy, and age-related macular degeneration. For example in some embodiments, the prostate cancer is castration resistant prostate cancer (also referred to as hormone refractory, androgen-independent, androgen deprivation resistant, androgen ablation resistant, androgen depletion-independent, castration-recurrent, anti-androgen-recurrent). In other embodiments, the prostate cancer is androgen-dependent prostate cancer.

In accordance with another embodiment, there is provided a use of the compounds of Structure (I) as described anywhere herein for preparation of a medicament for modulating androgen receptor (AR).

In accordance with a further embodiment, there is provided a method of screening for androgen receptor (AR) modulating compounds, wherein the compounds screened are selected from the compounds as described anywhere herein.

The modulating of the androgen receptor (AR) activity may be in a mammalian cell. The modulating of the androgen receptor (AR) activity may be in a mammal. The mammal may be a human.

Alternatively, the administering may be to a mammal. The administering may be to a mammal in need thereof and in an effective amount for the treatment of at least one indication selected from the group consisting of: prostate cancer, breast cancer, ovarian cancer, endometrial cancer, bladder cancer, pancreatic cancer, hepatocellular cancer, kidney cancer, liver cancer, salivary gland carcinoma, hair loss, acne, hirsutism, ovarian cysts, polycystic ovary disease, precocious puberty, spinal and bulbar muscular atrophy (e.g., Kennedy's disease), and age-related macular degeneration.

The mammalian cell may be a human cell. The modulating androgen receptor (AR) activity may be for inhibiting androgen receptor (AR) N-terminal domain activity. The modulating androgen receptor (AR) activity may be for inhibiting androgen receptor (AR) activity. The modulating may be in vivo. The modulating androgen receptor (AR) activity may be for treatment of at least one indication selected from the group consisting of: prostate cancer, breast cancer, ovarian cancer, endometrial cancer, bladder cancer, pancreatic cancer, hepatocellular cancer, kidney cancer, liver cancer, salivary gland carcinoma, hair loss, acne, hirsutism, ovarian cysts, polycystic ovary disease, precocious puberty, spinal and bulbar muscular atrophy (e.g., Kennedy's disease), and age-related macular degeneration. The indication may be prostate cancer. The prostate cancer may be castration-resistant prostate cancer. The prostate cancer may be androgen-dependent prostate cancer.

In some embodiments, compounds and all different forms thereof as described herein may be used, for example, and without limitation, in combination with other treatment methods for at least one indication selected from the group consisting of: prostate cancer, breast cancer, ovarian cancer, endometrial cancer, bladder cancer, pancreatic cancer, hepatocellular cancer, kidney cancer, liver cancer, salivary gland carcinoma, hair loss, acne, hirsutism, ovarian cysts, polycystic ovary disease, precocious puberty, spinal and bulbar muscular atrophy, and age-related macular degeneration. For example, compounds and all their different forms as described herein may be used as neoadjuvant (prior), adjunctive (during), and/or adjuvant (after) therapy with surgery, radiation (brachytherapy or external beam), or other therapies (e.g., HIFU), and in combination with chemotherapies, androgen ablation, antiandrogens or any other therapeutic approach.

With respect to combination therapies, one embodiment of the present disclosure provides a combination of any one or more of a compound of Structure I with one or more currently-used or experimental pharmacological therapies which are or may be utilized to treat any of the above disease states (e.g., castration resistant prostate cancer or Kennedy's disease). Methods, uses and pharmaceutical compositions comprising the above combination are also provided. The compound of structure (I) may either be administered together with the additional pharmacological therapy or the compounds may be administered separately.

In some embodiments, the present invention is directed to a method for modulating androgen receptor (AR) (e.g., for treatment of any of the above conditions) by administering to a subject in need thereof a pharmaceutical composition comprising a compound of structure I and an additional therapeutic agent. Pharmaceutical compositions (and uses thereof) comprising any one of the foregoing compounds of Formula (I), an additional therapeutic agent and a pharmaceutically acceptable carrier are also provided. For example, in some embodiments, the additional therapeutic agent is for treating prostate cancer, breast cancer, ovarian cancer, endometrial cancer, bladder cancer, pancreatic cancer, hepatocellular cancer, kidney cancer, liver cancer, salivary gland carcinoma, hair loss, acne, hirsutism, ovarian cysts, polycystic ovary disease, precocious puberty, spinal and bulbar muscular atrophy or age-related macular degeneration.

The disclosed compounds, which are thought to interfere with androgen receptor (AR) principally through binding to the N-terminus domain of the androgen receptor (AR), are expected to demonstrate beneficial synergistic therapeutic effects when used in concert with existing approved and in-development agents. That is, the biological impact of using the agents in concert with one another produces a biological and therapeutic effect which is greater than the simple additive effect of each of them separately.

Accordingly, one embodiment comprises the use of the disclosed compounds in combination therapy with one or more currently-used or experimental pharmacological therapies which are utilized for treating the above disease states irrespective of the biological mechanism of action of such pharmacological therapies, including without limitation pharmacological therapies which directly or indirectly inhibit the androgen receptor (AR), pharmacological therapies which are cyto-toxic in nature, and pharmacological therapies which interfere with the biological production or function of androgen (hereinafter, the "Other Therapeutic Agents"). By "combination therapy" is meant the administration of any one or more of a compound of Structure I with one or more of another therapeutic agent to the same patient such that their pharmacological effects are contemporaneous with one another, or if not contemporaneous, that their effects are synergistic with one another even though dosed sequentially rather than contemporaneously.

Such administration includes without limitation dosing of one or more of a compound of Structure I and one or more of the Other Therapeutic Agent(s) as separate agents without any commingling prior to dosing, as well as formulations which include one or more Other Androgen-Blocking Therapeutic Agents mixed with one or more compound of Structure I as a pre-mixed formulation. Administration of the compound(s) of Structure I in combination with Other Therapeutic Agents for treatment of the above disease states also includes dosing by any dosing method including without limitation, topical delivery, intravenous delivery, oral delivery, intra-peritoneal delivery, intra-muscular delivery, or intra-tumoral delivery.

In another aspect of the present disclosure, the one or more of the Other Therapeutic Agent may be administered to the patient before administration of the compound(s) of Structure I. In another embodiment, the compound(s) of Structure I may be co-administered with one or more of the Other Therapeutic Agents. In yet another aspect, the one or more Other Therapeutic Agent may be administered to the patient after administration of the compound(s) of Structure I.

It is fully within the scope of the disclosure that the ratio of the doses of compound(s) of Structure I to that of the one or more Other Therapeutic Agents may or may not equal to one and may be varied accordingly to achieve the optimal therapeutic benefit.

For greater clarity the compound(s) of Structure I that are combined with the one or more Other Therapeutic Agents for improved treatment of the above disease states may comprise, but are not limited to any compound having a structure of Structure I, including those compounds shown in Table 1.

The Other Therapeutic Agents include without limitation any pharmacological agent which is currently approved by the FDA in the U.S. (or elsewhere by any other regulatory body) for use as pharmacological treatment of any of the above disease states, or which is currently being used experimentally as part of a clinical trial program that relates to the above disease states. Non-limiting examples of the Other Pharmacological Agents comprise, without limitation: the chemical entity known as enzalutamide (4-(3-(4-cyano-3-(trifluoromethyl)phenyl)-5,5-dimethyl-4-oxo-2-thioxoimidazolidin-1-yl)-2-fluoro-N-methylbenzamide) and related compounds, which appears to be a blocker of the androgen receptor (AR) LBD and is an FDA-approved treatment for prostate cancer; the chemical entity known as Galeterone and related compounds which appears to be a blocker of the androgen receptor (AR) LBD, and a CYP17 lyase inhibitor, and also appears to decrease overall androgen receptor (AR) levels in prostate cancer cells. Galeterone is currently in development as a treatment for prostate cancer; the chemical entity known as ARN-509 and related compounds which appears to be a blocker of the androgen receptor (AR) LBD and is currently in development as a treatment for prostate cancer; the chemical entity known as ODM-201 and related compounds, the chemical entity known as abiraterone (or CB-76 30; (3S,8R,9S,10R,13S,14S)-10,13-dimethyl-17-(pyridin-3-yl) 2,3,4,7,8,9,10,11,12,13,14,15-dodecahydro-1H-cyclopenta[a]phenanthren-3-ol), and related molecules, which appears to block the production of androgen and is an FDA-approved treatment for prostate cancer; the chemical entity known as bicalutamide (N-[4-cyano-3-(trifluoromethyl)phenyl]-3-[(4-fluorophenyl)sulfonyl]-2-hydroxy-2-methylpropanamide) and related compounds, which appears to be a blocker of the AR LBD and which is currently used to treat prostate cancer, the chemical entity known as nilutamide (5,5-dimethyl-3-[4-nitro-3-(trifluoromethyl)phenyl]imidazolidine-2,4-dione) and related compounds, which appears to be a blocker of the androgen receptor (AR) LBD and which is currently used to treat prostate cancer, the chemical entity known as flutamide (2-methyl-N-[4-nitro-3-(trifluoromethyl)phenyl]-propanamide) and related compounds, which appears to be a blocker of the androgen receptor (AR) LBD and which is currently used to treat prostate cancer, the chemical entities known as cyproterone acetate (6-chloro-1β,2β-dihydro-17-hydroxy-3'H-cyclopropa[1,2]pregna-4,6-diene-3,20-dione) and related compounds, which appears to be a blocker of the androgen receptor (AR) LBD and which is currently used to treat prostate cancer, the chemical entity known as docetaxel (Taxotere; 1,7β,10β-trihydroxy-9-oxo-5β,20-epoxytax-11-ene-2α,4,13α-triyl 4-acetate 2-benzoate 13-{(2R,3S)-3-[(tert-butoxycarbonyl)amino]-2-hydroxy-3-phenylpropanoate}) and related compounds, which appears to be a cytotoxic antimicrotubule agent and is currently used in combination with prednisone to treat prostate cancer, the chemical entity known as Bevacizumab (Avastin), a monoclonal antibody that recognizes and blocks vascular endothelial growth factor A (VEGF-A) and may be used to treat prostate cancer, the chemical entity known as OSU-HDAC42 ((S)-(+)-N-hydroxy-4-(3-methyl-2-phenylbutyrylamino)-benzamide), and related compounds, which appears to act as a histone deacetylase inhibitor, and is currently being developed as a treatment for prostate cancer, the chemical entity known as VITAXIN which appears to be a monoclonal antibody against the vascular integrin αvβ3 to prevent angiogenesis, and which may be used to treat prostate cancer, the chemical entity known as sunitumib (N-(2-diethylaminoethyl)-5-[(Z)-(5-fluoro-2-oxo-1H-indol-3-ylidene)methyl]-2,4-dimethyl-1H-pyrrole-3-carboxamide) and related compounds, which appears to inhibit multiple receptor tyrosine kinases (RTKs) and may be used for treatment of prostate cancer, the chemical entity known as ZD-4054 (N-(3-Methoxy-5-methylpyrazin-2-yl)-2-[4-(1,3,4-oxadiazol-2-yl)phenyl]pyridin-3-sulfonamid) and related compounds, which appears to block the edta receptor and which may be used for treatment of prostate cancer, 6 the chemical entity known as Cabazitaxel (XRP-6258), and related compounds, which appears to be a cytotoxic microtubule inhibitor, and which is currently used to treat prostate cancer; the chemical entity known as MDX-010 (Ipilimumab), a fully human monoclonal antibody that binds to and blocks the activity of CTLA-4 which is currently in development as an immunotherapeutic agent for treatment of prostate cancer; the chemical entity known as OGX 427 which appears to target HSP27 as an antisense agent, and which is currently in development for treatment of prostate cancer; the chemical entity known as OGX 011 which appears to target clusterin as an antisense agent, and which is currently in development as a treatment for prostate cancer; the chemical entity known as finasteride (Proscar, Propecia; N-(1,1-dimethylethyl)-3-oxo-(5α, 17β)-4-azaandrost-1-ene-17-carboxamide), and related compounds, which appears to be a 5-alpha reductase inhibitor that reduces levels of dihydrotestosterone, and may be used to treat prostate cancer; the chemical entity known as dutasteride (Avodart; 5α, 17β)-N-{2,5 bis(trifluoromethyl)phenyl}-3-oxo-4-azaandrost-1-ene-17-carboxamide) and related molecules, which appears to be a 5-alpha reductase inhibitor that reduces levels of dihydrotestosterone, and may be used in the treatment of prostate cancer; the chemical entity known as turosteride ((4aR,4bS,6aS,7S,9aS,9bS,11aR)-1,4a,6a-trimethyl-2-oxo-N-(propan-2-yl)-N-(propan-2 ylcarbamoyl)hexadecahydro-1H-indeno[5,4-f]quinoline-7-carboxamide), and related molecules, which appears to be a 5-alpha reductase inhibitor that reduces levels of dihydrotestosterone and may be used in the treatment of prostate cancer; the chemical entity known as bexlosteride (LY-191,704; (4aS,10bR)-8-chloro-4-methyl-1,2,4a,5,6,10b-hexahydrobenzo[f]quinolin-3-one), and related compounds, which appears to be a 5-alpha reductase inhibitor that reduces levels of dihydrotestosterone and may be used in the treatment of prostate cancer; the chemical entity known as izonsteride (LY-320,236; (4aR,10bR)-8-[(4-ethyl-1,3-benzothiazol-2-yl)sulfanyl]-4,10b-dimethyl-1,4,4a,5,6,10b-hexahydrobenzo[f]quinolin-3(2H)-one) and related compounds, which appears to be a 5-alpha reductase inhibitor that reduces levels of dihydrotestosterone and may be used for the treatment of prostate cancer; the chemical entity known as FCE 28260 and related compounds, which appears to be a 5-alpha reductase inhibitor that reduces levels of dihydrotestosterone and may be used for the treatment of prostate cancer; the chemical entity known as SKF105,111, and related compounds, which appears to be a 5-alpha reductase inhibitor that reduces levels of dihydrotestosterone and may be used for treatment of prostate cancer. By "related compounds" it is understood that other compounds having a similar mode of action and/or activity are also included within the scope of various embodiments. For example, related compounds include other therapeutic agents that have been used for treatment of prostate cancer, either as a monotherapy or as part of a combination therapy.

Also contemplated in certain embodiments is use of any of the compounds of structure (I) in combination with inhibitors of: PI3K, BET bromodomains and/or PARP for treatment of the above noted conditions (e.g., prostate cancer). Combinations of the compounds disclosed herein in combination with Radium 233, which is an FDA approved therapeutic, is also contemplated for the same purpose.

Accordingly, in certain embodiments the additional therapeutic agent is enzalutamide, Galeterone; ARN-509; ODM-201, abiraterone, bicalutamide, nilutamide, flutamide, cyproterone acetate, docetaxel, Bevacizumab (Avastin), OSU-HDAC42, VITAXIN, sunitumib, ZD-4054, Cabazitaxel (XRP-6258), MDX-010 (Ipilimumab), OGX 427, OGX 011, finasteride, dutasteride, turosteride, bexlosteride, izonsteride, FCE 28260, SKF105,111 Radium 233, prednisone or a related compound of any of the foregoing.

In another embodiment, the present disclosure provides the use of any one of the foregoing pharmaceutical compositions (including compositions comprising a compound of Structure I and an additional therapeutic agent) for modulating androgen receptor (AR) activity. For example in some embodiments, modulating androgen receptor (AR) activity is in a mammalian cell.

In other embodiments, modulating androgen receptor (AR) activity is for treatment of at least one indication selected from the group consisting of: prostate cancer, breast cancer, ovarian cancer, endometrial cancer, bladder cancer, pancreatic cancer, hepatocellular cancer, kidney cancer, liver cancer, salivary gland carcinoma, hair loss, acne, hirsutism, ovarian cysts, polycystic ovary disease, precocious puberty, spinal and bulbar muscular atrophy, and age-related macular degeneration. For example in some embodiments, the indication is prostate cancer. For example, in some embodiments, the prostate cancer is castration resistant prostate cancer, and in other embodiments the prostate cancer is androgen-dependent prostate cancer.

In yet another embodiment, the present disclosure provides a method of modulating androgen receptor (AR) activity, the method comprising administering any one of the foregoing pharmaceutical compositions (including compositions comprising a compound of Structure I and an additional therapeutic agent) to a subject in need thereof. For example in some embodiments, modulating androgen receptor (AR) activity is for the treatment of one or more of the following: prostate cancer, breast cancer, ovarian cancer, endometrial cancer, bladder cancer, pancreatic cancer, hepatocellular cancer, kidney cancer, liver cancer, salivary gland carcinoma, hair loss, acne, hirsutism, ovarian cysts, polycystic ovary disease, precocious puberty, spinal and bulbar muscular atrophy, and age-related macular degeneration. In still other embodiments, the indication is prostate cancer. For example, in some embodiments, the prostate cancer is castration resistant prostate cancer, while in other embodiments, the prostate cancer is androgen-dependent prostate cancer.

Compounds as described herein may be administered to a subject. As used herein, a "subject" may be a human, non-human primate, mammal, rat, mouse, cow, horse, pig, sheep, goat, dog, cat and the like. The subject may be suspected of having or at risk for having a cancer, such as prostate cancer, breast cancer, ovarian cancer, salivary gland carcinoma, bladder cancer, pancreatic cancer, hepatocellular cancer, kidney cancer, liver cancer, or endometrial cancer, or suspected of having or at risk for having acne, hirsutism, alopecia, benign prostatic hyperplasia, ovarian cysts, polycystic ovary disease, precocious puberty, spinal and bulbar muscular atrophy, or age-related macular degeneration. Diagnostic methods for various cancers, such as prostate cancer, breast cancer, ovarian cancer, salivary gland carcinoma, bladder cancer, pancreatic cancer, hepatocellular cancer, kidney cancer, liver cancer, or endometrial cancer, and diagnostic methods for acne, hirsutism, alopecia, benign prostatic hyperplasia, ovarian cysts, polycystic ovary disease, precocious puberty, spinal and bulbar muscular atrophy, or age-related macular degeneration and the clinical delineation of cancer, such as prostate cancer, breast cancer, ovarian cancer, salivary gland carcinoma, bladder cancer, pancreatic cancer, hepatocellular cancer, kidney cancer, liver cancer, or endometrial cancer, diagnoses and the clinical delineation of acne, hirsutism, alopecia, benign prostatic hyperplasia, ovarian cysts, polycystic ovary disease, precocious puberty, spinal and bulbar muscular atrophy, or age-related macular degeneration are known to those of ordinary skill in the art.

Compounds described herein may also be used in assays and for research purposes. Definitions used include ligand-dependent activation of the androgen receptor (AR) by androgens such as dihydrotestosterone (DHT) or the synthetic androgen (R1881) used for research purposes. Ligand-independent activation of androgen receptor (AR) refers to transactivation of full-length androgen receptor (AR) in the absence of androgen (ligand) by, for example, stimulation of the cAMP-dependent protein kinase (PKA) pathway with forskolin (FSK). Some compounds and compositions of this invention may inhibit both FSK and androgen (e.g. R1881, a synthetic androgen) induction of ARE-luciferase (ARE-luc). Constitutive activity of androgen receptor (AR) refers to splice variants lacking androgen receptor (AR) ligand-binding domain. Such compounds may block a mechanism that is common to both ligand-dependent and ligand-independent activation of androgen receptor (AR), as well as constitutively active splice variants of androgen receptor (AR) that lack ligand-binding domain. This could involve any step in activation of androgen receptor (AR) including dissociation of heatshock proteins, essential posttranslational modifications (e.g., acetylation, phosphorylation), nuclear translocation, protein-protein interactions, formation of the transcriptional complex, release of co-repressors, and/or increased degradation. Some compounds and compositions of this invention may inhibit ligand-only activity and may interfere with a mechanism specific to ligand-dependent activation (e.g., accessibility of the ligand binding domain (LBD) to androgen). Numerous disorders in addition to prostate cancer involve the androgen axis (e.g., acne, hirsutism, alopecia, benign prostatic hyperplasia) and compounds interfering with this mechanism may be used to treat such conditions.

Compounds or pharmaceutical compositions in accordance with this invention or for use in this invention may be administered by means of a medical device or appliance such as an implant, graft, prosthesis, stent, etc. Also, implants may be devised which are intended to contain and release such compounds or compositions. An example would be an implant made of a polymeric material adapted to release the compound over a period of time.

It is to be noted that dosage values may vary with the severity of the condition to be alleviated. For any particular subject, specific dosage regimens may be adjusted over time according to the individual need and the professional judgment of the person administering or supervising the administration of the compositions. Dosage ranges set forth herein are exemplary only and do not limit the dosage ranges that may be selected by medical practitioners. The amount of active compound(s) in the composition may vary according to factors such as the disease state, age, sex, and weight of the subject. Dosage regimens may be adjusted to provide the optimum therapeutic response. For example, a single bolus may be administered, several divided doses may be administered over time or the dose may be proportionally reduced or increased as indicated by the exigencies of the therapeutic situation. It may be advantageous to formulate parenteral compositions in dosage unit form for ease of administration and uniformity of dosage.

The compounds described herein may be used for in vivo or in vitro research uses (i.e. non-clinical) to investigate the mechanisms of orphan and nuclear receptors (including steroid receptors such as AR). Furthermore, these compounds may be used individually or as part of a kit for in vivo or in vitro research to investigate signal transduction pathways and/or the activation of orphan and nuclear receptors using recombinant proteins, cells maintained in culture, and/or animal models.

Various alternative embodiments and examples of the invention are described herein. These embodiments and examples are illustrative and should not be construed as limiting the scope of the invention. The following examples are provided for purposes of illustration, not limitation.

EXAMPLES

All non-aqueous reactions were performed in flame-dried round bottomed flasks. The flasks were fitted with rubber septa and reactions were conducted under a positive pressure of argon unless otherwise specified. Stainless steel syringes were used to transfer air- and moisture-sensitive liquids. Flash column chromatography was performed as described by Still et al. (Still, W. C.; Kahn, M.; Mitra, A. *J. Org. Chem.* 1978, 43, 2923) using 230-400 mesh silica gel. Thin-layer chromatography was performed using aluminium plates pre-coated with 0.25 mm 230-400 mesh silica gel impregnated with a fluorescent indicator (254 nm). Thin-layer chromatography plates were visualized by exposure to ultraviolet light and a "Seebach" staining solution (700 mL water, 10.5 g Cerium (IV) sulphate tetrahydrate, 15.0 g molybdato phosphoric acid, 17.5 g sulphuric acid) followed by heating (~1 min) with a heating gun (~250° C.). Organic solutions were concentrated on Büchi R-114 rotatory evaporators at reduced pressure (15-30 torr, house vacuum) at 25-40° C.

Commercial regents and solvents were used as received. All solvents used for extraction and chromatography were HPLC grade. Normal-phase Si gel Sep Paks™ were purchased from waters, Inc. Thin-layer chromatography plates were Kieselgel 60F$_{254}$. All synthetic reagents were purchased from Sigma Aldrich and Fisher Scientific Canada.

Proton nuclear magnetic resonance ($^1$H NMR) spectra were recorded at 25° C. using a Bruker 400 with inverse probe and Bruker 400 spectrometers, are reported in parts per million on the δ scale, and are referenced from the residual protium in the NMR solvent (CDCl$_3$: δ 7.27 (CHCl$_3$)). Carbon-13 nuclear magnetic resonance ($^{13}$C NMR) spectra were recorded with a Bruker 400 spectrometer, are reported in parts per million on the δ scale, and are referenced from the carbon resonances of the solvent (CDCl$_3$: δ 77.23). Spectral features are tabulated in the following order: chemical shift (δ, ppm); multiplicity (s=singlet, d=doublet, t=triplet, m=multiplet, br=broad); coupling constant (J, Hz, number of protons).

LNCaP cells were employed for these experiments because they express endogenous androgen receptor (AR) and secrete prostate-specific antigen (PSA) (Horoszewicz et al 1983 Cancer Res. 43, 1809-1818). LNCaP cells can be grown either as monolayers in cell culture or as tumors in the well-characterized xenograft model that progresses to CRPC in castrated hosts (Sato et al 1996 J. Steroid Biochem. Mol. Biol. 58, 139-146; Gleave et al 1991 Cancer Res. 51, 3753-3761; Sato et al 1997 Cancer Res. 57, 1584-1589; and Sadar et al 2002 Mol. Cancer Ther. 1(8), 629-637). R1881 (a synthetic androgen) is employed since it is stable and avoids problems associated with the labile physiological ligand dihydrotestosterone (DHT). A well characterized AR-driven reporter gene constructs that have been used extensively is the PSA (6.1 kb) enhance/promoter which contains several AREs and is highly inducible by androgens as well as by FSK and IL 6 (Ueda et al 2002 A J. Biol. Chem. 277, 7076-7085).

Example 1

Synthesis of 5,5,5-trichloro-1-norvaline methyl ester (6)

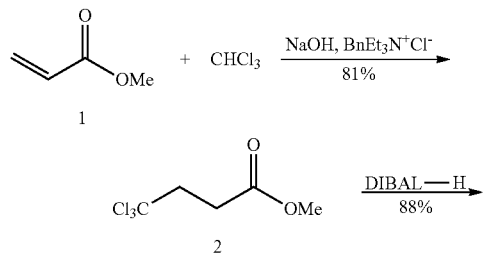

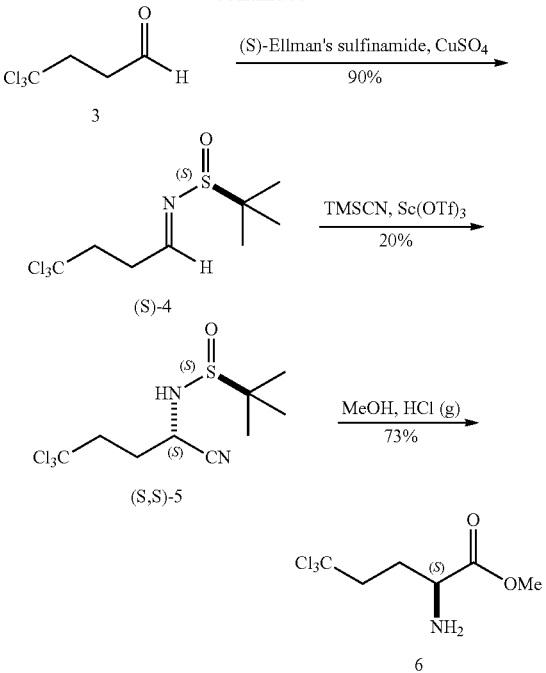

To a vigorously stirred solution of NaOH (10 g, 0.25 mol) in water (10 mL) were successively added BnEt$_3$N$^+$Cl$^-$ (0.20 g, 0.878 mmol), methyl acrylate (1) (4.0 mL, 44.4 mmol), and chloroform (40 g, 500 mmol) at 0° C. The reaction mixture was stirred at room temperature for 2 h. After addition of DCM (50 mL) and water (50 mL), the separated organic layer was washed with brine, dried over anhydrous MgSO$_4$, filtered, and concentrated in vacuo. Vacuum distillation of the crude residue gave methyl 4,4,4-trichlorobutanoate 2 (7.39 g, 36.0 mmol) as a colourless liquid in a yield of 81%. The crude residue could also be purified by silica gel flash chromatography eluting with hexanes/acetone (19:1) to afford 2. bp 78° C.-80° C./1 Torr (lit. bp 80° C./0.3 Torr); $^1$H NMR (300 MHz, CDCl$_3$) δ3.72 (s, 3H), 2.95-3.13 (m, 2H), 2.68-2.86 (m, 2H); $^{13}$C NMR (75 MHz, CDCl$_3$) δ171.6, 98.7, 52.3, 50.0, 31.4; No EI- or ESI-MS were detected.

To a stirred solution of methyl 4,4,4-trichlorobutanoate 2 (1.35 g, 6.57 mmol) in DCM (30 mL) at −78° C. was added DIBAL-H (6.57 mL, 6.57 mmol, 1.0 M in hexanes) at a rate of 1.0 mL/min. The reaction mixture was stirred at −78° C. for 1 h. After successive addition of MeOH (7 mL), HCl (25 mL, 1 M) and Rochelle salt solution (25 mL, 1 M), the reaction mixture was stirred at room temperature for another 1 h. The separated organic layer was washed with brine, dried over anhydrous MgSO$_4$, filtered, and concentrated in vacuo. The crude residue was purified by silica gel flash chromatography eluting with hexanes/EtOAc (20:1) to afford 4,4,4-trichlorobutanal 3 (1.15 g, 5.78 mmol) as a colourless oil in a yield of 88%. $^1$H NMR (400 MHz, CDCl$_3$) δ9.85 (br. s., 1H), 3.03-3.11 (m, 2H), 2.96-3.02 (m, 2H); $^{13}$C NMR (100 MHz, CDCl$_3$) δ198.5, 98.9, 47.5, 41.2.

To a stirred solution of aldehyde 3 (1.42 g, 8.09 mmol) in DCM (10 mL) were added (S)-(−)-tert-butanesulfinamide (0.98 g, 6.33 mmol) CuSO$_4$ (3.88 g, 24.2 mmol) at room temperature. The reaction mixture was stirred at room temperature for 4 days. The catalyst was removed through a pad of Celite® with DCM (200 mL) and the filtrate was concentrated in vacuo. The crude residue was purified by silica gel flash chromatography eluting with hexanes/EtOAc (100:3) to afford (S)-4 (2.0 g, 7.18 mmol) as a colourless oil in a yield of 90%. [α]$^{20}_D$+171.9° (c 0.68, CHCl$_3$); $^1$H NMR (400 MHz, CDCl$_3$) δ8.14 (br. s., 1H), 3.03-3.15 (m, 2H), 2.93-3.03 (m, 2H), 1.18 (s, 9H); $^{13}$C NMR (100 MHz, CDCl$_3$) δ 166.0, 98.9, 57.0, 50.2, 33.3, 22.5; ESI-MS m/z: 280.2 [M+H]$^+$; ESI-HRMS: m/z calcd for C$_8$H$_{15}$NO$^{32}$S$^{35}$Cl$_3$ [M+H]$^+$, 277.9940. found, 277.9942.

To a stirred solution of the sulfinimine (S)-4 (1.20 g, 4.31 mmol) in DCM (30 mL) 0° C. were added trimethylsilyl cyanide (1.17 mL, 8.61 mmol) and Sc(OTf)$_3$ (0.32 g, 0.64 mmol). The reaction mixture was stirred at 0° C. for 2 days and at room temperature for another 2 days. The reaction solution was ready to recrystallize to furnish pure diastereomeric cyanide intermediate (S,S)-5 (1.13 g, 3.69 mmol) in a yield of 20% (86% for both diastereomers). [α]$^{20}_D$+ 22.7° (c 0.39, CHCl$_3$); $^1$H NMR (600 MHz, CDCl$_3$) δ4.36 (d, J=6.7 Hz, 1H), 4.15 (br. s., 1H), 2.92 (t, J=7.7 Hz, 2H), 2.34-2.47 (m, 2H), 1.28 (s, 9H); $^{13}$C NMR (150 MHz, CDCl$_3$) δ118.5, 98.2, 57.6, 50.6, 45.0, 31.7, 22.7; ESI-MS m/z: 329.3 [M+Na]$^+$; ESI-HRMS: m/z calcd for C$_9$H$_{16}$N$_2$O$^{32}$S$^{35}$Cl$_3$ [M+H]$^+$, 305.0049. found, 305.0051.

HCl gas was generated by dripping HCl (100 mL, conc.) onto anhydrous CaCl$_2$ granule (100 g). To a stirred solution of (S,S)-5 (579 mg, 1.77 mmol) in 10 mL MeOH (10 mL) was bubbled HCl gas for 1 h. The solution was stirred at room temperature overnight. Placed in an ice/water bath, the reaction mixture was added saturated NaHCO$_3$ solution dropwise until its pH value was adjusted to pH=10. The aqueous layer was extracted with EtOAc (3×30 mL). The combined organic extract was dried over anhydrous MgSO$_4$, filtered, and evaporated in vacuo. The crude residue was purified by silica gel flash chromatography eluting with hexanes/EtOAc (5:1) to afford 6 (300 mg, 1.28 mmol) as a colourless oil in a yield of 73%. [α]$^{20}_D$+7.0° (c 1.0, CHCl$_3$); $^1$H NMR (400 MHz, CDCl$_3$) δ 3.74 (s, 3H), 3.50 (dd, J=4.9, 8.2 Hz, 1H), 2.84-2.97 (m, 1H), 2.65-2.84 (m, 1H), 2.10-2.30 (m, 1H), 1.87-2.10 (m, 1H), 1.58 (br. s., 2H); $^{13}$C NMR (100 MHz, CDCl$_3$) δ175.7, 99.7, 53.4, 52.4, 51.7, 31.6; ESI-MS m/z: 234.3 [M+H]$^+$; ESI-HRMS: m/z calcd for C$_6$H$_{11}$NO$_2$$^{35}$Cl$_3$ [M+H]$^+$, 233.9855. found, 233.9851.

Example 2

Synthesis of N-Boc-5,5,5-trichloro-d-norvaline (8)

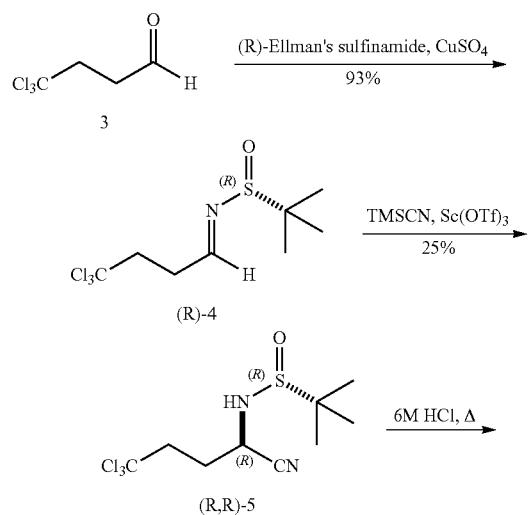

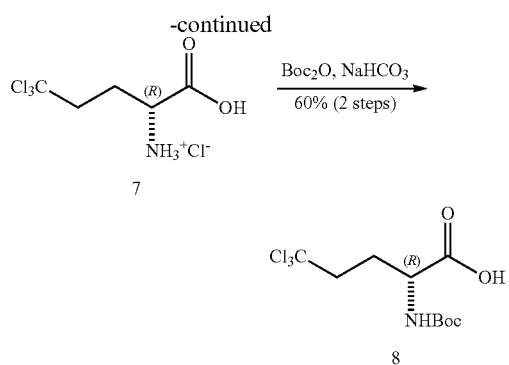

Treatment of 3 with (R)-Ellman's sulfinamide and anhydrous CuSO$_4$ yielded (R)-sulfinimine (R)-4 in 93%. An enantioselective Strecker reaction of (R)-4 with TMSCN in the presence of a catalytic amount of Sc(OTf)$_3$ furnished a pair of diastereomers. Diastereomerically pure (R,R)-cyanide (R,R)-5 was obtained from recrystallization in a yield of 25%.

Compound (R,R)-5 (449 mg, 1.46 mmol) was refluxed in HCl (10 mL, 6 M) for 0.5 h. The reaction mixture was cooled to room temperature and washed with diethyl ether (2×10 mL). The aqueous layer was evaporated at 50° C. in vacuo and freeze dried overnight. The yellowish solid 7 was directly used without purification.

To a stirred solution of the crude residue 7 (360 mg, 1.17 mmol) in saturated NaHCO$_3$ solution (20 mL) was added Boc$_2$O (254 mg, 1.17 mmol) in THF (20 mL) at room temperature. The reaction mixture was stirred at room temperature overnight. Placed in an ice/water bath, the reaction mixture was added 1M HCl dropwise until its pH value was adjusted to pH=3. The aqueous suspension was extracted with EtOAc (3×15 mL). The combined organic extract was dried over anhydrous MgSO$_4$, filtered, and concentrated in vacuo. The crude residue was purified by silica gel flash chromatography eluting with hexanes/EtOAc (2:1→1:1) to afford 8 (300 mg, 0.935 mmol) as a colourless oil in a yield of 80%. [α]$^{20}_D$−24.7° (c 4.7, CHCl$_3$); $^1$H NMR (400 MHz, MeOH-d$_4$) δ5.09 (br. s., 2H), 4.19 (dd, J=4.7, 7.8 Hz, 1H), 2.66-2.91 (m, 2H), 2.21-2.37 (m, 1H), 2.01-2.18 (m, 1H), 1.38 (s, 9H); $^{13}$C NMR (100 MHz, MeOH-d$_4$) δ174.9, 158.0, 100.6, 80.8, 53.6, 52.6, 50.0, 30.1, 28.8; ESI-MS m/z: 320.3 [M+H]$^+$; ESI-HRMS: m/z calcd for C$_{10}$H$_{16}$NO$_4$NaCl$_3$ [M+Na]$^+$, 342.0043. found, 342.0044.

Example 3

Synthesis of 1-1d and 1-1c

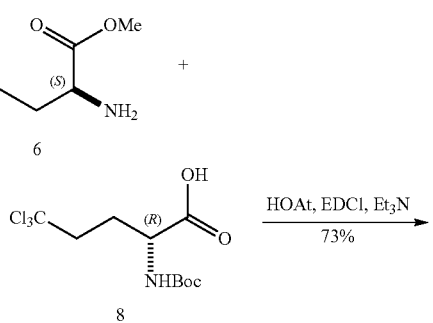

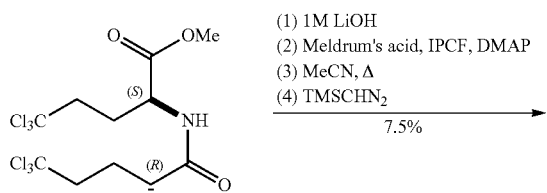
(1) 1M LiOH
(2) Meldrum's acid, IPCF, DMAP
(3) MeCN, Δ
(4) TMSCHN₂
7.5%

9

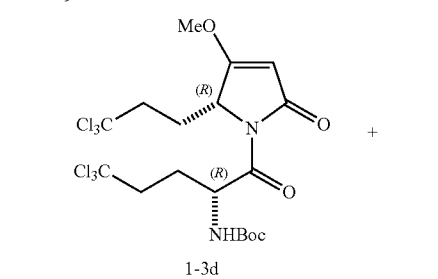

1-3d

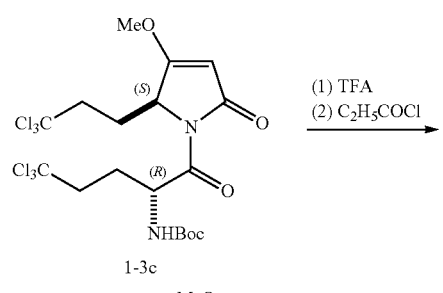

(1) TFA
(2) C₂H₅COCl 1-3c

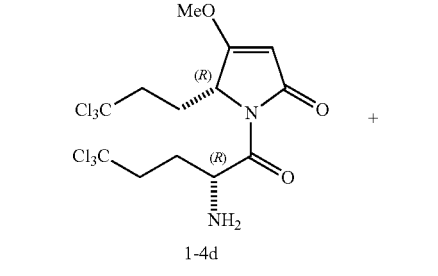

1-4d

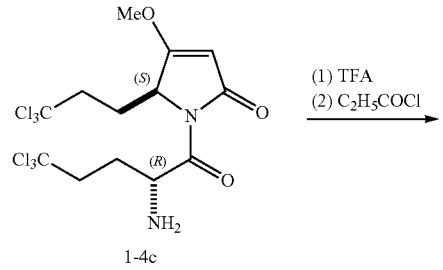

(1) TFA
(2) C₂H₅COCl 1-4c

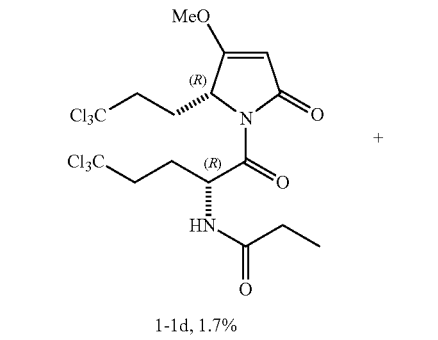

1-1d, 1.7%

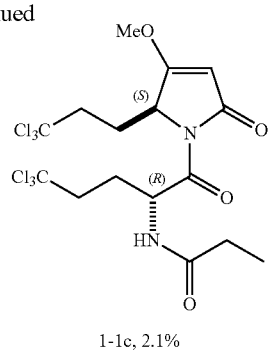

1-1c, 2.1%

To a stirred solution of 6 (89 mg, 0.380 mmol), 8 (122 mg, 0.380 mmol) and HOAt (155 mg, 1.14 mmol) in THF (10 mL) at room temperature was added EDCI (218 mg, 1.14 mmol). The reaction mixture was stirred at room temperature overnight. After addition of HCl (20 mL, 1 M), the aqueous layer was extracted with EtOAc (3×20 mL). The combined organic extract was dried over anhydrous MgSO₄, filtered, and concentrated in vacuo. The crude residue was purified by silica gel flash chromatography eluting with hexanes/EtOAc (6:1→3:1) to afford dipeptide 9 (150 mg, 0.279 mmol) as a light yellow oil in a yield of 73%. $[\alpha]^{20}_D$+21.9° (c 0.50, CHCl₃); ¹H NMR (600 MHz, CDCl₃) δ6.97 (br. s., 1H), 5.14 (d, J=6.7 Hz, 1H), 4.66-4.78 (m, 1H), 4.30 (d, J=2.0 Hz, 1H), 3.81 (s, 3H), 2.72-2.89 (m, 3H), 2.63-2.71 (m, 1H), 2.35-2.47 (m, 2H), 2.14-2.21 (m, 1H), 2.07-2.13 (m, 1H), 1.48 (s, 9H); ¹³C NMR (150 MHz, CDCl₃) δ171.8, 171.3, 155.9, 99.2, 98.9, 81.2, 53.3, 53.2, 51.3, 51.1, 51.1, 29.6, 29.3, 28.5; ESI-MS m/z: 559.2 [M+Na]⁺; ESI-HRMS: m/z calcd for $C_{16}H_{24}N_2O_5NaCl_6$ [M+Na]⁺, 556.9714. found, 556.9713.

To a stirred solution of dipeptide 9 (150 mg, 0.279 mmol) in H₂O/THF (8 mL, 1:1) at 0° C. was added LiOH (0.6 mL, 0.3 mmol, 0.5 M in H₂O). The reaction mixture was stirred at 0° C. for 1 h then THF was removed in vacuo. Placed in an ice/water bath, the reaction mixture was added 1 M HCl dropwise until its pH value was adjusted to pH=3. The aqueous layer was extracted with EtOAc (3×20 mL). The combined organic extract was dried over anhydrous MgSO₄, filtered, and concentrated in vacuo. The crude residue was used directly for the next step without further purification.

To a stirred solution of the crude carboxylic acid, Meldrum's acid (48.2 mg, 0.334 mmol), and DMAP (170.4 mg, 1.39 mmol) in DCM (10 mL) at −10° C. was added IPCC (63 µl, 0.558 mmol) in DCM (100 µl) was added at a rate of 10 µl/min. The reaction mixture was stirred −10° C. for additional 5 h then poured onto KHSO₄ solution (30 mL, 5%). The separated aqueous layer was extracted with EtOAc (3×30 mL). The combined organic extract was washed with brine, dried over anhydrous MgSO₄, filtered, and concentrated in vacuo. The yellowish crude residue was refluxed in MeCN (20 mL) for 3 h then the solvent was removed in vacuo. The crude residue was used directly for the next step without further purification.

To a stirred solution of the crude residue in toluene/MeOH (5 mL, 4:1) at room temperature was dropwise added TMSCHN₂ (0.15 mL, 0.3 mmol, 2.0 M in hexanes). After addition of AcOH (0.15 mL), the reaction mixture was dried in vacuo. The crude residue was purified by silica gel flash chromatography eluting with hexanes/EtOAc (5:1→3:2) to afford 1-3d and 1-3c.

The crude 1-3d was purified through HPLC eluting with MeCN:H₂O (3:1) to yield pure compound 2.5 mg. $t_R$=25.3 min. [α]$^{20}_D$ −14.8° (c 0.27, CHCl$_3$); $^1$H NMR (600 MHz, CDCl$_3$) δ5.37 (dt, J=3.0, 9.2 Hz, 1H), 5.21 (d, J=8.1 Hz, 1H), 5.18 (s, 1H), 4.75 (d, J=2.0 Hz, 1H), 3.94 (s, 3H), 2.93-3.00 (m, 1H), 2.85-2.92 (m, 1H), 2.73 (d, J=9.2 Hz, 2H), 2.45 (br. s., 1H), 2.28-2.39 (m, 2H), 1.86-1.94 (m, 1H), 1.45 (s, 9H); $^{13}$C NMR (150 MHz, CDCl$_3$) δ178.5, 172.4, 169.4, 155.9, 99.5, 99.3, 94.7, 80.6, 59.4, 58.3, 53.3, 51.7, 48.4, 29.6, 28.5, 26.0; ESI-MS m/z: 583.2 [M+H]$^+$; ESI-HRMS: m/z calcd for C$_{18}$H$_{25}$N$_2$O$_5$$^{35}$Cl$_5$$^{37}$Cl [M+H]$^+$, 560.9865. found, 560.9860.

The crude 1-3c was purified through HPLC eluting with MeCN:H$_2$O (7:3) to yield pure compound 4.6 mg. t$_R$=38.5 min. [α]$^{20}_D$ +45.4° (c 1.3, CHCl$_3$); $^1$H NMR (600 MHz, CDCl$_3$) δ5.48 (dt, J=3.5, 8.9 Hz, 1H), 5.30 (d, J=8.7 Hz, 1H), 5.18 (s, 1H), 4.80 (br. s., 1H), 3.94 (s, 3H), 2.95-3.03 (m, 1H), 2.78-2.86 (m, 1H), 2.56-2.63 (m, 1H), 2.54 (dd, J=5.8, 9.4 Hz, 2H), 2.39-2.44 (m, 1H), 2.33-2.38 (m, 1H), 1.95-2.02 (m, 1H), 1.46 (s, 9H); $^{13}$C NMR (150 MHz, CDCl$_3$) δ178.6, 172.0, 169.0, 155.8, 99.4, 98.9, 94.5, 80.4, 59.5, 57.8, 53.6, 51.5, 48.9, 30.9, 28.5, 26.3; ESI-MS m/z: 583.2 [M+H]$^+$; ESI-HRMS: m/z calcd for C$_{18}$H$_{25}$N$_2$O$_5$$^{35}$Cl$_5$$^{37}$Cl [M+H]$^+$, 560.9865. found, 560.9873.

Compound 1-3d was dissolved in TFA/DCM (3 mL, 25%) and stirred at 0° C. for 1 h then was evaporated in vacuo. After addition of saturated NaHCO$_3$ solution (15 mL), the aqueous layer was extracted with EtOAc (3×15 mL). The combined organic extract was washed with brine, dried over anhydrous MgSO$_4$, filtered, and concentrated in vacuo. The crude residue was purified by silica gel flash chromatography eluting with hexanes/EtOAc (9:2→3:2) to afford free amine 1-4d. ESI-MS m/z: 461.0 [M+H]$^+$; ESI-HRMS: m/z calcd for C$_{13}$H$_{17}$N$_2$O$_3$Cl$_6$ [M+H]$^+$, 458.9370. found, 458.9372.

To a stirred solution of the crude free amine 1-4d in THF (2 mL) 0° C. was added propionyl chloride (34 μl, 0.38 mmol) and Et$_3$N (6 μl, 0.046 mmol). The reaction mixture was stirred at room temperature for 3 h. After addition of saturated NaHCO$_3$ solution (10 mL), the aqueous layer was extracted with EtOAc (3×10 mL). The combined organic extract was washed with brine, dried over anhydrous MgSO$_4$, filtered, and concentrated in vacuo. The crude residue was purified by silica gel flash chromatography eluting with hexanes/EtOAc (7:1→3:2) to afford 1-1d (2.4 mg, 0.0047 mmol) as a colourless solid in a yield of 1.7%. [α]$^{20}_D$ −28.3° (c 0.53, CHCl$_3$); $^1$H NMR (600 MHz, CDCl$_3$) δ6.22 (d, J=8.7 Hz, 1H), 5.70 (td, J=3.6, 9.0 Hz, 1H), 5.19 (s, 1H), 4.75 (dd, J=3.1, 5.6 Hz, 1H), 3.95 (s, 3H), 2.93-3.01 (m, 1H), 2.75-2.84 (m, 1H), 2.63-2.72 (m, 2H), 2.43-2.51 (m, 1H), 2.33-2.40 (m, 2H), 2.28 (qd, J=3.3, 7.6 Hz, 2H), 1.91-1.99 (m, 1H), 1.17 (t, J=7.7 Hz, 3H); $^{13}$C NMR (150 MHz, CDCl$_3$) δ178.6, 174.1, 171.7, 169.3, 99.5, 99.2, 94.7, 59.4, 58.3, 51.7, 51.6, 48.4, 30.2, 29.8, 26.1, 9.9; ESI-MS m/z: 539.2 [M+Na]$^+$; ESI-HRMS: m/z calcd for C$_{16}$H$_{21}$N$_2$O$_4$$^{35}$Cl$_5$$^{37}$Cl [M+H]$^+$, 516.9603. found, 516.9608.

Compound 1-3c was dissolved in TFA/DCM (3 mL, 25%) and stirred at 0° C. for 1 h then was evaporated in vacuo. After addition of saturated NaHCO$_3$ solution (15 mL), the aqueous layer was extracted with EtOAc (3×15 mL). The combined organic extract was washed with brine, dried over anhydrous MgSO$_4$, filtered, and concentrated in vacuo. The crude residue was purified by silica gel flash chromatography eluting with hexanes/EtOAc (9:2→1:2) to afford free amine 1-4c. $^1$H NMR (600 MHz, CDCl$_3$) δ5.14 (s, 1H), 4.29 (t, J=5.0 Hz, 1H), 3.88 (s, 3H), 2.78 (ddd, J=4.3, 11.4, 14.2 Hz, 1H), 2.54-2.63 (m, 1H), 2.23-2.31 (m, 1H), 2.13-2.22 (m, 1H), 1.75 (br. s., 4H); ESI-MS m/z: 461.0 [M+H]$^+$; ESI-HRMS: m/z calcd for C$_{13}$H$_{17}$N$_2$O$_3$Cl$_6$ [M+H]$^+$, 458.9370. found, 458.9381.

To a stirred solution of the crude free amine 1-4c in THF (2 mL) 0° C. was added propionyl chloride (34 μl, 0.38 mmol) and Et$_3$N (6 μl, 0.046 mmol). The reaction mixture was stirred at room temperature for 3 h. After addition of saturated NaHCO$_3$ solution (10 mL), the aqueous layer was extracted with EtOAc (3×10 mL). The combined organic extract was washed with brine, dried over anhydrous MgSO$_4$, filtered, and concentrated in vacuo. The crude residue was purified by silica gel flash chromatography eluting with hexanes/EtOAc (3:2→1:1) to afford 1-1c (3.0 mg, 0.0058 mmol) as a colourless solid in a yield of 2.1%. [α]$^{20}_D$ +27.6° (c 0.65, CHCl$_3$); $^1$H NMR (600 MHz, CDCl$_3$) δ6.28 (d, J=8.2 Hz, 1H), 5.79 (td, J=3.6, 8.4 Hz, 1H), 5.19 (s, 1H), 4.79 (m, 1H), 3.95 (s, 3H), 2.98 (ddd, J=4.6, 11.8, 14.3 Hz, 1H), 2.71-2.79 (m, 1H), 2.57-2.63 (m, 1H), 2.54 (dd, J=6.1, 9.2 Hz, 2H), 2.42-2.49 (m, 1H), 2.34-2.41 (m, 1H), 2.30 (qd, J=3.8, 7.6 Hz, 2H), 1.99-2.08 (m, 1H), 1.19 (t, J=7.7 Hz, 3H); $^{13}$C NMR (150 MHz, CDCl$_3$) δ178.6, 174.0, 171.7, 168.9, 99.3, 98.9, 94.5, 59.5, 57.9, 51.9, 51.4, 48.9, 31.1, 29.9, 26.3, 9.9; ESI-MS m/z: 539.2 [M+Na]$^+$; ESI-HRMS: m/z calcd for C$_{16}$H$_{21}$N$_2$O$_4$$^{35}$Cl$_5$$^{37}$Cl [M+H]$^+$, 516.9603. found, 516.9598.

Example 4

Synthesis of 1-5d

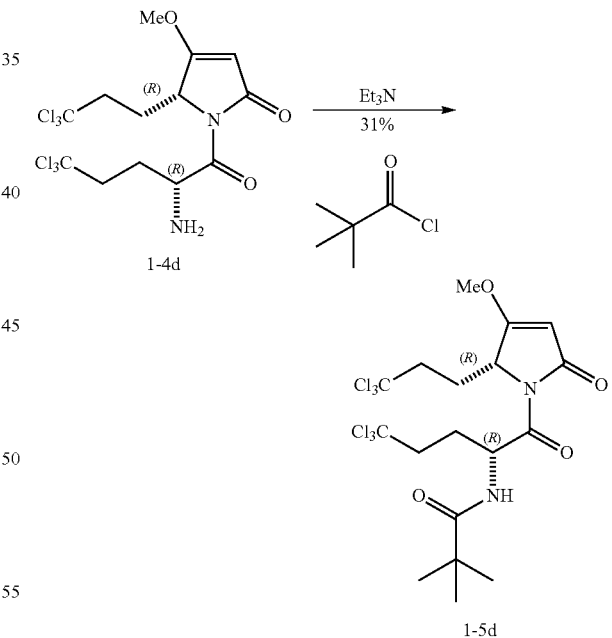

To a stirred solution of the crude free amine 1-4d (6 mg, 0.013 mmol) in THF (2 mL) 0° C. was added pivaloyl chloride (34 μl, 0.38 mmol) and Et$_3$N (6 μl, 0.046 mmol). The reaction mixture was stirred at room temperature for 3 h. After addition of saturated NaHCO$_3$ solution (10 mL), the aqueous layer was extracted with EtOAc (3×10 mL). The combined organic extract was washed with brine, dried over anhydrous MgSO$_4$, filtered, and concentrated in vacuo. The crude residue was purified by silica gel flash chromatography eluting with hexanes/EtOAc (25:2→5:1) to afford 1-5d (2.2 mg, 0.0040 mmol) as a colourless solid in a yield of 31%. $[\alpha]^{20}_D$ −17.3° (c 0.23, CHCl$_3$); $^1$H NMR (600 MHz, CDCl$_3$) δ6.41 (d, J=7.9 Hz, 1H), 5.60 (dt, J=3.4, 8.7 Hz, 1H), 5.18 (s, 1H), 4.76 (dd, J=3.2, 5.1 Hz, 1H), 3.94 (s, 3H), 2.96 (ddd, J=4.9, 11.4, 14.4 Hz, 1H), 2.76 (ddd, J=3.5, 11.5, 14.6 Hz, 1H), 2.65-2.73 (m, 2H), 2.43-2.50 (m, 1H), 2.37-2.43 (m, 1H), 2.29-2.37 (m, 1H), 1.94-2.03 (m, 1H), 1.23 (s, 9H); $^{13}$C NMR (150 MHz, CDCl$_3$) δ178.9, 178.5, 171.8, 169.3, 99.5, 99.2, 94.6, 59.4, 58.3, 51.9, 51.7, 48.4, 39.0, 29.9, 27.7, 26.0; ESI-MS m/z: 567.0 [M+Na]$^+$; ESI-HRMS: m/z calcd for C$_{18}$H$_{24}$N$_2$O$_4$NaCl$_6$ [M+Na]$^+$, 564.9765. found, 564.9756.

Example 5

Preparation of Compound (R)-4

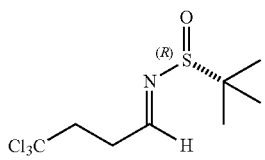

(R)-4

Under a similar procedure described in Example 1, (R)-4 (2.92 g, 10.5 mmol) was prepared from 3 (2.0 g, 11.3 mmol) as a colourless oil in a yield of 93%. The crude residue was purified by silica gel flash chromatography eluting with hexanes/EtOAc (36:1). $[\alpha]^{20}_D$ −162.3° (c 1.0, CHCl$_3$); $^1$H NMR (400 MHz, CDCl$_3$) δ8.16 (br. s., 1H), 3.05-3.17 (m, 2H), 2.98-3.04 (m, 2H), 1.19 (s, 9H); $^{13}$C NMR (100 MHz, CDCl$_3$) δ166.0, 99.0, 57.0, 50.3, 33.3, 22.5; ESI-MS m/z: 280.3 [M+H]$^+$; ESI-HRMS: m/z calcd for C$_8$H$_{15}$NO$^{32}$S$^{35}$Cl$_3$ [M+H]$^+$, 277.9940. found, 277.9938.

Example 6

Preparation of Compound (R,R)-5

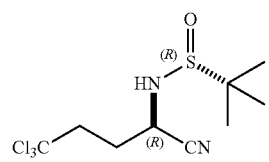

(R,R)-5

Under a similar procedure described in Example 1, (R,R)-5 (2.27 g, 7.42 mmol) was prepared from (R)-4 (2.50 g, 8.97 mmol) as a colourless oil in a yield of 25% (83% for both diastereomers). $[\alpha]^{20}_D$ −28.0° (c 0.4, CHCl$_3$); $^1$H NMR (400 MHz, CDCl$_3$) δ4.36 (br. s., 1H), 4.16 (br. s., 1H), 2.92 (t, J=7.6 Hz, 2H), 2.28-2.52 (m, 2H), 1.28 (s, 9H); $^{13}$C NMR (100 MHz, CDCl$_3$) δ118.5, 98.2, 57.8, 50.6, 45.2, 31.7, 22.8; ESI-MS m/z: 329.3 [M+Na]$^+$; ESI-HRMS: m/z calcd for C$_9$H$_{16}$N$_2$O$^{32}$S$^{35}$Cl$_3$ [M+H]$^+$, 305.0049. found, 305.0056.

Example 7

Preparation of 1-7c and 1-7d

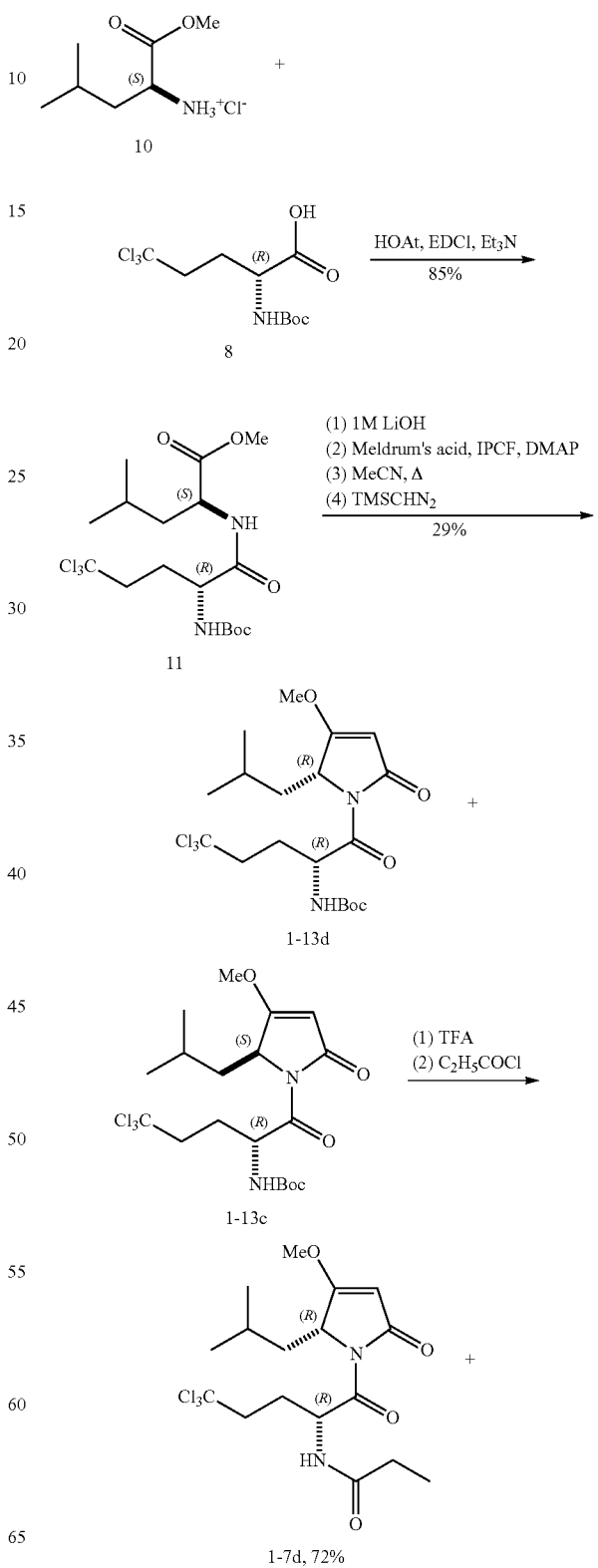

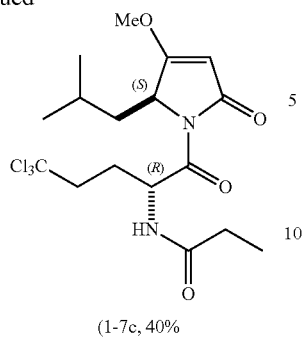

(1-7c, 40%)

11 (196 mg, 0.436 mmol) was prepared from 10 (140 mg, 0.770 mmol) and 8 (165 mg, 0.514 mmol) as illustrated above and isolated as a colourless oil in a yield of 85%. The crude residue was purified by silica gel flash chromatography eluting with hexanes/EtOAc (5:1→3:1). $[\alpha]^{20}_D$ +6.4° (c 1.0, CHCl$_3$); $^1$H NMR (400 MHz, CDCl$_3$) δ6.90 and 6.82 (br. s. each, 1H), 5.35 and 5.25 (d each, J=5.5 Hz and 7.9 Hz each, 1H), 4.60 (td, J=4.4, 8.8 Hz, 1H), 4.32 (br. s., 1H), 3.72 (s, 3H), 2.67-2.85 (m, 2H), 2.29-2.41 (m, 1H), 2.01-2.15 (m, 1H), 1.59-1.70 (m, 2H), 1.52-1.59 (m, 1H), 1.45 (s, 9H), 0.87-0.97 (m, 6H); $^{13}$C NMR (100 MHz, CDCl$_3$) δ173.4, 171.2, 155.9, 99.4, 80.7, 52.6, 51.2, 50.9, 41.5, 41.4, 29.7, 28.5, 25.1, 23.0, 21.9; ESI-MS m/z: 471.3 [M+Na]$^+$; ESI-HRMS: m/z calcd for $C_{17}H_{29}N_2O_5Na^{35}Cl_3$ [M+Na]$^+$, 469.1040. found, 469.1044.

1-7d (2.5 mg, 0.0058 mmol) was prepared from 11 (100 mg, 0.223 mmol) as a colourless oil. The crude residue was purified by silica gel flash chromatography eluting with hexanes/EtOAc (5:1→3:2). The yield from 1-13d was 72%. $[\alpha]^{20}_D$ -76.0° (c 0.5, CHCl$_3$); $^1$H NMR (600 MHz, CDCl$_3$) δ6.30 (d, J=8.7 Hz, 1H), 5.74 (td, J=3.1, 9.0 Hz, 1H), 5.09 (s, 1H), 4.60 (t, J=5.1 Hz, 1H), 3.89 (s, 3H), 2.98 (ddd, J=4.6, 11.6, 14.5 Hz, 1H), 2.73-2.80 (m, 1H), 2.32-2.39 (m, 1H), 2.29 (q, J=7.5 Hz, 2H), 1.88-1.95 (m, 1H), 1.82-1.85 (m, 2H), 1.74-1.80 (m, 1H), 1.18 (t, J=7.4 Hz, 3H), 0.94 (d, J=6.1 Hz, 3H), 0.89 (d, J=6.7 Hz, 3H); $^{13}$C NMR (150 MHz, CDCl$_3$) δ181.3, 173.8, 171.3, 169.8, 99.6, 93.6, 59.0, 59.0, 51.6, 51.5, 39.2, 30.6, 29.9, 24.4, 23.9, 22.7, 10.0; ESI-MS m/z: 451.2 [M+Na]$^+$; ESI-HRMS: m/z calcd for $C_{17}H_{26}N_2O_4Cl_3$ [M+H]$^+$, 427.0958. found, 427.0961.

1-7c (3.9 mg, 0.00914 mmol) was prepared from 1-13c (8.5 mg, 0.0228 mmol) as a colourless oil in a yield of 40%. The crude residue was purified by silica gel flash chromatography eluting with hexanes/EtOAc (3:2→1:1). $[\alpha]^{20}_D$ +47.50 (c 0.4, CHCl$_3$); $^1$H NMR (600 MHz, CDCl$_3$) δ6.33 (d, J=8.2 Hz, 1H), 5.77 (td, J=3.3, 8.6 Hz, 1H), 5.09 (s, 1H), 4.66 (dd, J=3.1, 6.7 Hz, 1H), 3.89 (s, 3H), 2.99 (ddd, J=4.4, 12.0, 14.3 Hz, 1H), 2.71-2.78 (m, 1H), 2.46 (tt, J=4.2, 12.7 Hz, 1H), 2.29 (qd, J=3.8, 7.6 Hz, 2H), 1.95-2.03 (m, J=3.8, 9.0, 12.5, 12.5 Hz, 1H), 1.80-1.85 (m, 1H), 1.73-1.80 (m, 2H), 1.18 (t, J=7.7 Hz, 3H), 0.94 (d, J=5.6 Hz, 3H), 0.91 (d, J=6.1 Hz, 3H); $^{13}$C NMR (150 MHz, CDCl$_3$) δ181.2, 173.9, 171.3, 169.5, 99.5, 93.5, 59.1, 58.6, 51.8, 51.5, 39.4, 31.0, 29.9, 24.5, 24.0, 22.8, 10.0; ESI-MS m/z: 451.2 [M+Na]$^+$; ESI-HRMS: m/z calcd for $C_{17}H_{25}N_2O_4NaCl_3$ [M+Na]$^+$, 449.0778. found, 449.0775.

Example 8

Preparation of 1-8c and 1-8d

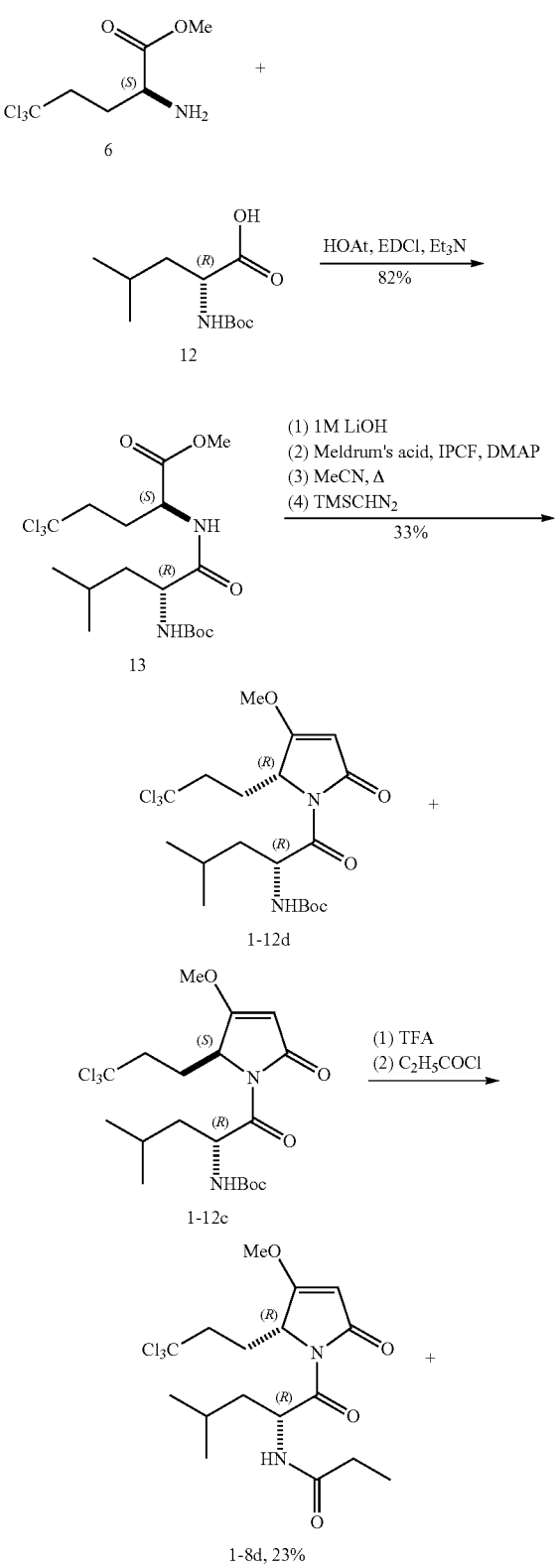

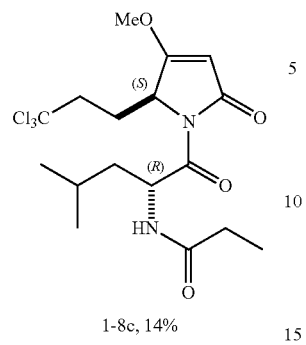

1-8c, 14%

Example 9

Preparation of 1-1a and 1-1b

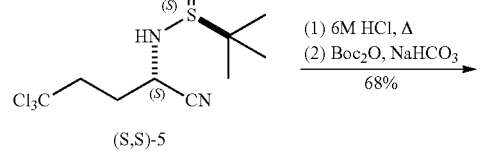

13 (82 mg, 0.183 mmol) was prepared from 6 (52 mg, 0.221 mmol) and 11 (80 mg, 0.350 mmol) as a colourless oil in a yield of 82%. The crude residue was purified by silica gel flash chromatography eluting with hexanes/EtOAc (6:1→3:1). $[\alpha]^{20}_D$+36.1° (c 0.8, CHCl$_3$); $^1$H NMR (400 MHz, CDCl$_3$) δ7.04 and 6.93 (br. s. each, 1H), 5.01 (br. s., 1H), 4.69 (td, J=4.9, 7.9 Hz, 1H), 4.16 (br. s., 1H), 3.77 (s, 3H), 2.73-2.82 (m, 1H), 2.61-2.71 (m, 1H), 2.32-2.43 (m, 1H), 2.06-2.17 (m, 1H), 1.61-1.72 (m, 2H), 1.47-1.53 (m, 1H), 1.43 (s, 9H), 0.90-0.95 (m, 6H); $^{13}$C NMR (100 MHz, CDCl$_3$) δ172.9, 171.9, 155.9, 99.1, 80.4, 53.3, 52.9, 51.1, 50.9, 41.0, 29.7, 28.5, 25.0, 23.1, 22.3; ESI-MS m/z: 469.2 [M+Na]$^+$; ESI-HRMS: m/z calcd for C$_{17}$H$_{30}$N$_2$O$_5$$^{35}$Cl$_3$ [M+H]$^+$, 447.1220. found, 447.1231.

1-8d (4.0 mg, 0.0093 mmol) was prepared from 13 (79.2 mg, 0.176 mmol) as a colourless oil. The crude residue was purified by silica gel flash chromatography eluting with hexanes/EtOAc (5:1→3:2). The yield from 1-12d was 23%. $[\alpha]^{20}_D$−25.0° (c 0.4, CHCl$_3$); $^1$H NMR (600 MHz, CDCl$_3$) δ5.97 (d, J=7.7 Hz, 1H), 5.70 (ddd, J=3.1, 8.4, 11.0 Hz, 1H), 5.15 (s, 1H), 4.72 (dd, J=3.1, 5.6 Hz, 1H), 3.92 (s, 3H), 2.76 (ddd, J=4.4, 11.9, 14.0 Hz, 1H), 2.65-2.72 (m, 1H), 2.43 (ddd, J=3.8, 11.6, 14.2 Hz, 1H), 2.28-2.35 (m, 1H), 2.24 (qd, J=4.1, 7.5 Hz, 2H), 1.69-1.76 (m, 1H), 1.60-1.63 (m, 1H), 1.41-1.46 (m, 1H), 1.15 (t, J=7.7 Hz, 3H), 1.04 (d, J=6.7 Hz, 3H), 0.94 (d, J=6.7 Hz, 3H); $^{13}$C NMR (150 MHz, CDCl$_3$) δ178.2, 173.8, 173.7, 169.1, 99.4, 94.7, 59.3, 58.3, 51.7, 48.2, 41.0, 29.7, 26.0, 25.2, 23.8, 21.4, 9.9; ESI-MS m/z: 451.3 [M+Na]$^+$; ESI-HRMS: m/z calcd for C$_{17}$H$_{25}$N$_2$O$_4$NaCl$_3$ [M+Na]$^+$, 449.0778. found, 449.0780.

1-8c (1.3 mg, 0.003 mmol) was prepared from 1-12c (8.0 mg, 0.0215 mmol) as a colourless oil in a yield of 14%. The crude residue was purified by silica gel flash chromatography eluting with hexanes/EtOAc (3:2→1:1). $[\alpha]^{20}_D$+60.0° (c 0.33, CHCl$_3$); $^1$H NMR (600 MHz, CDCl$_3$) δ5.96 (br. s., 1H), 5.78 (t, J=8.4 Hz, 1H), 5.15 (s, 1H), 4.77 (dd, J=3.3, 5.4 Hz, 1H), 3.92 (s, 3H), 2.55-2.62 (m, 1H), 2.50 (dd, J=6.7, 9.2 Hz, 2H), 2.30-2.36 (m, 1H), 2.27 (qd, J=2.3, 7.6 Hz, 2H), 1.71-1.77 (m, 1H), 1.65 (ddd, J=3.1, 10.2, 13.3 Hz, 1H), 1.44-1.50 (m, 1H), 1.17 (t, J=7.4 Hz, 3H), 1.07 (d, J=6.7 Hz, 3H), 0.95 (d, J=6.7 Hz, 3H); $^{13}$C NMR (150 MHz, CDCl$_3$) δ178.3, 173.9, 173.5, 168.9, 99.0, 94.6, 59.4, 57.8, 51.9, 48.8, 42.1, 29.8, 26.1, 25.4, 23.8, 21.3, 9.9; ESI-MS m/z: 451.3 [M+Na]$^+$; ESI-HRMS: m/z calcd for C$_{17}$H$_{25}$N$_2$O$_4$NaCl$_3$ [M+Na]$^+$, 449.0778. found, 449.0781.

Compound (S,S)-5 (258 mg, 0.844 mmol) was refluxed in HCl (10 mL, 6 M) for 0.5 h. The reaction mixture was cooled to room temperature and washed with diethyl ether (2×10 mL). The aqueous layer was evaporated at 50° C. in vacuo and freeze dried overnight. The yellowish solid was used without purification.

To a stirred solution of the solid in saturated NaHCO$_3$ solution (20 mL) was added Boc$_2$O (184 mg, 0.844 mmol) in THF (20 mL) at room temperature. The reaction mixture was stirred at room temperature overnight. Placed in an ice/water bath, the reaction mixture was added 1M HCl dropwise until its pH value was adjusted to pH=3. The aqueous suspension was extracted with EtOAc (3×15 mL). The combined organic extract was dried over anhydrous MgSO$_4$, filtered, and concentrated in vacuo. The crude residue was purified by silica gel flash chromatography eluting with hexanes/EtOAc (2:1→1:1) to afford 14 (186 mg, 0.575 mmol) as a colourless oil in a yield of 68%. $[\alpha]^{20}_D$+26.1° (c 1.8, CHCl$_3$); $^1$H NMR (400 MHz, MeOH-d$_4$) δ5.09 (br. s., 2H), 4.19 (dd, J=4.7, 7.8 Hz, 1H), 2.66-2.91 (m, 2H), 2.21-2.37 (m, 1H), 2.01-2.18 (m, 1H), 1.38 (s, 9H); $^{13}$C NMR (100 MHz, MeOH-d$_4$) δ174.9, 158.0, 100.6, 80.8, 53.6, 52.6, 50.0, 30.1, 28.8; ESI-MS m/z: 320.3 [M+H]$^+$; ESI-HRMS: m/z calcd for C$_{10}$H$_{16}$NO$_4$NaCl$_3$ [M+Na]$^+$, 342.0043. found, 342.0044.

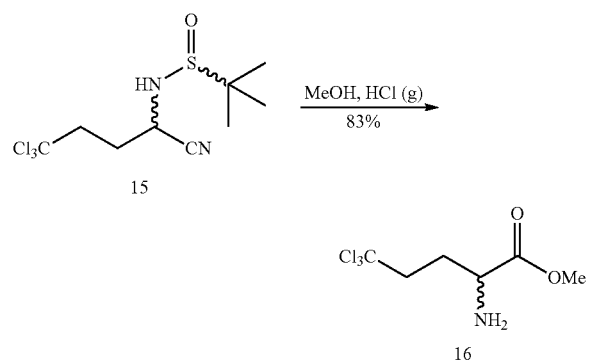

Methanolysis of Strecker product 15 afforded racemic 5,5,5-trichloronorvaline methyl ester 16 in a yield of 83% according to the above scheme.

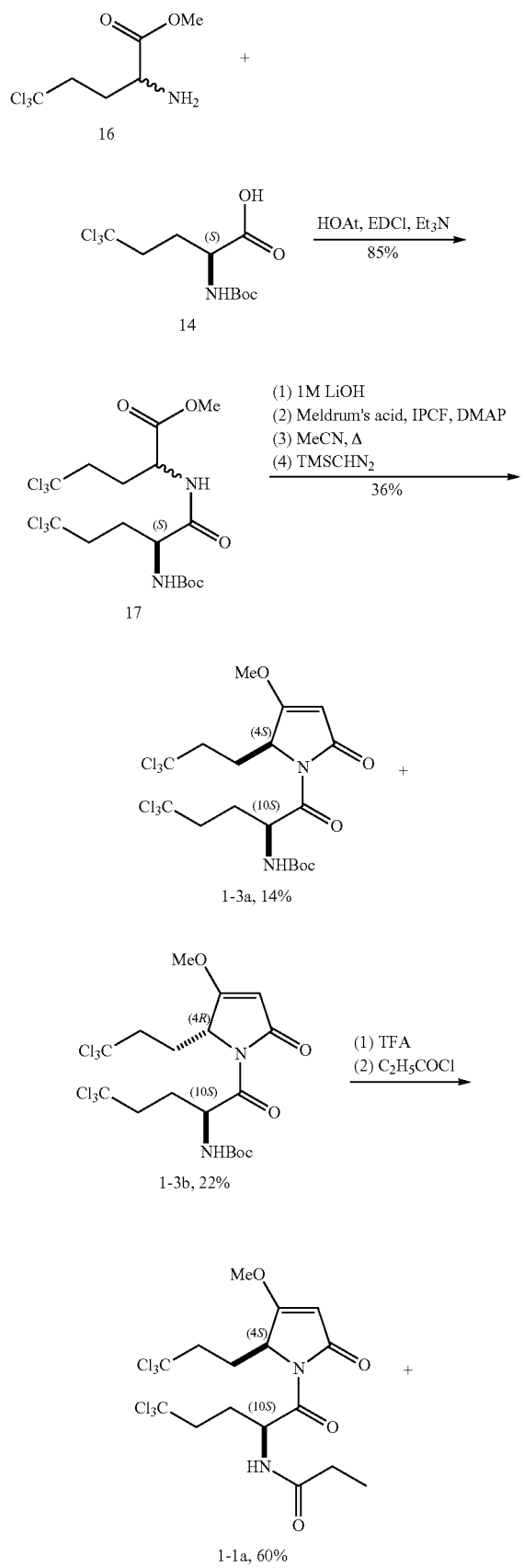

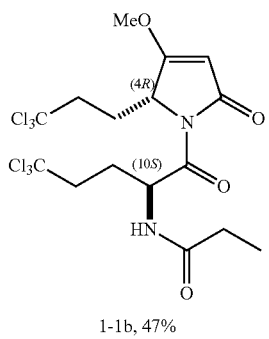

1-1b, 47%

Under a similar procedure to that described above, 17 (70 mg, 0.130 mmol) was prepared from 16 (36 mg, 0.153 mmol) and 14 (49 mg, 0.153 mmol) as a colourless oil in a yield of 85%. The crude residue was purified by silica gel flash chromatography eluting with hexanes/EtOAc (6:1→3:1). $[\alpha]^{20}_D$+3.3° (c 1.2, CHCl$_3$); $^1$H NMR (600 MHz, CDCl$_3$) δ 6.85 (d, J=6.1 Hz, 1H), 5.11 (d, J=7.2 Hz, 1H), 4.72 (td, J=5.1, 7.9 Hz, 1H), 4.22 (d, J=6.1 Hz, 1H), 3.81 (s, 3H), 2.74-2.85 (m, 3H), 2.64-2.72 (m, 1H), 2.40-2.47 (m, 1H), 2.32-2.38 (m, 1H), 2.07-2.20 (m, 2H), 1.46 (s, 9H); $^{13}$C NMR (150 MHz, CDCl$_3$) δ171.7, 171.2, 155.9, 99.2, 99.0, 81.2, 53.4, 53.2, 51.3, 51.2, 51.0, 29.7, 29.1, 28.5; ESI-MS m/z: 559.2 [M+Na]$^+$; ESI-HRMS: m/z calcd for $C_{16}H_{24}N_2O_5NaCl_6$ [M+Na]$^+$, 556.9714. found, 556.9713.

Under a similar procedure described above, 1-1a (3.8 mg, 0.0073 mmol) was prepared from 19 (60.8 mg, 0.113 mmol) as a colourless oil. The crude residue was purified by silica gel flash chromatography eluting with hexanes/EtOAc (5:1→3:2). The yield from 1-3a was 60%. $[\alpha]^{20}_D$+50.0° (c 0.16, CHCl$_3$); $^1$H NMR (600 MHz, CDCl$_3$) δ6.21 (d, J=8.2 Hz, 1H), 5.70 (td, J=3.6, 9.0 Hz, 1H), 5.19 (s, 1H), 4.75 (dd, J=3.3, 5.4 Hz, 1H), 3.94 (s, 3H), 2.94-3.01 (m, 1H), 2.76-2.82 (m, 1H), 2.64-2.72 (m, 2H), 2.43-2.50 (m, 1H), 2.33-2.40 (m, 2H), 2.28 (qd, J=3.6, 7.7 Hz, 2H), 1.91-1.99 (m, 1H), 1.17 (t, J=7.7 Hz, 3H); $^{13}$C NMR (150 MHz, CDCl$_3$) δ178.6, 174.0, 171.7, 169.3, 99.5, 99.2, 94.7, 59.4, 58.3, 51.7, 51.6, 48.4, 30.2, 29.8, 26.1, 9.9; ESI-MS m/z: 539.1 [M+Na]$^+$; ESI-HRMS: m/z calcd for $C_{16}H_{20}N_2O_4Na^{35}Cl_6$ [M+Na]$^+$, 536.9453. found, 536.9441.

Under a similar procedure described above, 1-1b (2.2 mg, 0.0042 mmol) was prepared from 1-3b (8.9 mg, 0.0193 mmol) as a colourless oil in a yield of 22%. The crude residue was purified by silica gel flash chromatography eluting with hexanes/EtOAc (3:2→1:1). $[\alpha]^{20}_D$−56.0° (c 0.25, CHCl$_3$); $^1$H NMR (600 MHz, CDCl$_3$) δ6.27 (d, J=8.7 Hz, 1H), 5.79 (td, J=3.6, 8.7 Hz, 1H), 5.19 (s, 1H), 4.79 (m, 1H), 3.95 (s, 3H), 2.98 (ddd, J=4.6, 11.8, 14.3 Hz, 1H), 2.75 (ddd, J=3.6, 12.3, 14.3 Hz, 1H), 2.57-2.63 (m, 1H), 2.54 (dd, J=6.1, 8.7 Hz, 2H), 2.46 (tt, J=4.2, 12.7 Hz, 1H), 2.35-2.41 (m, 1H), 2.30 (qd, J=3.8, 7.6 Hz, 2H), 2.00-2.08 (m, 1H), 1.19 (t, J=7.4 Hz, 3H); $^{13}$C NMR (150 MHz, CDCl$_3$) δ178.6, 174.0, 171.7, 168.9, 99.3, 98.9, 94.5, 59.5, 57.9, 51.9, 51.4, 48.9, 31.1, 29.9, 26.3, 9.9; ESI-MS m/z: 539.1 [M+Na]$^+$; ESI-HRMS: m/z calcd for $C_{16}H_{20}N_2O_4Na^{35}Cl_6$ [M+Na]$^+$, 536.9452. found, 536.9456.

Example 10

Preparation of 1-9c

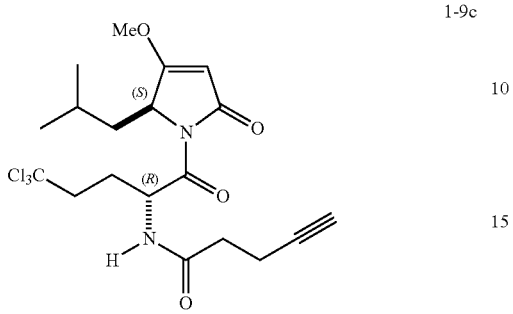

1-9c 1-9c (1.6 mg, 0.0035 mmol) was prepared from free amine analogue of 1-13c (6.0 mg, 0.0161 mmol) and pentynoyl chloride, and isolated as a colourless oil in a yield of 21%. The crude residue was purified by silica gel flash chromatography eluting with hexanes/EtOAc (5:1→2:1); $[α]^{20}_D$+50.0° (c 0.14, CHCl$_3$); $^1$H NMR (600 MHz, CDCl$_3$) δ 6.50 (d, J=8.1 Hz, 1H), 5.80 (dt, J=3.3, 8.5 Hz, 1H), 5.10 (s, 1H), 4.66 (dd, J=3.07, 6.66 Hz, 1H), 3.89 (s, 3H), 2.97-3.04 (m, 1H), 2.75-2.83 (m, 1H), 2.56-2.64 (m, 1H), 2.50-2.55 (m, 1H), 2.44-2.50 (m, 3H), 2.02-2.05 (m, 1H), 1.96-2.02 (m, 1H), 1.80-1.87 (m, 1H), 1.72-1.80 (m, 2H), 0.94 (d, J=6.1 Hz, 3H), 0.91 (d, J=6.1 Hz, 3H); $^{13}$C NMR (150 MHz, CDCl$_3$) δ181.2, 171.0, 170.9, 169.5, 99.5, 93.5, 83.0, 69.8, 59.1, 58.6, 52.0, 51.4, 39.3, 35.6, 31.0, 24.5, 24.0, 22.8, 15.2. ESI-MS m/z: 475.2 [M+Na]$^+$; ESI-HRMS: m/z calcd for C$_{19}$H$_{25}$N$_2$O$_4$NaCl$_3$ [M+Na]$^+$, 473.0778. found, 473.0781.

Example 11

Preparation of 1-2d

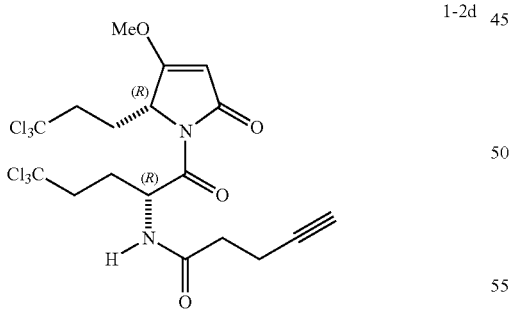

1-2d 1-2d (1.6 mg, 0.0035 mmol) was prepared from 1-4d (5 mg, 0.0108 mmol) and pentynoyl chloride as a colourless oil in a yield of 39%. The crude residue was purified by silica gel flash chromatography eluting with hexanes/EtOAc (10:1→5:1). $[α]^{20}_D$−30.0° (c 0.2, CHCl$_3$); $^1$H NMR (600 MHz, CDCl$_3$) δ6.41 (d, J=8.6 Hz, 1H), 5.74 (dt, J=3.2, 8.9 Hz, 1H), 5.19 (s, 1H), 4.70-4.79 (m, 1H), 3.95 (s, 3H), 2.95-3.02 (m, 1H), 2.81-2.88 (m, 1H), 2.64-2.72 (m, 2H), 2.55-2.63 (m, 1H), 2.51-2.55 (m, 1H), 2.44-2.51 (m, 3H), 2.33-2.42 (m, 2H), 2.03 (t, J=2.5 Hz, 1H), 1.93-2.00 (m, 1H); $^{13}$C NMR (150 MHz, CDCl$_3$) δ178.6, 171.4, 171.1, 169.2, 99.5, 99.2, 94.6, 83.0, 69.9, 59.4, 58.4, 51.8, 51.6, 48.5, 35.6, 30.2, 26.2, 15.1; ESI-MS m/z: 562.9 [M+Na]$^+$; ESI-HRMS: m/z calcd for C$_{18}$H$_{20}$N$_2$O$_4$Na$^{35}$Cl$_5$$^{37}$Cl [M+Na]$^+$, 562.9422. found, 562.9424.

Example 12

Preparation of 1-2c

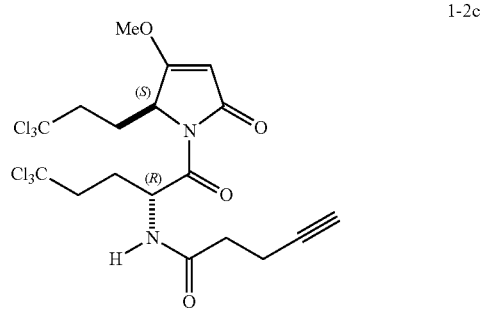

1-2c 1-2c (1.6 mg, 0.0035 mmol) was prepared from 1-4c (5 mg, 0.0108 mmol) and pentynoyl chloride as a colourless oil in a yield of 37%. The crude residue was purified by silica gel flash chromatography eluting with hexanes/EtOAc (5:1→2:1). $[α]^{20}_D$+25.9° (c 0.27, CHCl$_3$); $^1$H NMR (600 MHz, CDCl$_3$) δ6.47 (d, J=8.3 Hz, 1H), 5.83 (dt, J=3.6, 8.4 Hz, 1H), 5.20 (s, 1H), 4.80 (dd, J=3.7, 4.8 Hz, 1H), 3.95 (s, 3H), 2.97-3.03 (m, 1H), 2.75-2.82 (m, 1H), 2.57-2.64 (m, 2H), 2.52-2.57 (m, 2H), 2.45-2.52 (m, 3H), 2.35-2.42 (m, 1H), 2.04 (t, J=2.57 Hz, 1H), 2.01-2.09 (m, 1H); $^{13}$C NMR (150 MHz, CDCl$_3$) δ178.7, 171.4, 171.0, 168.9, 99.3, 98.9, 94.5, 82.9, 69.9, 59.5, 57.9, 52.1, 51.3, 48.9, 35.6, 31.0, 26.3, 15.2; ESI-MS m/z: 562.9 [M+Na]$^+$; ESI-HRMS: m/z calcd for C$_{18}$H$_{20}$N$_2$O$_4$Na$^{35}$Cl$_5$$^{37}$Cl [M+Na]$^+$, 562.9422. found, 562.9427.

Example 13

Preparation of 1-5c

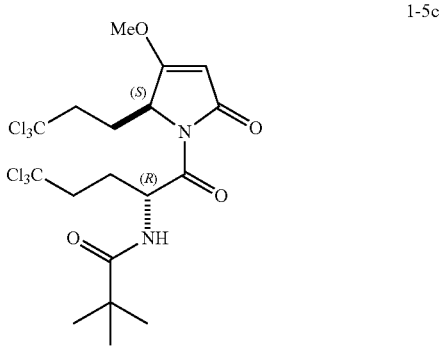

1-5c

Under a similar procedure described in Example 4, 1-5c (2.4 mg, 0.0044 mmol) was prepared from 1-4c (6 mg, 0.013 mmol) and pivaloyl chloride as a colourless oil in a yield of 34%. The crude residue was purified by silica gel flash chromatography eluting with hexanes/EtOAc (5:1→5:2).

[α]$^{20}_D$+24.2° (c 0.33, CHCl$_3$); $^1$H NMR (600 MHz, CDCl$_3$) δ6.51 (d, J=7.9 Hz, 1H), 5.75 (dt, J=3.5, 8.3 Hz, 1H), 5.19 (s, 1H), 4.78-4.80 (m, 1H), 3.94 (s, 3H), 2.97 (ddd, J=4.7, 11.7, 14.4 Hz, 1H), 2.72 (ddd, J=3.4, 11.7, 14.7 Hz, 1H), 2.57-2.63 (m, 1H), 2.53-2.56 (m, 2H), 2.47 (tt, J=4.1, 12.6 Hz, 1H), 2.34-2.41 (m, 1H), 2.01-2.08 (m, 1H), 1.25 (s, 9H); $^{13}$C NMR (150 MHz, CDCl$_3$) δ178.8, 178.6, 171.8, 168.9, 99.4, 98.9, 94.5, 59.5, 57.9, 51.9, 51.4, 48.9, 39.1, 31.0, 27.7, 26.3; ESI-MS m/z: 567.0 [M+Na]$^+$; ESI-HRMS: m/z calcd for C$_{18}$H$_{24}$N$_2$O$_4$NaCl$_6$ [M+Na]$^+$, 564.9765. found, 564.9764.

Example 14

Preparation of 1-6d

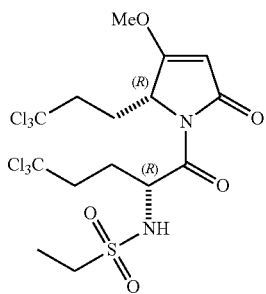

1-6d 1-6d (1.3 mg, 0.0023 mmol) was prepared from 1-4d (5 mg, 0.0108 mmol) and ethanesulfonyl chloride as a colourless oil in a yield of 21%. The crude residue was purified by silica gel flash chromatography eluting with hexanes/EtOAc (25:2→5:1). [α]$^{20}_D$+14.2° (c 0.21, CHCl$_3$); $^1$H NMR (600 MHz, CDCl$_3$) δ5.22-5.24 (m, 1H), 5.21 (s, 1H), 5.15-5.20 (m, J=2.8, 9.5 Hz, 1H), 4.78 (dd, J=3.0, 5.5 Hz, 1H), 3.96 (s, 3H), 3.00-3.07 (m, 2H), 2.92-3.00 (m, 2H), 2.74-2.81 (m, 1H), 2.65-2.71 (m, 1H), 2.44-2.50 (m, 1H), 2.35-2.42 (m, 1H), 2.26-2.32 (m, 1H), 1.87-1.95 (m, 1H), 1.39 (t, J=7.3 Hz, 3H); $^{13}$C NMR (150 MHz, CDCl$_3$) δ179.0, 171.7, 169.6, 99.1, 99.0, 94.6, 59.6, 58.5, 55.7, 51.6, 48.4, 48.0, 30.6, 26.1, 8.4; ESI-MS m/z: 574.9 [M+Na]$^+$; ESI-HRMS: m/z calcd for C$_{15}$H$_{20}$N$_2$O$_5$NaSCl$_6$ [M+Na]$^+$, 572.9122. found, 572.9114.

Example 15

Preparation of 1-6c

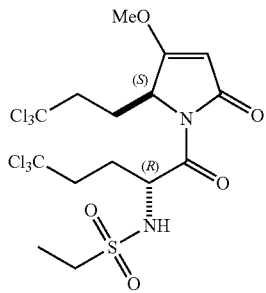

1-6c 1-6c (1.2 mg, 0.0021 mmol) was prepared from 1-4c (5 mg, 0.013 mmol) and ethanesulfonyl chloride as a colourless oil in a yield of 20%. The crude residue was purified by silica gel flash chromatography eluting with hexanes/EtOAc (5:1→5:2). [α]$^{20}_D$−13.8° (c 0.36, CHCl$_3$); $^1$H NMR (600 MHz, CDCl$_3$) δ5.31 (br. s., 1H), 5.23 (s, 1H), 4.85-4.89 (m, 1H), 3.98 (s, 3H), 3.01-3.10 (m, 2H), 2.92-3.00 (m, 2H), 2.59-2.65 (m, 1H), 2.57 (dd, J=5.3, 10.0 Hz, 2H), 2.40-2.44 (m, 1H), 2.35-2.40 (m, J=4.1 Hz, 1H), 2.07 (br. s., 1H), 1.41 (t, J=7.3 Hz, 3H); $^{13}$C NMR (150 MHz, CDCl$_3$) δ179.0, 171.5, 169.2, 99.0, 98.9, 94.4, 59.6, 58.0, 56.0, 51.3, 48.9, 48.1, 31.5, 26.2, 8.4; ESI-MS m/z: 574.9 [M+Na]$^+$; ESI-HRMS: m/z calcd for C$_{15}$H$_{20}$N$_2$O$_5$NaS$^{35}$Cl$_5$$^{37}$Cl [M+Na]$^+$, 574.9092. found, 574.9084.

Example 16

In Vitro Activity of Exemplary Compounds

LNCaP (2.4×10$^4$ cell/well) cells were seeded on 24-well plates overnight before transfection with PSA (6.1 kb)-luciferase plasmid (0.25 ug/well) in serum-free, red phenol-free media. The next day, cells were pre-treated with compounds of the invention for 1 hour before the addition of synthetic androgen, R1881 (1 nM) to transactivate androgen receptor (AR). After 48 h of incubation with R1881, the cells were harvested, and relative luciferase activity was determined as a read-out for androgen receptor (AR) transcriptional activity relative to a control. Test compounds were added to the cells at various concentrations and activity for each treatment was normalized to the predicted maximal activity induction (in the absence of test compounds, vehicle only). Transfection experiments were performed using triplicate wells.

Compounds 1-1a, 1-1b, 1-1c, 1-1d, 1-2c, 1-2d, 1-3c, 1-3d, 1-4c, 1-4d, 1-5c, 1-6d, 1-7c, 1-7d, 1-8c, 1-8d and 1-9c were each tested according to the above procedures. Each of the tested compounds, with the exception of 1-8d, showed a decrease in luciferase activity relative to the control (i.e., compounds had activity as inhibitors of AR transcriptional activity). Compound 1-8d showed a slight increase in luciferase activity relative to the control, which can possibly be explained by the variability in assay reproducibility.

Figure 2:
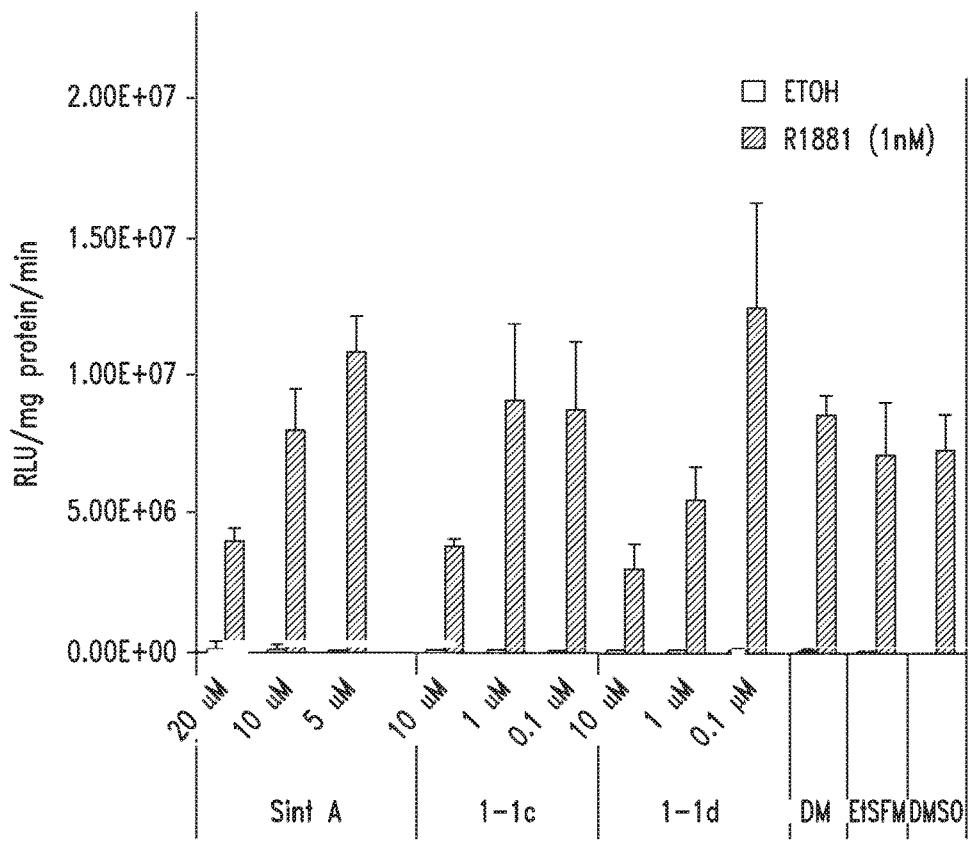
FIG. 2 presents comparative data for exemplary compounds and Sintokamide A.
Figure 3:
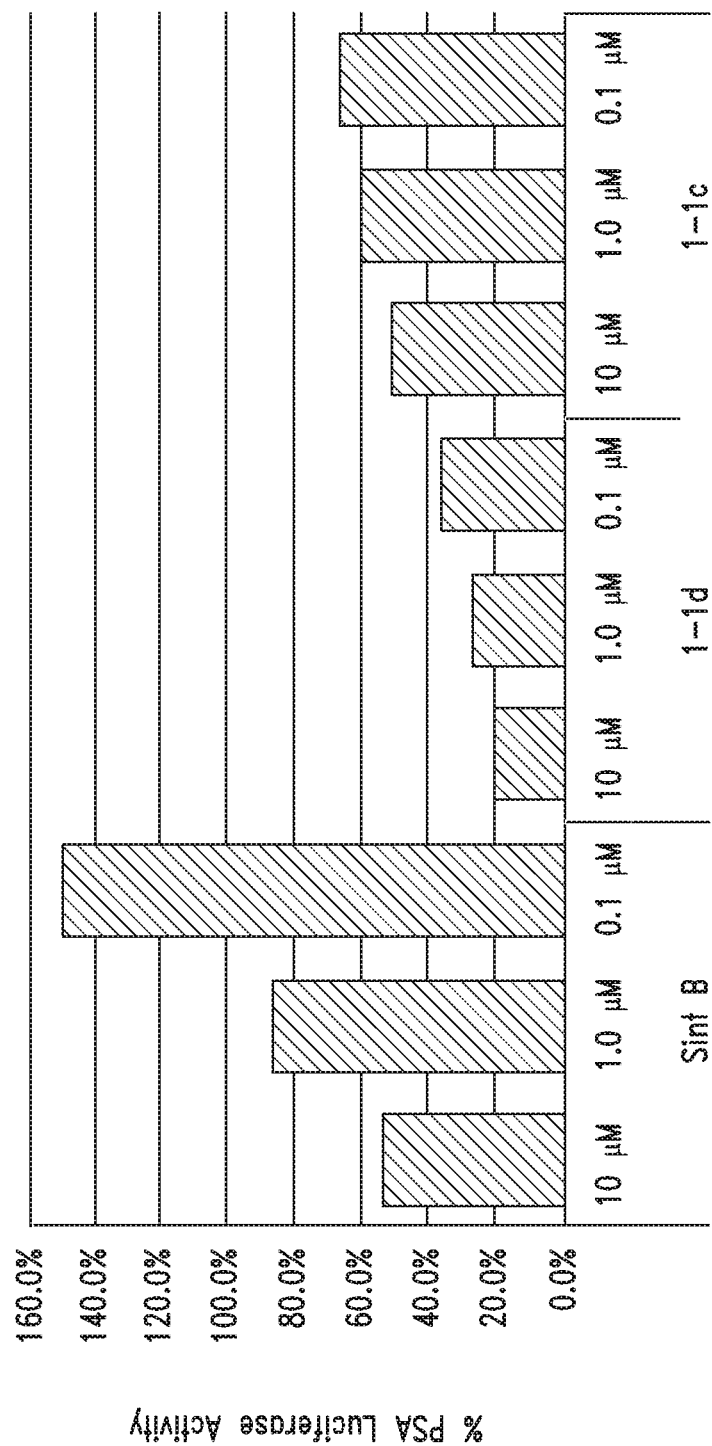
FIG. 3 presents comparative data for exemplary compounds and Sintokamide B.

Data comparing activity of exemplary compounds to Sintokamide A and Sintokamide B ("Sint A and Sint B, respectively) is provided in FIGS. 1-3.

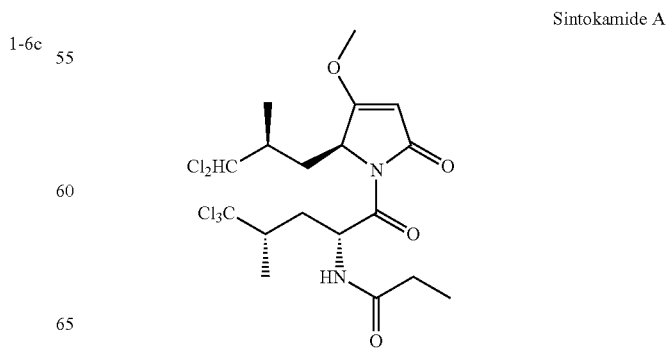

Sintokamide A

-continued

Sintokamide B

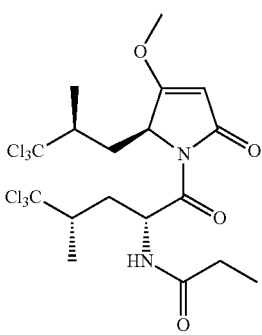

Furthermore, toxicity is assessed by both microscopic examination and reduction of protein levels. Solubility is assessed both macroscopically (cloudy media) and microscopically (formation of granules or crystals).

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, are incorporated herein by reference, in their entirety. Aspects of the embodiments can be modified, if necessary to employ concepts of the various patents, applications and publications to provide yet further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

We claim:

1. A pharmaceutical composition comprising a compound of structure (I), an additional therapeutic agent and a pharmaceutically acceptable carrier; wherein the compound of structure (I) has the following formula:

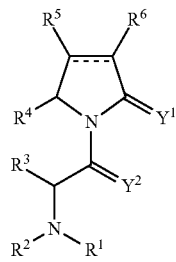

(I)

or a pharmaceutically acceptable salt, tautomer or stereoisomer thereof, wherein:
$Y^1$ and $Y^2$ are each independently O or S;
$R^1$ is H, $C_1$-$C_6$ alkyl or $C_1$-$C_6$ haloalkyl;
$R^2$ is H, —C(═O)$R^7$ or —S(O)$_n$$R^8$;
$R^3$ and $R^4$ are straight-chain $C_1$-$C_6$ haloalkyl;
$R^5$ and $R^6$ are each independently H, OH, $C_1$-$C_6$ alkyl, $C_1$-$C_6$ alkoxy, $C_1$-$C_6$ haloalkyl or $C_1$-$C_6$ haloalkoxy;
$R^7$ is $C_1$-$C_6$ alkyl, $C_1$-$C_6$ alkoxy, $C_1$-$C_6$ haloalkyl or $C_1$-$C_6$ haloalkoxy; $R^8$ is $C_1$-$C_6$ alkyl $C_1$-$C_6$ haloalkyl;

═══ is a carbon-carbon double bond or a carbon-carbon single bond, such that all valences are satisfied; and
n is 0, 1 or 2; and
wherein the additional therapeutic agent is for treating prostate cancer, breast cancer, ovarian cancer, endometrial cancer, bladder cancer, pancreatic cancer, hepatocellular cancer, kidney cancer, liver cancer, salivary gland carcinoma, hair loss, acne, hirsutism, ovarian cysts, polycystic ovary disease, precocious puberty, spinal and bulbar muscular atrophy or age-related macular degeneration.

2. The pharmaceutical composition of claim 1, wherein the additional therapeutic agent is enzalutamide, Galeterone, ARN-509, ODM-201, abiraterone, bicalutamide, nilutamide, flutamide, cyproterone acetate, docetaxel, Bevacizumab (Avastin), OSU-HDAC42, VITAXIN (humanized form of LM609), sunitinib (N-(2-diethylaminoethyl)-5-[(Z)-(5-fluoro-2-oxo-1H-indol-3-ylidene)methyl]-2,4-dimethyl-1H-pyrrole-3-carboxamide), ZD-4054, Cabazitaxel (XRP-6 258), MDX-010 (Ipilimumab), OGX 427, OGX 011, finasteride, dutasteride, turosteride, bexlosteride, izonsteride, FCE 28260, SKF105,111, Radium 233 or prednisone.

3. The pharmaceutical composition of claim 1, wherein the pharmaceutical composition is formulated for topical administrations.

4. A method for modulating androgen receptor (AR) activity, the method comprising administering the pharmaceutical composition of 1 to a subject in need thereof, wherein modulating androgen receptor (AR) activity is for the treatment of one or more of the following: prostate cancer, breast cancer, ovarian cancer, endometrial cancer, bladder cancer, pancreatic cancer, hepatocellular cancer, kidney cancer, liver cancer, salivary gland carcinoma, hair loss, acne, hirsutism, ovarian cysts, ovary disease, precocious puberty, spinal and bulbar muscular atrophy, polycystic or age-related macular degeneration.

5. The method of claim 4, wherein the method is for treatment of prostate cancer.

6. The method of claim 5, wherein the prostate cancer is castration resistant prostate cancer.

7. The method of claim 5, wherein the prostate cancer is androgen-dependent prostate cancer.

8. The method of claim 4, wherein the administration is topical.

9. The method of claim 4, wherein the administration is intravenous.

10. The pharmaceutical composition of claim 1, wherein the compound has the following structure (Ia):

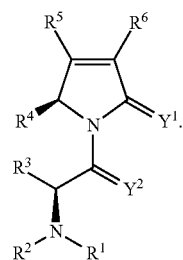

(Ia)

11. The pharmaceutical composition of claim 10, wherein at least one of $Y^1$ and $Y^2$ is O.

12. The pharmaceutical composition of claim 10, wherein at least one of $R^1$ and $R^2$ is H.

13. The pharmaceutical composition of claim 10, wherein R² is —C(=O)R⁷ or —S(O)$_n$R⁸.

14. The method pharmaceutical composition of claim 13, wherein R⁷ is ethyl, t-butyl

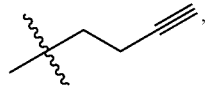 [SMILES: *CCC#C]

or t-butoxy; or R⁸ is ethyl.

15. The pharmaceutical composition of claim 13, wherein n is 2.

16. The pharmaceutical composition of claim 10, wherein R⁵ is C₁-C₆ alkoxy or R⁶ is H.

17. The pharmaceutical composition of claim 16, wherein C₁-C₆ alkoxy is methoxy.

18. The pharmaceutical composition of claim 10, wherein at least one of R³ or R⁴ is a straight-chain C₁-C₆ chloroalkyl.

19. The pharmaceutical composition of claim 18, wherein C₁-C₆ chloroalkyl comprises a perchloro-substituted carbon.

20. The pharmaceutical composition of claim 10, wherein R³ or R⁴, or both, is 3,3,3-trichloropropyl.

21. The pharmaceutical composition of claim 10, wherein === is a carbon-carbon double bond.

22. The pharmaceutical composition of claim 1, wherein the compound has one of the following structures:

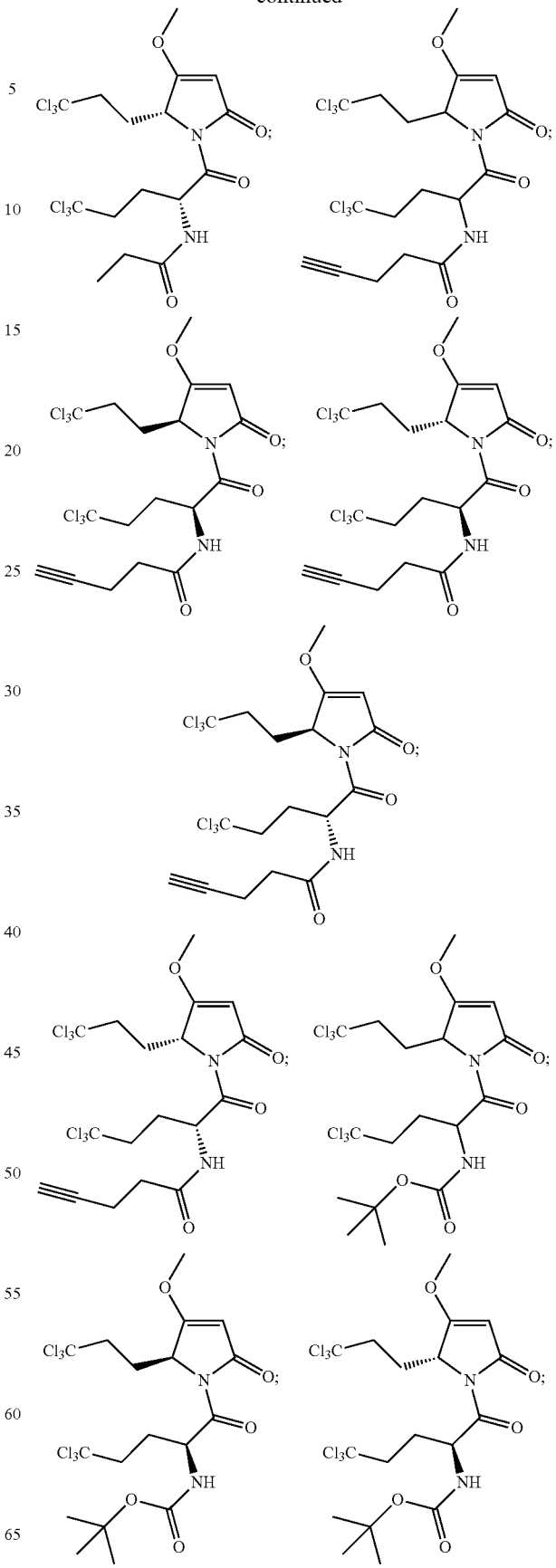

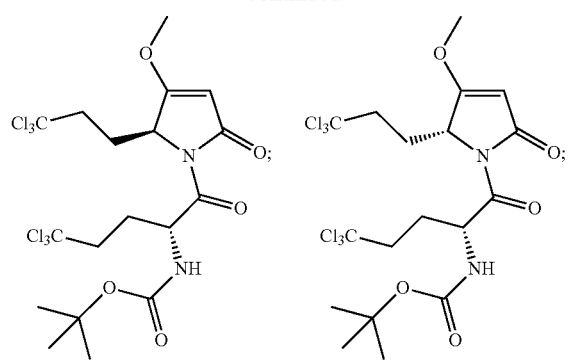
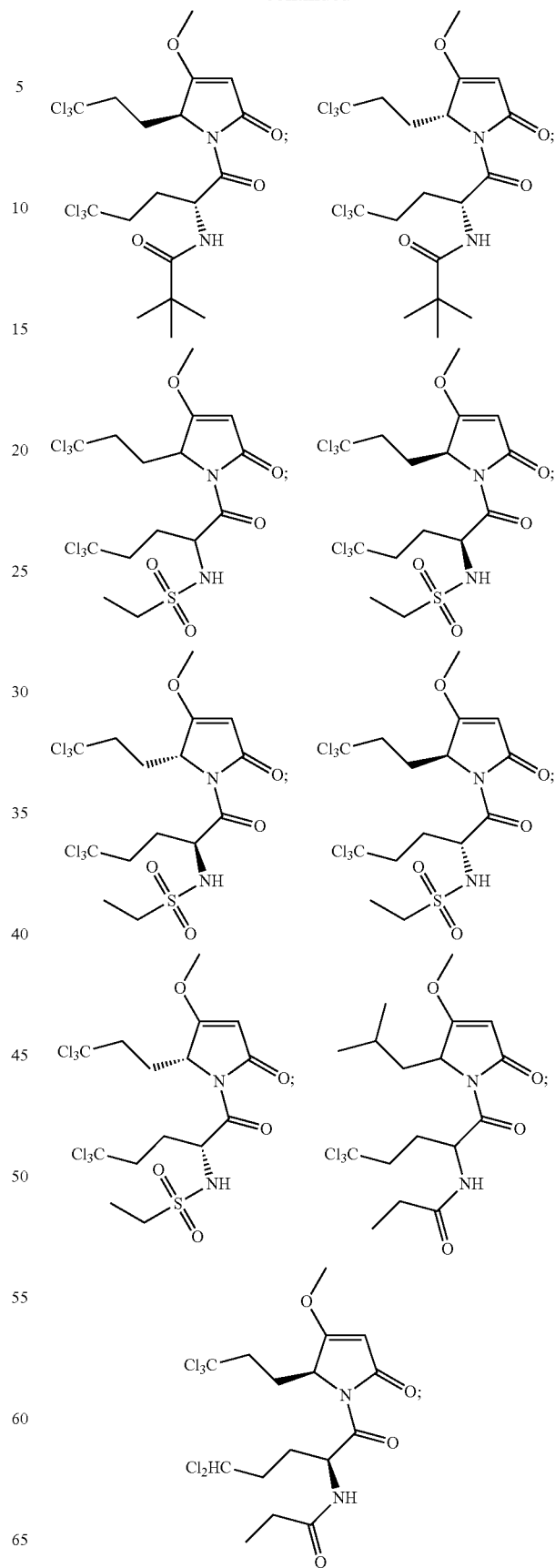

-continued
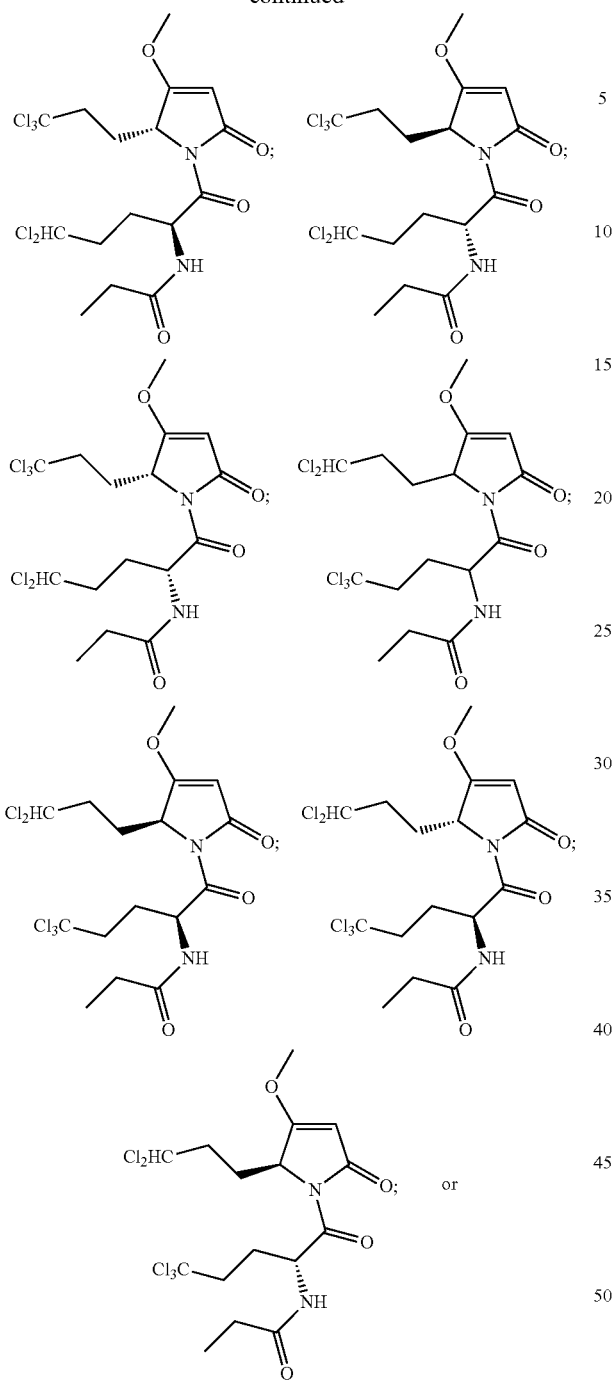
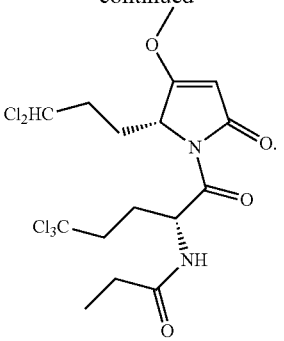
23. The pharmaceutical composition of claim 1, wherein the compound has the following structure (Ib), structure (Ic), or structure (Id):
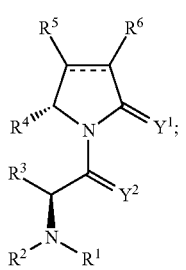
(Ib)
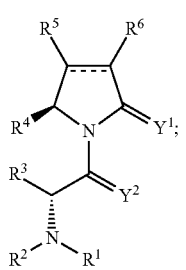
(Ic)
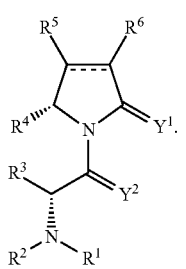
(Id)
* * * * *

UNITED STATES PATENT AND TRADEMARK OFFICE
CERTIFICATE OF CORRECTION

| | | |
|---|---|---|
| PATENT NO. | : 10,071,962 B2 | Page 1 of 1 |
| APPLICATION NO. | : 15/626526 | |
| DATED | : September 11, 2018 | |
| INVENTOR(S) | : Luping Yan et al. | |

It is certified that error appears in the above-identified patent and that said Letters Patent is hereby corrected as shown below:

In the Specification

At Column 1, Lines 16-19:
"This invention was made in part with government support under Grant No. 2R01 CA105304 awarded by the National Cancer Institute. The United States Government has certain rights in this invention."
Should read:
-- This invention was made with government support under R01 CA105304 awarded by the National Institutes of Health. The government has certain rights in the invention. --

Signed and Sealed this
Fifth Day of December, 2023

Katherine Kelly Vidal
*Director of the United States Patent and Trademark Office*